United States Patent
Ogawa et al.

(10) Patent No.: US 11,600,786 B2
(45) Date of Patent: Mar. 7, 2023

(54) ORGANIC ELECTROLUMINESCENT ELEMENT

(71) Applicant: NIPPON STEEL CHEMICAL & MATERIAL CO., LTD., Tokyo (JP)

(72) Inventors: Junya Ogawa, Kitakyushu (JP); Takahiro Kai, Kitakyushu (JP); Masanori Hotta, Kitakyushu (JP); Yuji Ikenaga, Kitakyushu (JP); Mitsuru Sakai, Kitakyushu (JP); Masashi Tada, Kitakyushu (JP); Tokiko Ueda, Kitakyushu (JP); Katsuhide Noguchi, Kitakyushu (JP)

(73) Assignee: NIPPON STEEL CHEMICAL & MATERIAL CO., LTD., Tokyo (JP)

( * ) Notice: Subject to any disclaimer, the term of this patent is extended or adjusted under 35 U.S.C. 154(b) by 187 days.

(21) Appl. No.: 15/558,898

(22) PCT Filed: Mar. 3, 2016

(86) PCT No.: PCT/JP2016/056643
§ 371 (c)(1),
(2) Date: Sep. 15, 2017

(87) PCT Pub. No.: WO2016/158191
PCT Pub. Date: Oct. 6, 2016

(65) Prior Publication Data
US 2018/0083201 A1   Mar. 22, 2018

(30) Foreign Application Priority Data
Mar. 30, 2015  (JP) ................................. 2015-070126

(51) Int. Cl.
*H01L 51/00* (2006.01)
*C09K 11/06* (2006.01)
(Continued)

(52) U.S. Cl.
CPC ........ *H01L 51/0072* (2013.01); *C07D 209/88* (2013.01); *C07D 405/14* (2013.01);
(Continued)

(58) Field of Classification Search
CPC ............. H01L 51/0072; H01L 51/0067; H01L 51/0073; H01L 51/0074; H01L 51/0085;
(Continued)

(56) References Cited

U.S. PATENT DOCUMENTS 9,859,502 B2 * 1/2018 Buesing ................ C07C 209/74
9,876,173 B2 * 1/2018 Zeng .................... H01L 51/0054
(Continued)

FOREIGN PATENT DOCUMENTS

JP    2012-49518 A    3/2012
JP    2012-195140 A   10/2012
WO    WO-2009/086028 A2   7/2009

OTHER PUBLICATIONS

International Search Report for the Application No. PCT/JP2016/056643 dated May 24, 2016.
(Continued)

*Primary Examiner* — Alexander C Kollias
(74) *Attorney, Agent, or Firm* — Birch, Stewart, Kolasch & Birch, LLP

(57) ABSTRACT

Provided is an organic EL device having high efficiency and high driving stability while being driven at a low voltage. The organic electroluminescent device includes one or more light-emitting layers between an anode and a cathode opposite to each other. At least one of the light-emitting layers contains a host material and a light-emitting dopant, and (i) a first host formed of an indolocarbazole compound having one or two indolocarbazole rings, and (ii) a second host formed of a carbazole compound having a plurality of carbazole rings and having a bond structure represented by
(Continued)

the following general formula (3) are used as the host material.

10 Claims, 1 Drawing Sheet

(51) Int. Cl.
H01L 51/50 (2006.01)
C07D 209/88 (2006.01)
C07D 405/14 (2006.01)
C07D 487/04 (2006.01)
C09K 11/02 (2006.01)

(52) U.S. Cl.
CPC .......... *C07D 487/04* (2013.01); *C09K 11/025* (2013.01); *C09K 11/06* (2013.01); *H01L 51/0067* (2013.01); *H01L 51/0073* (2013.01); *H01L 51/0074* (2013.01); *H01L 51/0085* (2013.01); *H01L 51/50* (2013.01); *C09K 2211/1029* (2013.01); *C09K 2211/185* (2013.01); *H01L 51/5016* (2013.01); *H01L 2251/5384* (2013.01)

(58) Field of Classification Search
CPC ............. H01L 51/50; H01L 2251/5384; H01L 51/5016; C07D 405/14; C07D 487/04; C07D 209/88; C09K 11/025; C09K 11/06; C09K 2211/185; C09K 2211/1029
See application file for complete search history.

(56) References Cited

U.S. PATENT DOCUMENTS

| | | | |
|---|---|---|---|
| 9,929,353 B2* | 3/2018 | Kottas | C07D 487/06 |
| 2004/0016907 A1 | 1/2004 | Shi | |
| 2009/0302742 A1* | 12/2009 | Komori | C07D 487/04 |
| | | | 313/504 |
| 2010/0187977 A1* | 7/2010 | Kai | C07D 487/04 |
| | | | 313/504 |
| 2011/0062862 A1 | 3/2011 | Yamamoto et al. | |
| 2012/0001158 A1 | 1/2012 | Asari et al. | |
| 2012/0205636 A1 | 8/2012 | Kim et al. | |
| 2012/0223276 A1 | 9/2012 | Parham et al. | |
| 2012/0241732 A1* | 9/2012 | Endo | C09B 57/00 |
| | | | 257/40 |
| 2013/0248845 A1* | 9/2013 | Ogawa | C07D 209/82 |
| | | | 257/40 |
| 2015/0001488 A1 | 1/2015 | Min et al. | |
| 2015/0325796 A1 | 11/2015 | Tada et al. | |

OTHER PUBLICATIONS

Supplementary European Search Report for the Application No. EP 16 772 075.4 dated Oct. 19, 2018.

English Translation of Written Opinion of the International Searching Authority (PCT/ISA/237) for Application No. PCT/JP2016/056643 dated Oct. 12, 2017.

* cited by examiner

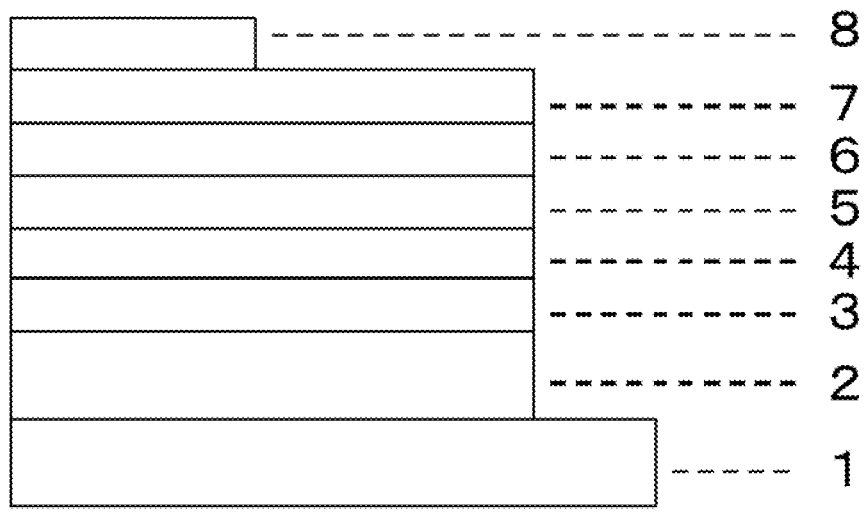

ORGANIC ELECTROLUMINESCENT ELEMENT

TECHNICAL FIELD

The present invention relates to an organic electroluminescent device (hereinafter referred to as "organic EL device"), and more specifically, to an organic EL device having a light-emitting layer containing a host material formed of a plurality of compounds.

BACKGROUND ART

In general, an organic EL device includes a light-emitting layer and a pair of counter electrodes interposing the light-emitting layer therebetween in its simplest structure. That is, the organic EL device uses the phenomenon that, when an electric field is applied between both the electrodes, electrons are injected from a cathode and holes are injected from an anode, and each electron and each hole recombine in the light-emitting layer to emit light as energy.

In recent years, progress has been made in developing an organic EL device using an organic thin film. In order to enhance luminous efficiency particularly, the optimization of the kind of electrodes has been attempted for the purpose of improving the efficiency of injection of carriers from the electrodes. As a result, there has been developed a device in which a hole-transporting layer formed of an aromatic diamine and a light-emitting layer-cum-electron-transporting layer formed of an 8-hydroxyquinoline aluminum complex ($Alq_3$) are formed between electrodes as thin films, resulting in a significant improvement in luminous efficiency, as compared to related-art devices in which a single crystal of anthracene or the like is used. Thus, the development of the above-mentioned organic EL device has been promoted in order to accomplish its practical application to a high-performance flat panel having features, such as self-luminescence and rapid response.

Investigations have also been made on using a phosphorescent light-emitting material rather than a fluorescent light-emitting material as an attempt to raise the luminous efficiency of a device. Many kinds of devices including the above-mentioned device in which a hole-transporting layer formed of an aromatic diamine and a light-emitting layer formed of $Alq_3$ are formed use fluorescent light emission. However, by using phosphorescent light emission, that is, by using light emission from a triplet excited state, luminous efficiency is expected to be improved by about three times to four times, as compared to the case of using related-art devices in which fluorescent light (singlet) is used. In order to accomplish this purpose, investigations have been made on adopting a coumarin derivative or a benzophenone derivative as a light-emitting layer, but extremely low luminance has only been provided. After that, investigations have been made on using a europium complex as an attempt to use a triplet state, but highly efficient light emission has not been accomplished. Among the investigations involving using phosphorescent light emission, many investigations on a phosphorescent light-emitting dopant centered on an organometallic complex, such as an iridium complex, have been made, as disclosed in Patent Literature 1, and ones capable of highly efficient light emission have been found.

CITATION LIST

Patent Literature

[PTL 1] WO 01/041512 A1
[PTL 2] WO 2008/056746 A1
[PTL 3] WO 2011/049325 A2
[PTL 4] WO 2011/057706 A2
[PTL 5] JP 2012-49518 A
[PTL 6] WO 2012/077520 A1
[PTL 7] WO 2009/086028 A2
[PTL 8] WO 2009/136596 A1
[PTL 9] WO 2010/098246 A1
[PTL 10] US 2015/0001488 A1

In Patent Literature 2, there is a disclosure that an indolocarbazole compound is used as a host material. In each of Patent Literatures 3 to 7, there is a disclosure that a carbazole compound is used as a host material. In addition, in each of Patent Literatures 8 and 9, there is a disclosure of a host material obtained by mixing two kinds of indolocarbazole compounds. In Patent Literature 10, there is a disclosure of a host material obtained by mixing a specific indolocarbazole compound and a specific carbazole compound.

However, in each of the literatures, there is not a teaching of the formation of a host material by the mixing of an indolocarbazole compound and a compound obtained by substituting the 4-position of a carbazole compound with the 9-position of carbazole.

SUMMARY OF INVENTION

In order to apply an organic EL device to a display device in a flat panel display or the like, it is necessary to improve the luminous efficiency of the device and also to ensure sufficiently the stability in driving the device. The present invention has an object to provide, in view of the above-mentioned circumstances, a practically useful organic EL device that has high efficiency and high driving stability while being capable of being driven at a low voltage.

The present invention relates to an organic electroluminescent device, including one or more light-emitting layers between an anode and a cathode opposite to each other, in which:

at least one of the light-emitting layers contains a host material containing at least two kinds of host compounds and at least one light-emitting dopant; and the host material contains (i) a compound represented by the following general formula (1) or (2) and (ii) a compound represented by the following general formula (3).

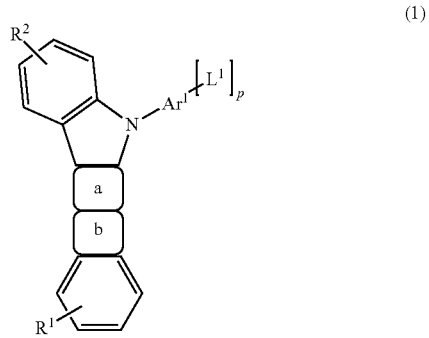

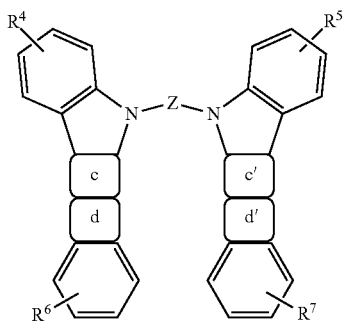

(2)

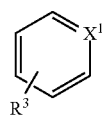

(a1)

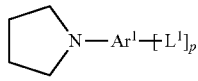

(b1)

In the general formula (1) or (2):

a ring a, a ring c, and a ring c' each independently represent an aromatic ring represented by the formula (a1) that is fused to two adjacent rings at arbitrary positions, and $X^1$ represents C—$R^8$ or N;

a ring b, a ring d, and a ring d' each independently represent a heterocycle represented by the formula (b1) that is fused to two adjacent rings at arbitrary positions;

$Ar^1$'s each independently represent a (p+1)-valent substituted or unsubstituted aromatic hydrocarbon group having 6 to 30 carbon atoms, or a (p+1)-valent substituted or unsubstituted aromatic heterocyclic group having 3 to 16 carbon atoms;

Z represents a divalent substituted or unsubstituted aromatic hydrocarbon group having 6 to 30 carbon atoms, a divalent substituted or unsubstituted aromatic heterocyclic group having 3 to 16 carbon atoms, or a divalent substituted or unsubstituted linked aromatic group obtained by linking 2 to 10 aromatic rings of the groups;

$L^1$'s each independently represent a substituted or unsubstituted aromatic hydrocarbon group having 6 to 30 carbon atoms, a substituted or unsubstituted aromatic heterocyclic group having 3 to 16 carbon atoms, or a substituted or unsubstituted linked aromatic group obtained by linking 2 to 10 aromatic rings of the groups;

p's each independently represent a substitution number and each independently represent an integer of from 0 to 7;

$R^1$ to $R^8$ each independently represent a hydrogen atom, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms; an alkylsulfonyl group having 1 to 20 carbon atoms, an aromatic hydrocarbon group having 6 to 30 carbon atoms, or an aromatic heterocyclic group having 3 to 17 carbon atoms, and in a case of a group except a hydrogen atom, the group may have a substituent, and when any one of $R^1$, $R^2$, and $R^4$ to $R^7$ represents a phenyl group, the phenyl group may form a fused ring with an aromatic ring to be substituted therewith; and in each of $Ar^1$, Z, and $L^1$, when the aromatic hydrocarbon group, the aromatic hydrocarbon group, or the linked aromatic group has a substituent, the substituent includes an alkyl group having 1 to 12 carbon atoms, an alkoxy group having 1 to 12 carbon atoms, or an acyl group having 2 to 13 carbon atoms, and when any one of $R^1$ to $R^8$ has a substituent, the substituent includes an alkyl group having 1 to 12 carbon atoms, an alkoxy group having 1 to 12 carbon atoms, an acyl group having 2 to 13 carbon atoms, an aromatic hydrocarbon group having 6 to 30 carbon atoms, or an aromatic heterocyclic group having 3 to 17 carbon atoms, and a number of substituents may be two or more, and the plurality of substituents may be identical to or different from each other.

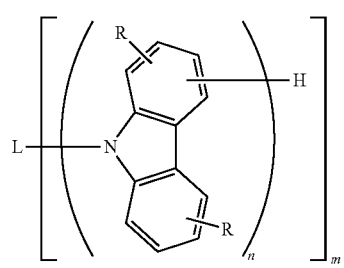

(3)

In the general formula (3):

L represents an m-valent substituted or unsubstituted aromatic hydrocarbon group having 6 to 30 carbon atoms, an m-valent substituted or unsubstituted aromatic heterocyclic group having 3 to 16 carbon atoms, or an m-valent substituted or unsubstituted linked aromatic group obtained by linking 2 to 10 aromatic rings of the groups, provided that L does not represent a group containing a carbazole ring;

R's each independently represent a hydrogen atom, an alkyl group having 1 to 10 carbon atoms, or a cycloalkyl group having 3 to 11 carbon atoms;

m represents a substitution number and represents an integer of from 1 to 3; and n's each represent a number of repetitions and each independently represent an integer of from 1 to 4, provided that at least one n represents an integer of from 2 to 4, and at least one bond structure represented by the formula (c1) is present in the general formula (3).

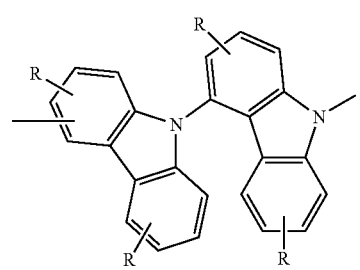

(c1)

In a preferred embodiment, in each of the general formulae (1) and (2), $X^1$ represents C—R, at least one $Ar^1$ represents an aromatic heterocyclic group having 3 to 16 carbon atoms, or Z represents an aromatic heterocyclic group having 3 to 16 carbon atoms.

In a preferred embodiment, in the general formula (3), m represents an integer of 1 or 2, n's each independently represent an integer of from 1 to 3, and at least one n represents an integer of 2 or 3, and all bond structures between carbazolyl groups include bond structures represented by the formula (c1) or by the formula (c1) and the following formula (d1).

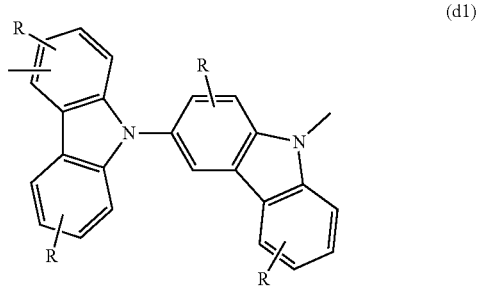

(d1)

In a preferred embodiment, in the general formula (3), L represents an m-valent group produced by removing m hydrogen atoms from a compound represented by any one of the formulae (4) to (7). The m hydrogen atoms are removed from carbon atoms forming an aromatic ring.

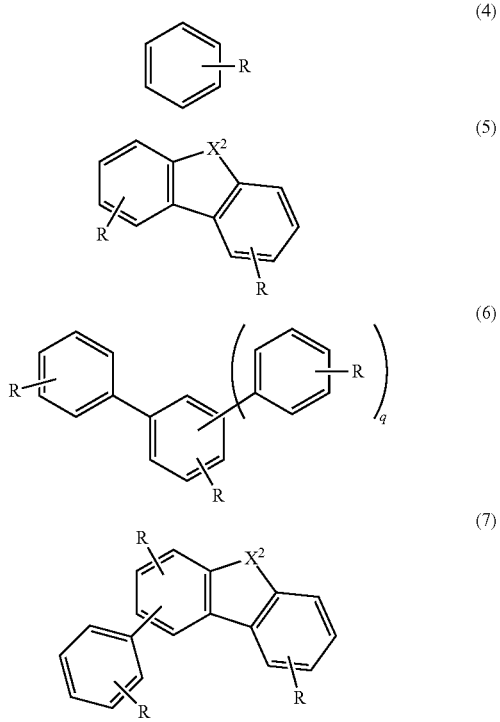

where R's each have the same meaning as R in the general formula (3). $X^2$ represents an oxygen atom or a sulfur atom, and q represents an integer of from 0 to 2.

In addition, the at least two host materials desirably include the compound represented by the general formula (1) and the compound represented by the general formula (3). Further, the light-emitting dopant desirably includes an organometallic complex containing at least one metal selected from ruthenium, rhodium, palladium, silver, rhenium, osmium, iridium, platinum, and gold.

When the two kinds of host materials are preliminarily mixed and are vapor-deposited, a mixing ratio between the two kinds of host materials desirably changes by an amount within 5% relative to a preliminary mixing ratio therebetween before the vapor deposition.

In addition, a difference in vaporization temperature (including evaporation and sublimation) between the compound represented by the general formula (1) or (2) and the compound represented by the general formula (3) is desirably within 30° C., more desirably within 10° C.

In order to improve the characteristics of the device, it is important that the leakage of an exciton and a charge to a peripheral layer be suppressed. The alleviation of the bias of a light-emitting region in a light-emitting layer is effective in suppressing the leakage of the exciton/charge. To that end, the injection amounts of both charges (electron/hole) need to be controlled within preferred ranges.

Here, an indolocarbazole compound has high skeleton stability, and hence its electron/hole-injecting and transporting properties can be controlled to some extent with an isomer or a substituent thereof. However, it is difficult to control the injection amounts of both charges within preferred ranges as described above with the indolocarbazole compound alone. Meanwhile, a specific carbazole compound typified by the general formula (3) has a 4-(9-carbazolyl)carbazole structure. Such a compound formed only of a 3-(9-carbazolyl)carbazole structure as disclosed in Patent Literature 5 has been known as a compound in which a plurality of carbazoles are linked. The carbazole compound to be used in the present invention has the 4-(9-carbazolyl) carbazole structure, and hence may show a hole-transporting property higher than that in the case where a carbazole is linked only at any other position. In addition, when the linking group L is changed into a specific aromatic group, an electron-transporting property is improved while a high hole-transporting property is secured. Accordingly, the charge-injecting and transporting properties of the device can be controlled at high levels. In addition, the carbazole compound has high skeleton stability as in the indolocarbazole compound. Accordingly, in the case where the carbazole compound and the indolocarbazole compound are used as a mixed host, the amounts of both charges to be injected into the light-emitting layer can be precisely regulated, and can be controlled within ranges more preferred than those in the case where each of the compounds is used alone.

The organic EL device of the present invention can achieve a low voltage by using specific compounds as a mixed host. In addition, when the device is a phosphorescent EL device, the device has the lowest excited triplet energy high enough to confine the lowest excited triplet energy (T1 energy). Accordingly, no energy outflow from the inside of a light-emitting layer of the device occurs, and hence high efficiency and a long lifetime can be achieved.

BRIEF DESCRIPTION OF DRAWINGS

FIG. 1 is a schematic sectional view for illustrating an example of an organic EL device.

DESCRIPTION OF EMBODIMENTS

An organic electroluminescent device of the present invention includes, between an anode and a cathode opposite to each other, at least one light-emitting layer containing a host material containing at least two kinds of host compounds and at least one light-emitting dopant. The host material in the light-emitting layer is a mixture containing, as the host compounds, a host material (first host material) selected from compounds each represented by any one of the general formulae (1) and (2) and a host material (second host material) selected from compounds each represented by the general formula (3). The first host material and the second host material may each be a mixture formed of two or more kinds of compounds.

The general formulae (1) and (2) are described below. Symbols common to the general formulae (1) and (2) have the same meaning.

A ring a, a ring c, and a ring c' each represent an aromatic ring (meaning an aromatic hydrocarbon ring or an aromatic heterocycle, or both thereof) represented by the formula (a1) that is fused at arbitrary positions of two adjacent rings. Here, in the formula (a1), $X^1$ represents C—$R^8$ or N, and preferably represents C—$R^8$.

A ring b, a ring d, and a ring d' each represent a heterocycle represented by the formula (b1) that is fused at arbitrary positions of two adjacent rings. Here, the ring c and the ring c', or the ring d and the ring d' may be identical to or different from each other.

The aromatic ring represented by the formula (a1) can be fused to two adjacent rings at arbitrary positions but has a position at which the ring cannot be structurally fused. The aromatic ring represented by the formula (a1) has six sides but is not fused to the two adjacent rings on two adjacent sides. In addition, the heterocycle represented by the formula (b1) can be fused to two adjacent rings at arbitrary positions but has a position at which the heterocycle cannot be structurally fused. That is, the heterocycle has five sides but is not fused to the two adjacent rings on two adjacent sides. In addition, the heterocycle is not fused to any adjacent ring on a side containing a nitrogen atom. Therefore, the number of kinds of the skeletons of the isomers of the compounds represented by the general formulae (1) and (2) is limited.

$Ar^1$'s each independently represent a (p+1)-valent substituted or unsubstituted aromatic hydrocarbon group, or a (p+1)-valent substituted or unsubstituted aromatic heterocyclic group. The number of carbon atoms of the aromatic hydrocarbon group is from 6 to 30, preferably from 6 to 22, more preferably from 6 to 18. The number of carbon atoms of the aromatic heterocyclic group is preferably from 3 to 16.

Specific examples of $Ar^1$ include groups each produced by removing p+1 hydrogen atoms from an aromatic compound, such as benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, a helicene, hexaphene, rubicene, coronene, trinaphthylene, heptaphene, pyranthrene, furan, benzofuran, isobenzofuran, xanthene, oxanthrene, dibenzofuran, peri-xanthenoxanthene, thiophene, thioxanthene, thianthrene, phenoxathiin, thionaphthene, isothianaphthene, thiophthene, thiophanthrene, dibenzothiophene, pyrrole, pyrazole, tellurazole, selenazole, thiazole, isothiazole, oxazole, furazan, pyridine, pyrazine, pyrimidine, pyridazine, triazine, indolizine, indole, isoindole, indazole, purine, quinolizine, isoquinoline, carbazole, imidazole, naphthyridine, phthalazine, quinazoline, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, benzothiazole, benzimidazole, benzoxazole, benzisoxazole, or benzisothiazole. Of those, a group produced by removing p+1 hydrogen atoms from benzene, naphthalene, anthracene, pyridine, pyrazine, pyrimidine, pyridazine, triazine, carbazole, dibenzofuran, dibenzothiophene, quinoline, isoquinoline, quinoxaline, quinazoline, or naphthyridine is preferred.

$L^1$'s each independently represent a substituted or unsubstituted aromatic hydrocarbon group having 6 to 30 carbon atoms, a substituted or unsubstituted aromatic heterocyclic group having 3 to 16 carbon atoms, or a substituted or unsubstituted linked aromatic group obtained by linking 2 to 10 aromatic rings of the groups. $L^1$'s each preferably represent an aromatic hydrocarbon group having 6 to 18 carbon atoms, an aromatic heterocyclic group having 3 to 16 carbon atoms, or a linked aromatic group obtained by linking 2 to 7 aromatic rings of the groups.

Specific examples of $L^1$ include linked aromatic groups each produced by removing one hydrogen atom from an aromatic compound, such as benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, a helicene, hexaphene, rubicene, coronene, trinaphthylene, heptaphene, pyranthrene, furan, benzofuran, isobenzofuran, xanthene, oxanthrene, dibenzofuran, peri-xanthenoxanthene, thiophene, thioxanthene, thianthrene, phenoxathiin, thionaphthene, isothianaphthene, thiophthene, thiophanthrene, dibenzothiophene, pyrrole, pyrazole, tellurazole, selenazole, thiazole, isothiazole, oxazole, furazan, pyridine, pyrazine, pyrimidine, pyridazine, triazine, indolizine, indole, isoindole, indazole, purine, quinolizine, isoquinoline, carbazole, imidazole, naphthyridine, phthalazine, quinazoline, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, benzothiazole, benzimidazole, benzoxazole, benzisoxazole, or benzisothiazole, or an aromatic compound obtained by linking a plurality of aromatic rings of these aromatic compounds.

The term "linked aromatic group" as used herein refers to a group in which a plurality of aromatic rings (meaning an aromatic hydrocarbon ring or an aromatic heterocycle, or both thereof) of aromatic compounds each having a monocyclic structure or a fused ring structure are linked. The phrase "aromatic rings are linked" means that the aromatic rings of aromatic groups are bonded by a direct bond to be linked. When the aromatic rings are substituted aromatic rings, their substituents are not aromatic rings.

The linked aromatic group may be linear or branched, and the aromatic rings to be linked may be identical to or different from each other, may include one or both of an aromatic hydrocarbon ring and an aromatic heterocycle, and may each have a substituent.

When the linked aromatic group is a monovalent group, examples of its linking mode include the following modes.

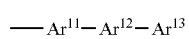
(8)

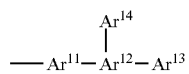
(9)

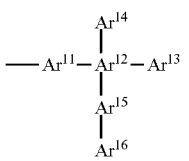
(10)

When the linked aromatic group is a divalent group, examples of its linking mode include the following modes. When the group is a group that is trivalent or more, its linking mode is understood from the foregoing.

(11)

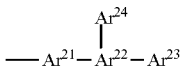
(12)

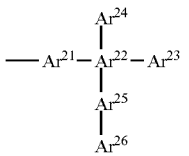
(13)

In the formulae (8) to (13), $Ar^{11}$ to $Ar^{16}$, and $Ar^{21}$ to $Ar^{26}$ each represent a substituted or unsubstituted aromatic ring (aromatic group), and the ring-forming atoms of aromatic rings are bonded by a direct bond. In addition, a bonding hand appears from a ring-forming atom of an aromatic ring. The aromatic ring (aromatic group) means an aromatic hydrocarbon group or an aromatic heterocyclic group, and can be a group that is monovalent or more.

In the formulae (8) to (13), a bonding hand appears from $Ar^{11}$, $Ar^{21}$, or $Ar^{23}$, but can appear from an aromatic ring except the foregoing. In addition, in the case of a group that is divalent or more, two or more bonding hands may appear from one aromatic ring.

Specific examples of the linked aromatic group include groups each produced by removing one or twelve or more hydrogen atoms from an aromatic compound, such as biphenyl, terphenyl, quaterphenyl, bipyridine, bipyrimidine, bitriazine, terpyridine, phenylterphenyl, binaphthalene, phenylpyridine, diphenylpyridine, phenylpyrimidine, diphenylpyrimidine, phenyltriazine, diphenyltriazine, phenylnaphthalene, diphenylnaphthalene, carbazolylbenzene, biscarbazolylbenzene, biscarbazolyltriazine, dibenzofuranylbenzene, bisdibenzofuranylbenzene, dibenzothiophenylbenzene, or bisdibenzothiophenylbenzene.

The description concerning the linked aromatic group is common to linked aromatic groups appearing in descriptions in the general formulae (2) and (3).

In the general formula (2), Z represents a divalent substituted or unsubstituted aromatic hydrocarbon group having 6 to 30 carbon atoms, a divalent substituted or unsubstituted aromatic heterocyclic group having 3 to 16 carbon atoms, or a divalent substituted or unsubstituted linked aromatic group obtained by linking 2 to 10 aromatic rings of the groups. Z preferably represents a divalent aromatic hydrocarbon group having 6 to 18 carbon atoms, a divalent aromatic heterocyclic group having 3 to 16 carbon atoms, or a divalent linked aromatic group obtained by linking 2 to 7 aromatic rings of the groups.

Specific examples of Z include divalent groups each produced by removing two hydrogen atoms from any one of the aromatic compounds listed in the description of $L^1$ or from an aromatic compound in which two or more of the compounds are linked.

In the general formula (1) and the formula (b1), p's each represent a substituent number and each independently represent an integer of from 0 to 7, preferably from 0 to 5, more preferably from 0 to 3. When the formula (b1) is incorporated into the general formula (1) or (2), two $(L)_p$'s are present in the general formula (1), and one $(L')_p$ is present in the general formula (2). When p represents 0, no $L^1$ is present. However, in the general formula (1), when one p represents 0, the other p preferably represents 1 or more.

When any one of $Ar^1$, Z, and $L^1$ represents a substituted aromatic hydrocarbon group, a substituted aromatic heterocyclic group, or a substituted linked aromatic group, its substituent is a group selected from an aliphatic hydrocarbon group having 1 to 12 carbon atoms, an alkoxy group having 1 to 12 carbon atoms, and an acyl group having 2 to 13 carbon atoms. The substituent is preferably an aliphatic hydrocarbon group having 1 to 10 carbon atoms, an alkoxy group having 1 to 10 carbon atoms, or an acyl group having 2 to 11 carbon atoms, and the number of the substituents is desirably from 0 to 5, preferably from 0 to 2. It is not desired that a substituent further have a substituent.

In this description, it is understood that the number of carbon atoms of a substituent is not included in the calculation of the number of carbon atoms. However, the total number of carbon atoms including the number of carbon atoms of a substituent preferably falls within the above-mentioned range of the number of carbon atoms.

Specific examples of the substituent are described below.

The aliphatic hydrocarbon group comes in a saturated alkyl group, an unsaturated alkyl group, and a cyclic alkyl group, and may be linear or branched, and preferred examples thereof include: saturated alkyl groups each having 1 to 10 carbon atoms, such as a methyl group, an ethyl group, a propyl group, an isopropyl group, a butyl group, a t-butyl group, a pentyl group, a hexyl group, and an octyl group; unsaturated alkyl groups each having 2 to 10 carbon atoms, such as an ethenyl group and a propenyl group; and cycloalkyl groups each having 5 to 10 carbon atoms, such as a cyclopentyl group and a cyclohexyl group.

The alkoxy group may be linear or branched, and preferred examples thereof include alkoxy groups each having 1 to 10 carbon atoms, such as a methoxy group, an ethoxy group, a propoxy group, an isopropoxy group, a butoxy group, a t-butoxy group, a pentoxy group, a 2-ethylbutoxy group, a hexyloxy group, and an octoxy group.

The acyl group may be linear or branched, and preferred examples thereof include acyl groups each having 2 to 11 carbon atoms, such as an acetyl group, an ethylcarbonyl group, a propylcarbonyl group, an isopropylcarbonyl group, a butylcarbonyl group, a t-butylcarbonyl group, a pentylcarbonyl group, a 2-ethylbutylcarbonyl group, a hexylcarbonyl group, and an octylcarbonyl group.

In the formulae, $R_1$ to $R_8$ each independently represent a hydrogen atom, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, an aromatic hydrocarbon group having 6 to 30 carbon atoms, or an aromatic heterocyclic group having 3 to 17 carbon atoms. Of those, a hydrogen atom, an alkyl group having 1 to 10 carbon atoms, an aralkyl group having 7 to 24 carbon atoms, an alkoxy group having 1 to 10 carbon atoms, an acyl group having 2 to 11 carbon atoms, a diarylamino group having 12 to 36 carbon atoms, an aromatic hydrocarbon group having 6 to 18 carbon atoms, or an aromatic heterocyclic group having 3 to 16 carbon atoms is preferred, and a hydrogen atom, an aromatic hydrocarbon group having 6 to 18 carbon atoms, or an aromatic heterocyclic group having 3 to 16 carbon atoms is more preferred.

In addition, when any one of $R^1$, $R^2$, and $R^4$ to $R^7$ represents a phenyl group (including a substituted phenyl group), the phenyl group may form a fused ring with an aromatic ring to be substituted therewith.

Specific examples of $R^1$ to $R^8$ in the case where $R^1$ to $R^8$ each represent the alkyl group having 1 to 20 carbon atoms, the aralkyl group having 7 to 38 carbon atoms, the alkenyl group having 2 to 20 carbon atoms, the alkynyl group having 2 to 20 carbon atoms, the dialkylamino group having 2 to 40 carbon atoms, the diarylamino group having 12 to 44 carbon atoms, the diaralkylamino group having 14 to 76 carbon atoms, the acyl group having 2 to 20 carbon atoms, the acyloxy group having 2 to 20 carbon atoms, the alkoxy group having 1 to 20 carbon atoms, the alkoxycarbonyl group having 2 to 20 carbon atoms, the alkoxycarbonyloxy group having 2 to 20 carbon atoms, or the alkylsulfonyl group having 1 to 20 carbon atoms are described below:

methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, phenylmethyl, phenylethyl, phenylicosyl, naphthylmethyl, anthranylmethyl, phenanthrenylmethyl, pyrenylmethyl, vinyl, propenyl, butenyl, pentenyl, decenyl, icosenyl, ethynyl, propargyl, butynyl, pentynyl, decynyl, icosynyl, dimethylamino, ethylmethylamino, diethylamino, dipropylamino, dibutylamino, dipentynylamino, didecylamino, diicosylamino, diphenylamino, naphthylphenylamino, dinaphthylamino, dianthranylamino, diphenanthrenylamino, dipyrenylamino, diphenylmethylamino, diphenylethylamino, phenylmethylphenylethylamino, dinaphthylmethylamino, dianthranylmethylamino, diphenanthrenylmethylamino, acetyl, ethylcarbonyl, propylcarbonyl, isopropylcarbonyl, butylcarbonyl, t-butylcarbonyl, pentylcarbonyl, 2-ethylbutylcarbonyl, hexylcarbonyl, octylcarbonyl, valeryl, benzoyl, acetyloxy, propionyloxy, butyryloxy, valeryloxy, benzoyloxy, methoxycarbonyl, ethoxycarbonyl, propoxycarbonyl, butoxycarbonyl, pentoxycarbonyl, methoxycarbonyloxy, ethoxycarbonyloxy, propoxycarbonyloxy, butoxycarbonyloxy, pentoxycarbonyloxy, methylsulfonyl, ethylsulfonyl, propylsulfonyl, butylsulfonyl, and pentylsulfonyl. Of those, a C1 to C10 alkyl group, such as methyl, ethyl, propyl, butyl, pentyl, hexyl, heptyl, octyl, nonyl, or decyl, a C7 to C20 aralkyl group, such as phenylmethyl, phenylethyl, naphthylmethyl, anthranylmethyl, phenanthrenylmethyl, or pyrenylmethyl, a C1 to C10 alkoxy group, such as methoxy, ethoxy, propoxy, butoxy, pentoxy, hexoxy, heptoxy, octoxy, nonoxy, or decoxy, an acyl group having 2 to 11 carbon atoms, such as acetyl, ethylcarbonyl, propylcarbonyl, isopropylcarbonyl, butylcarbonyl, t-butylcarbonyl, pentylcarbonyl, 2-ethylbutylcarbonyl, hexylcarbonyl, or octylcarbonyl, or a diarylamino group having two C6 to C15 aromatic hydrocarbon groups, such as diphenylamino, naphthylphenylamino, dinaphthylamino, dianthranylamino, or diphenanthrenylamino, is preferred.

Specific examples of $R^1$ to $R^8$ in the case where $R^1$ to $R^8$ each represent the aromatic hydrocarbon group having 6 to 30 carbon atoms or the aromatic heterocyclic group having 3 to 17 carbon atoms include groups each produced by removing a hydrogen atom from an aromatic compound, such as benzene, pentalene, indene, naphthalene, azulene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, furan, benzofuran, isobenzofuran, xanthene, oxanthrene, dibenzofuran, peri-xanthenoxanthene, thiophene, thioxanthene, thianthrene, phenoxathiin, thionaphthene, isothianaphthene, thiophthene, thiophanthrene, dibenzothiophene, pyrrole, pyrazole, tellurazole, selenazole, thiazole, isothiazole, oxazole, furazan, thiadiazole, pyridine, pyrazine, pyrimidine, pyridazine, triazine, indolizine, indole, isoindole, indazole, purine, quinolizine, isoquinoline, carbazole, imidazole, naphthyridine, phthalazine, quinazoline, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, benzothiazole, benzimidazole, benzoxazole, benzisoxazole, or benzisothiazole. Of those, there is preferred a group produced by removing a hydrogen atom from benzene, naphthalene, anthracene, pyridine, pyrazine, pyrimidine, pyridazine, triazine, isoindole, indazole, purine, isoquinoline, imidazole, naphthyridine, phthalazine, quinazoline, benzodiazepine; quinoxaline, cinnoline, quinoline, pteridine, phenanthridine, acridine, perimidine, phenanthroline, phenazine, carboline, indole, carbazole, dibenzofuran, or dibenzothiophene.

When any one of R to $R^8$ represents a group except a hydrogen atom, the group may have a substituent. Examples of the substituent include an aromatic hydrocarbon group having 6 to 30, preferably 6 to 18 carbon atoms, and an aromatic heterocyclic group having 3 to 17, preferably 3 to 15 carbon atoms in addition to the same examples as those of the substituent in the case where any one of $Ar^1$, Z, and $L^1$ described above represents a substituted aromatic hydrocarbon group or a substituted aromatic heterocyclic group. The number of substituents is preferably from 0 to 3, more preferably from 0 to 2 per any one of $R^1$ to $R^8$.

Preferred specific examples of the compounds represented by the general formulae (1) and (2) are shown below, but the compounds are not limited thereto.

1-1
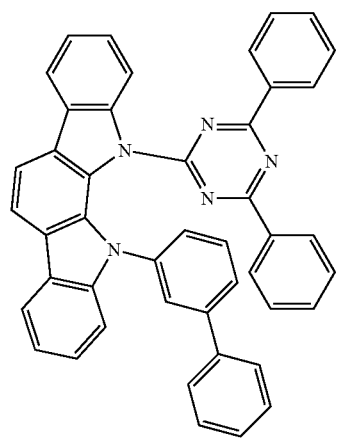
1-2
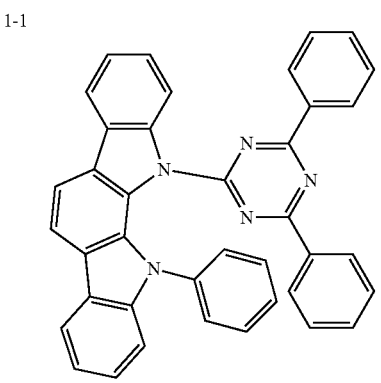
1-3
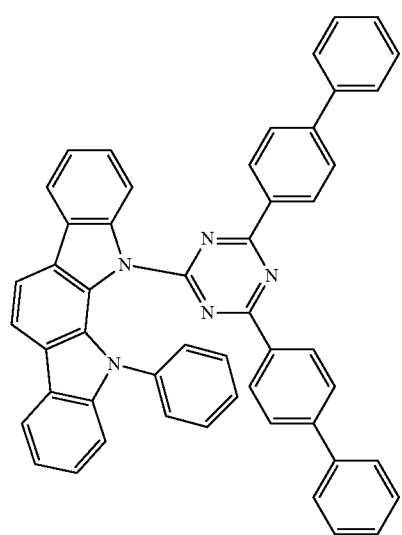
1-4
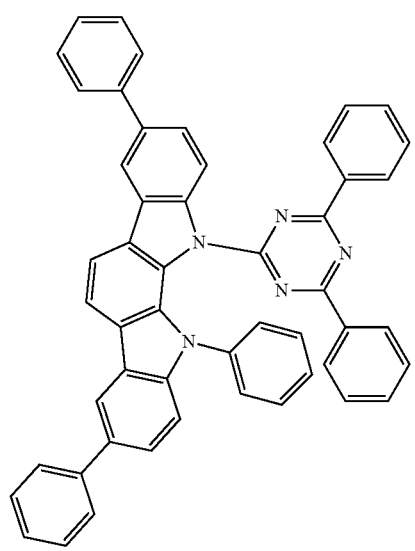
1-5
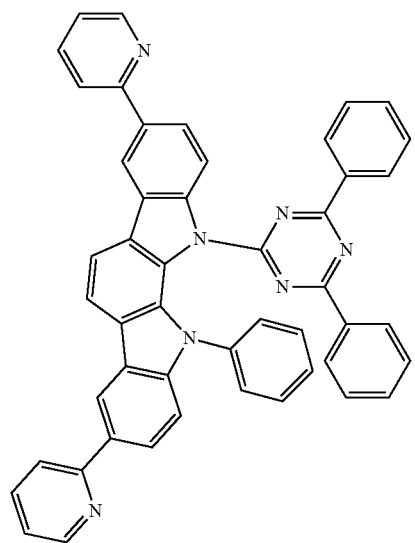
1-6
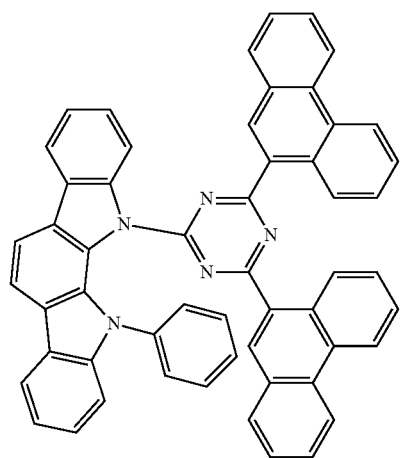

-continued
1-7
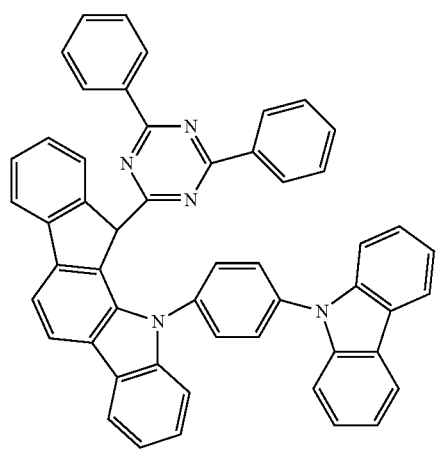
1-8
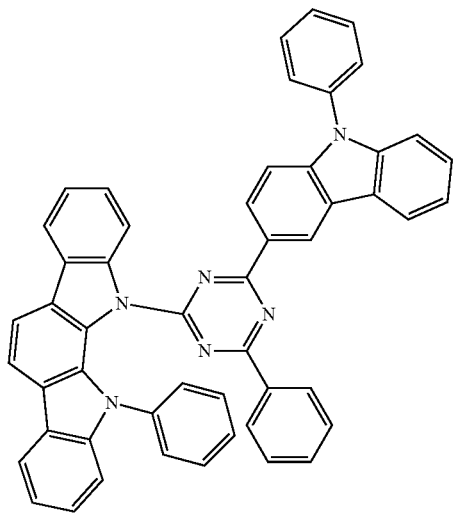
1-9
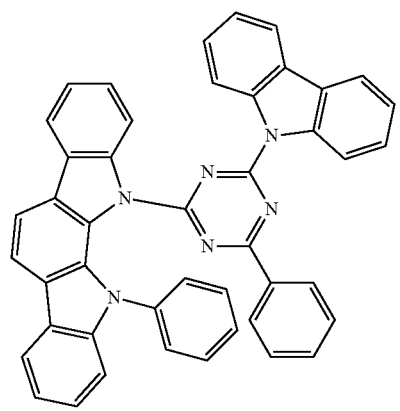
1-10
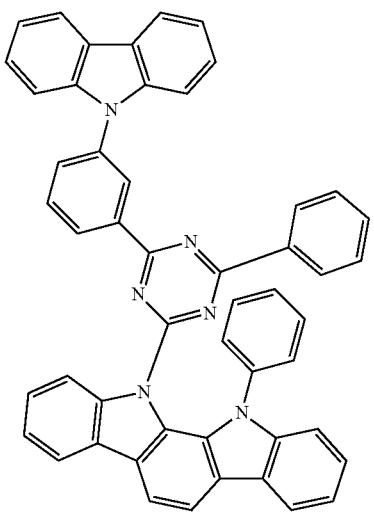
1-11
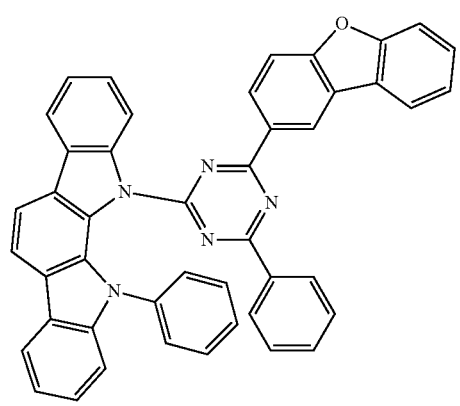
1-12
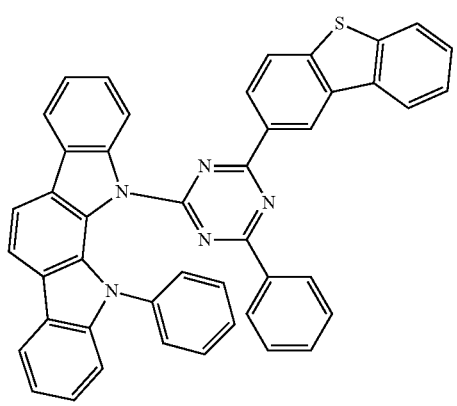

-continued
1-13
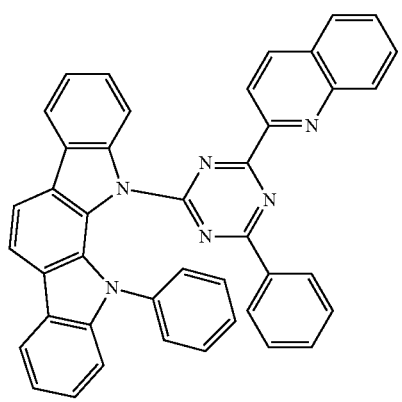
1-14
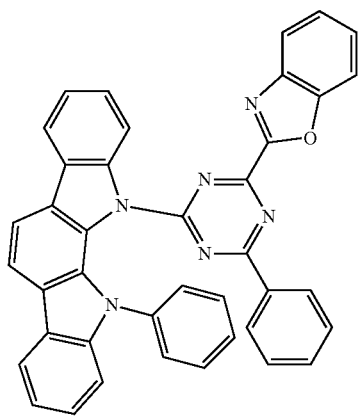
1-15
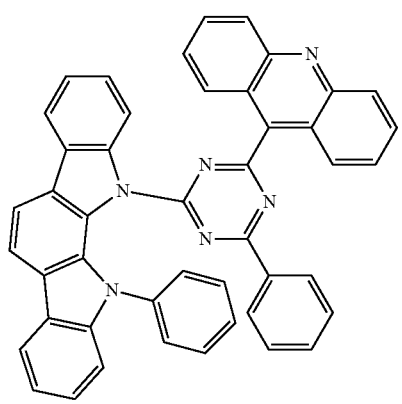
1-16
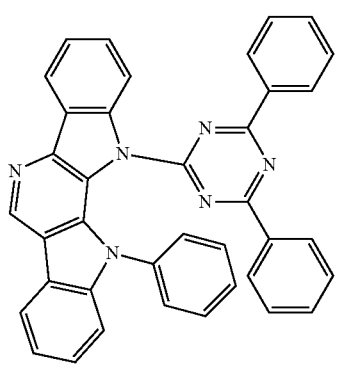
1-17
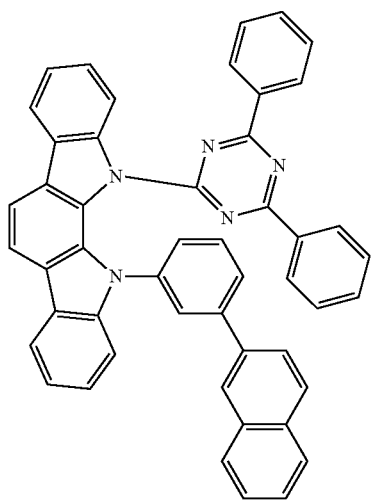
1-18
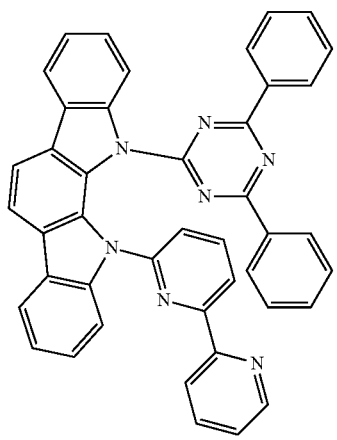

-continued
1-19
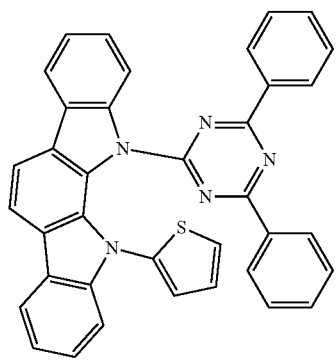
1-20
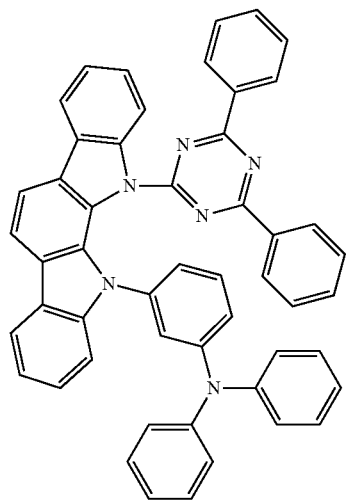
1-21
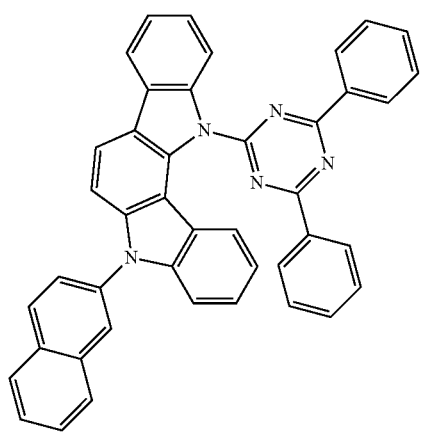
1-22
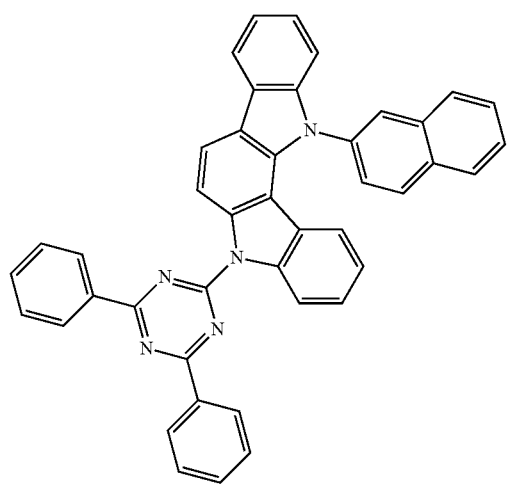
1-23
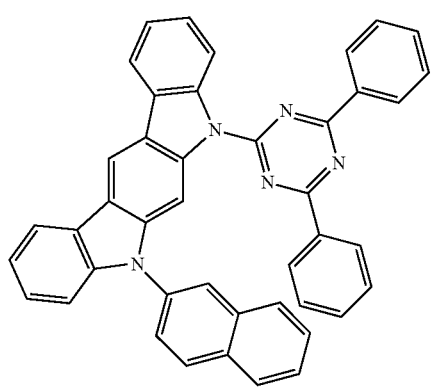
1-24
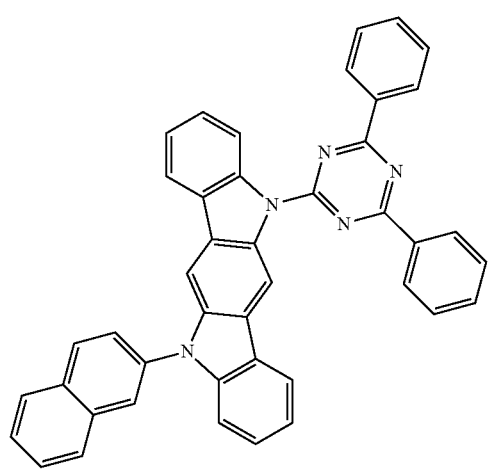

-continued
1-25
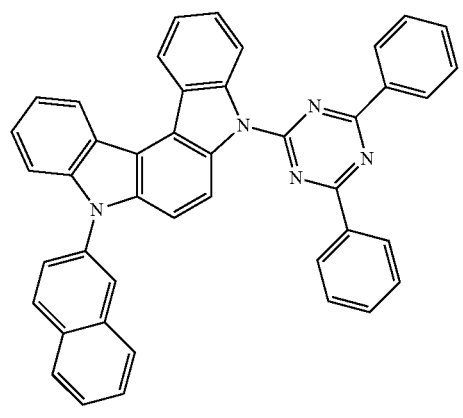
1-26
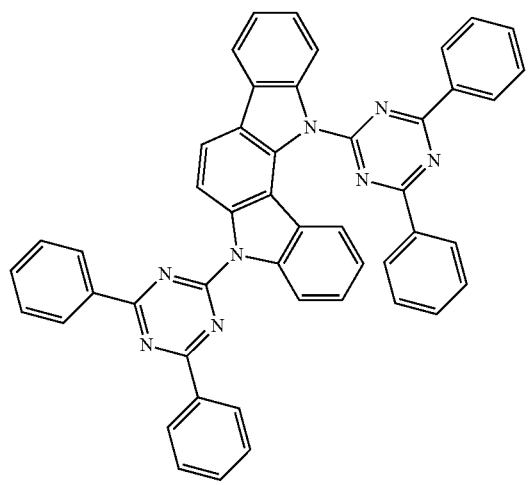
1-27
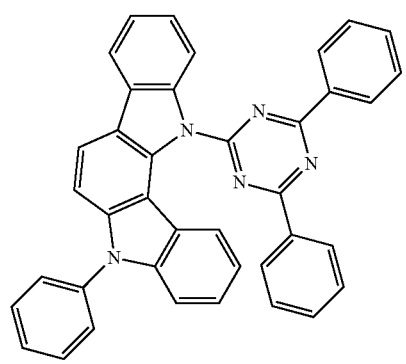
1-28
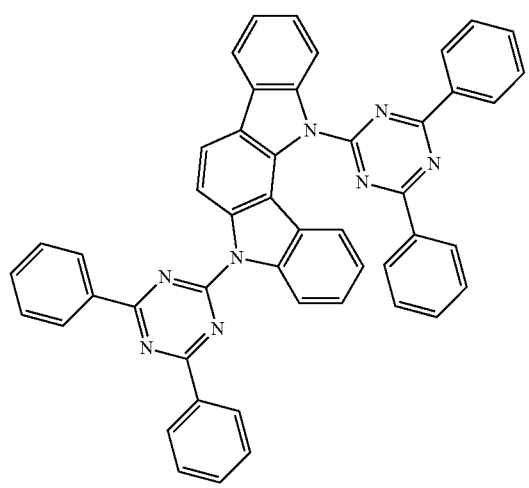
1-29
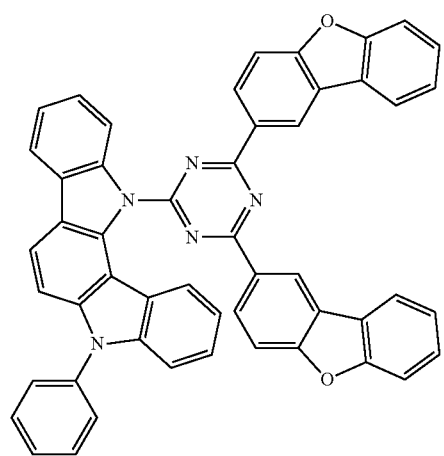
1-30
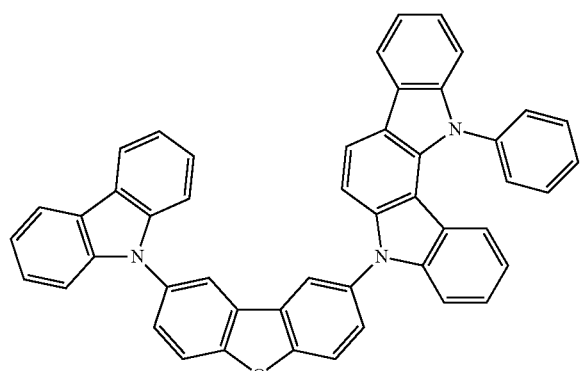

-continued
1-31
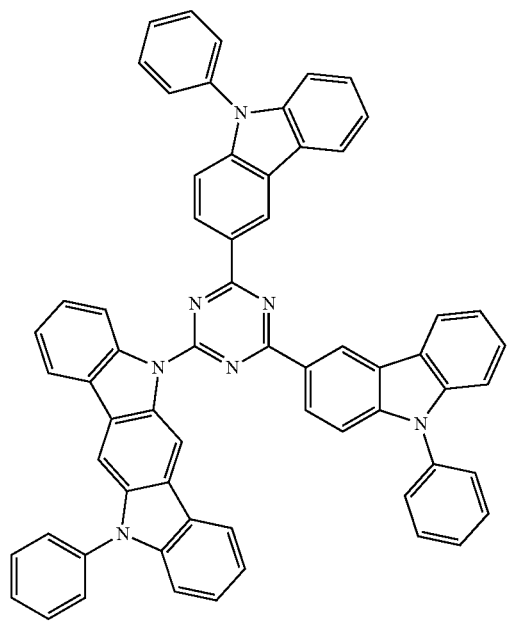
1-32
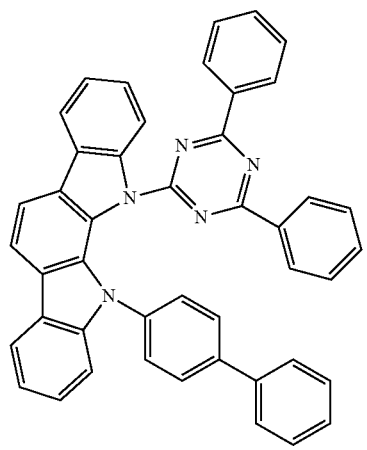
1-33
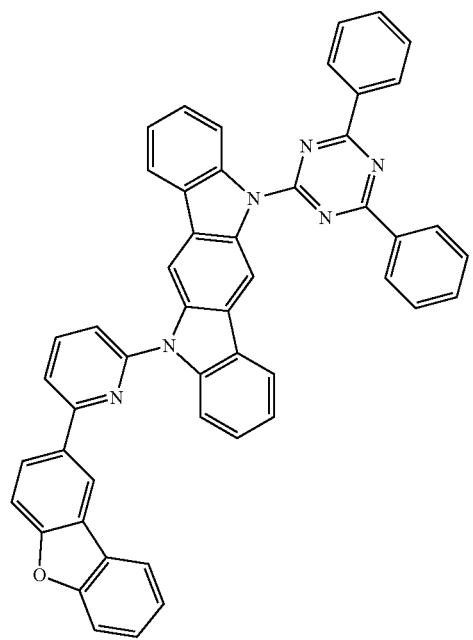
1-34
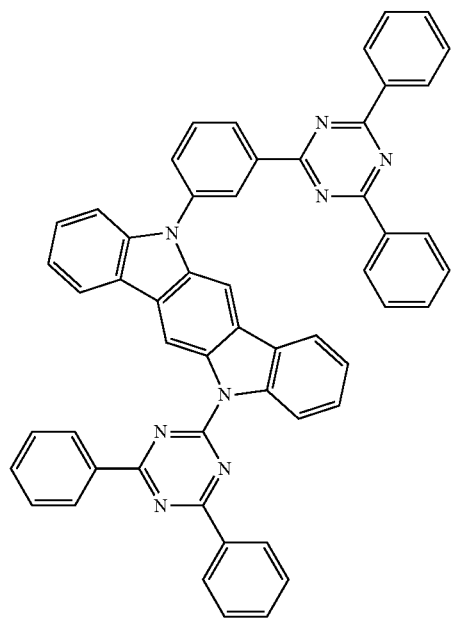

-continued
1-35
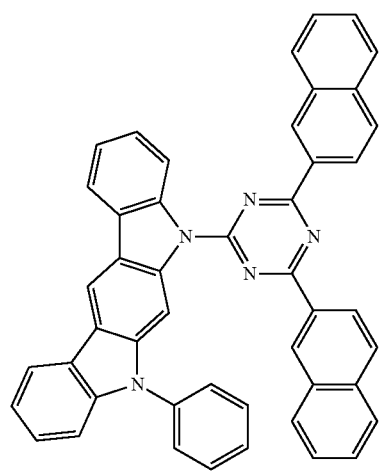
1-36
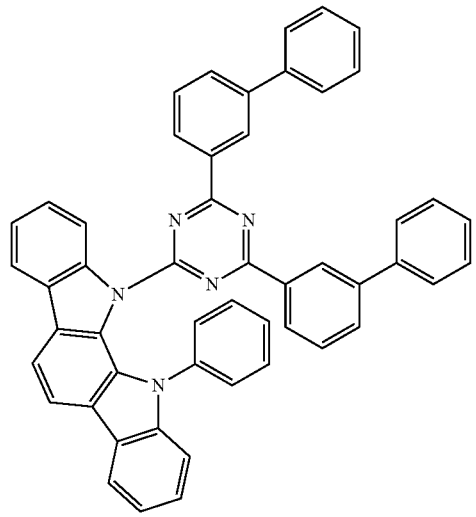
1-37
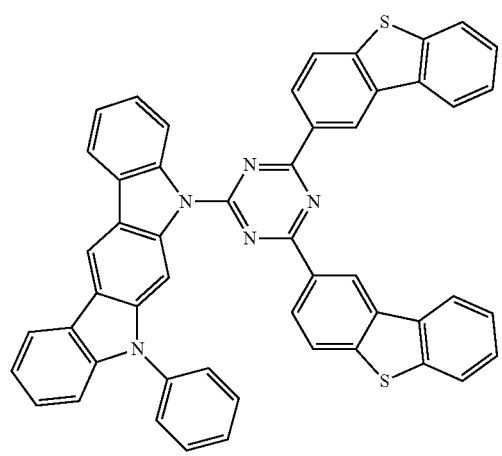
1-38
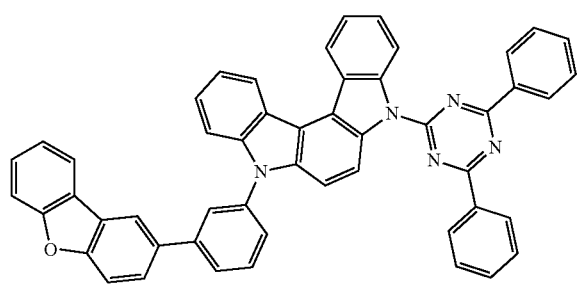
1-39
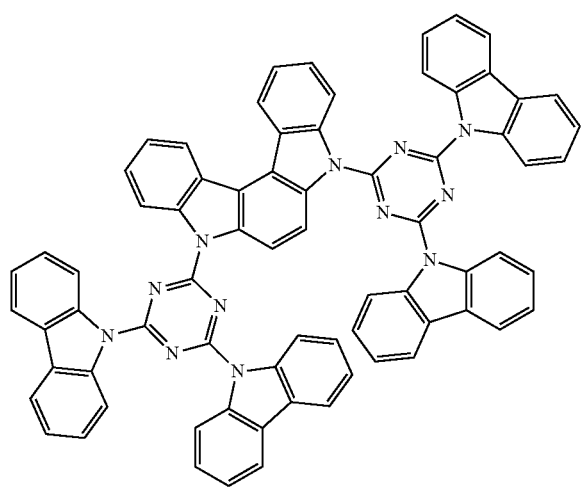
1-40
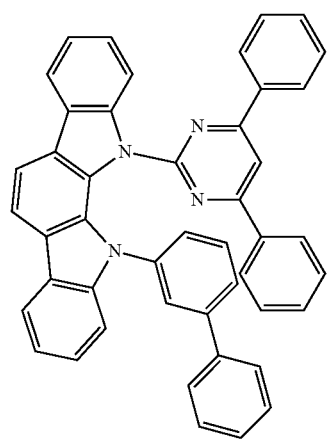

-continued
1-41
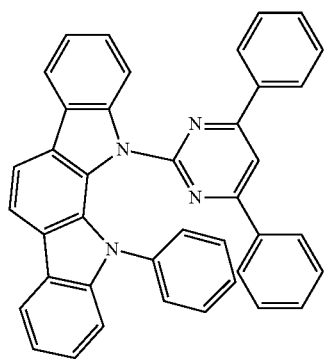
1-42
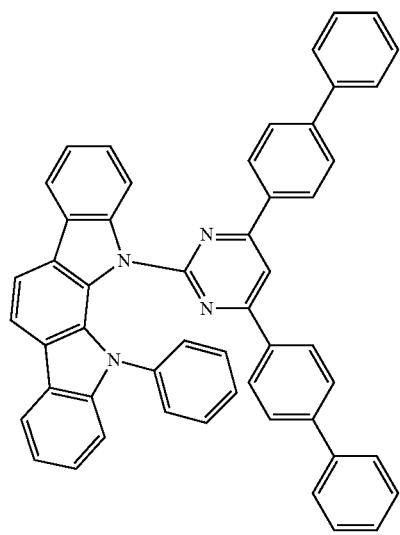
1-43
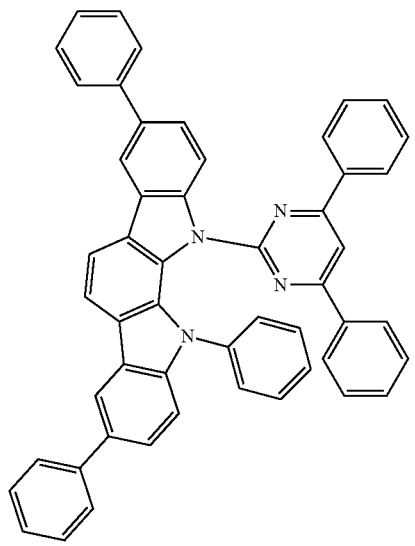
1-44
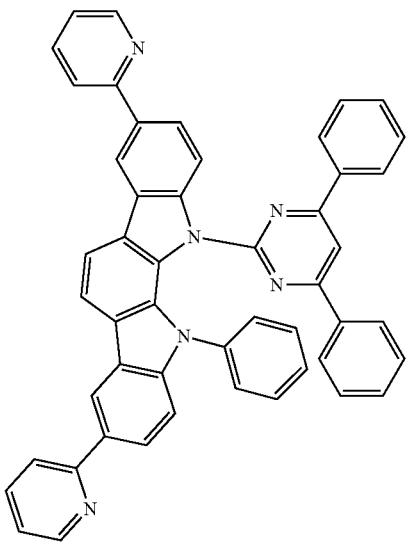
1-45
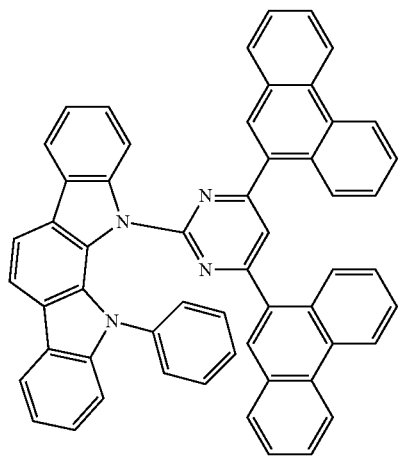
1-46
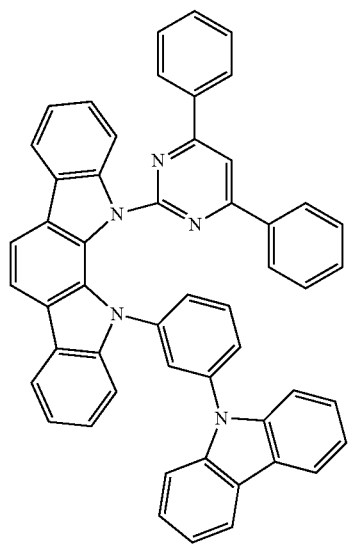

-continued
1-47
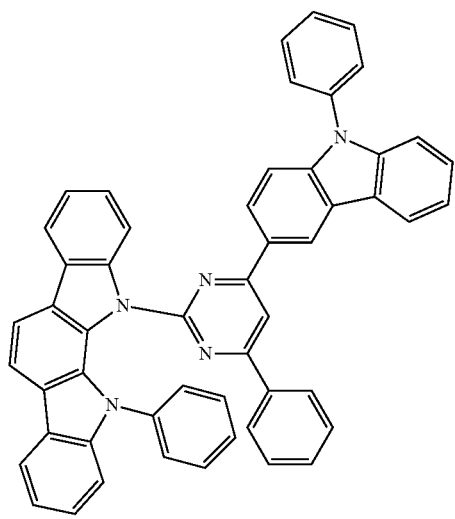
1-48
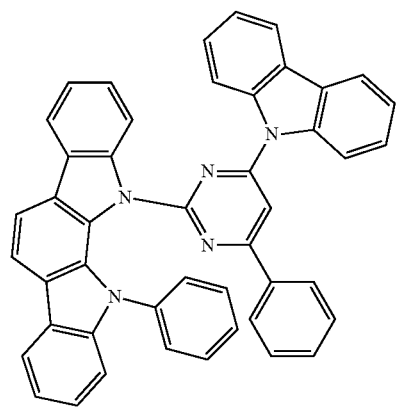
1-49
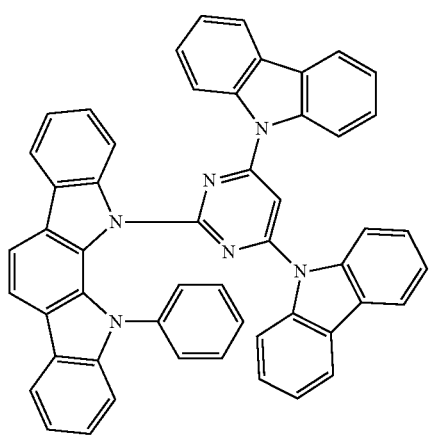
1-50
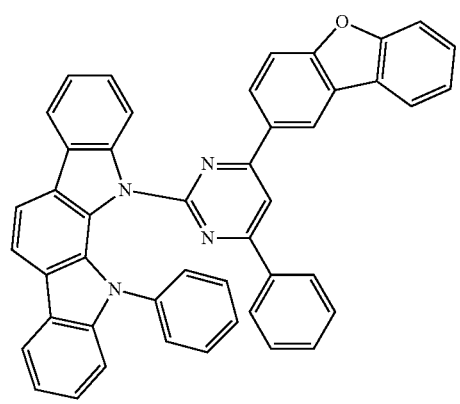
1-51
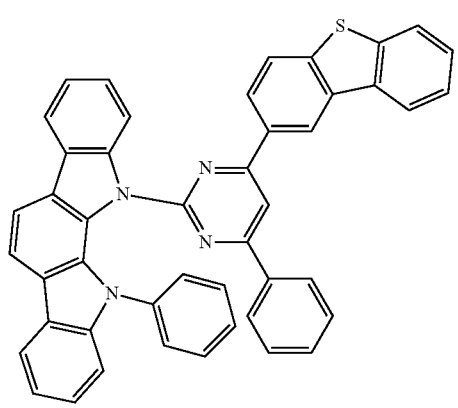
1-52
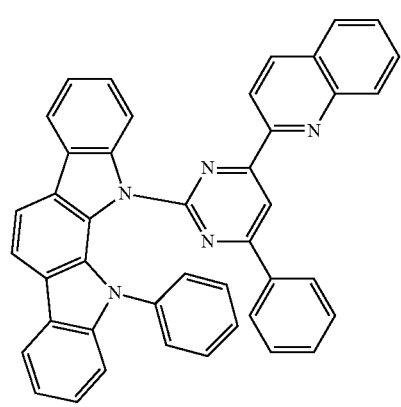

-continued
1-53
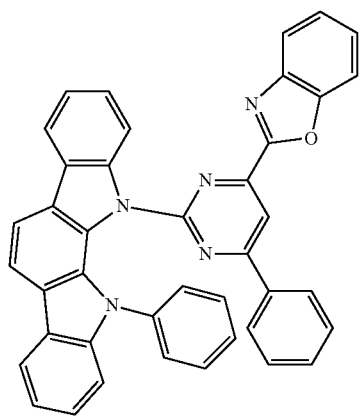
1-54
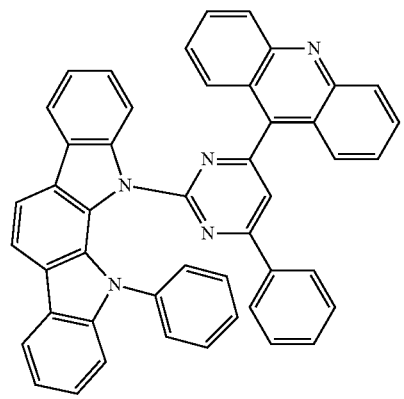
1-55
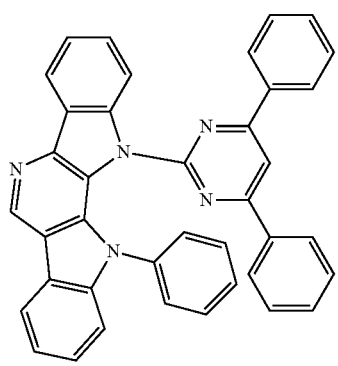
1-56
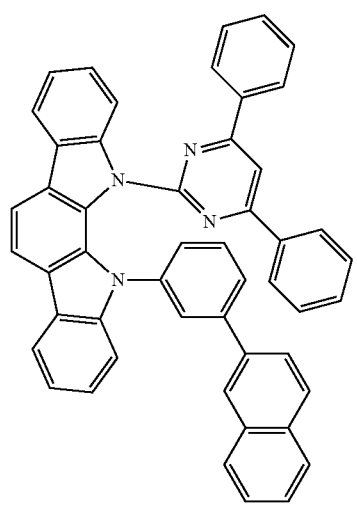
1-57
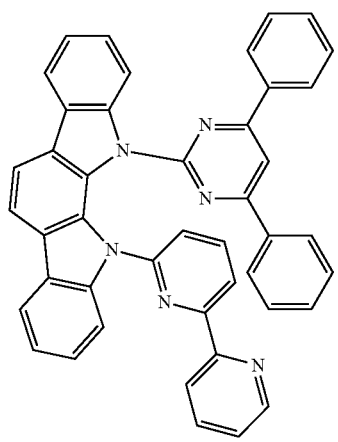
1-58
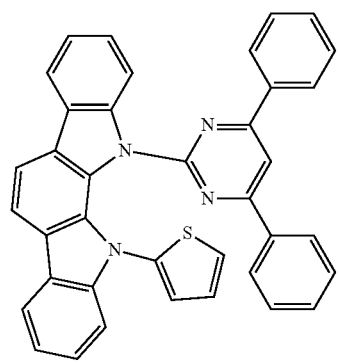

-continued
1-59
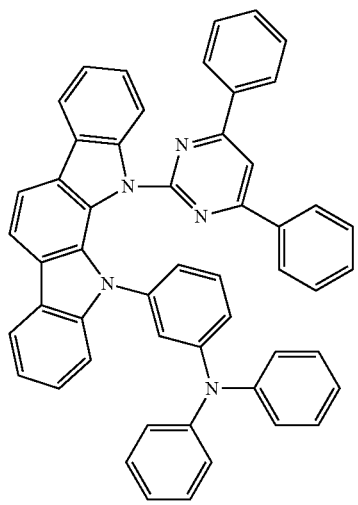
1-60
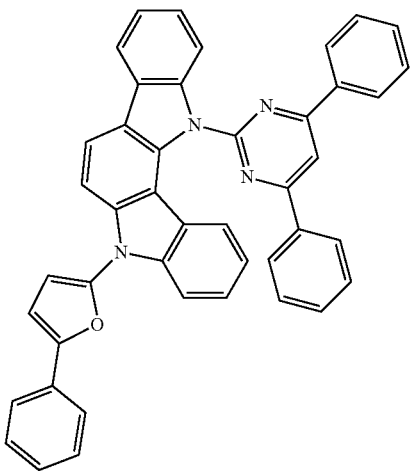
1-61
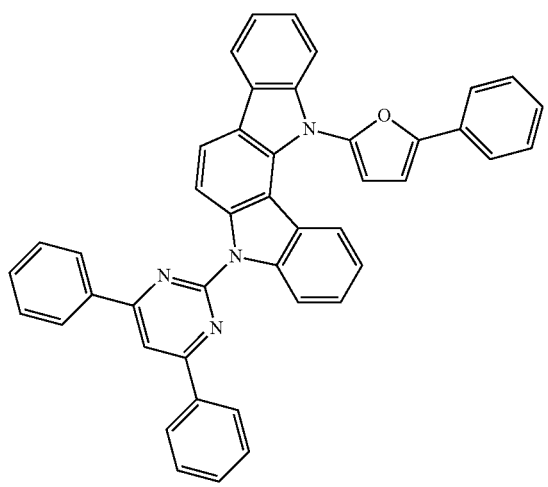
1-62
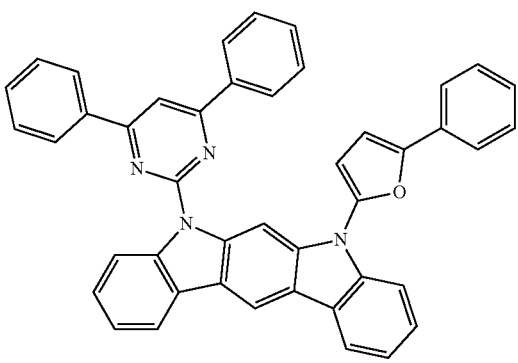
1-63
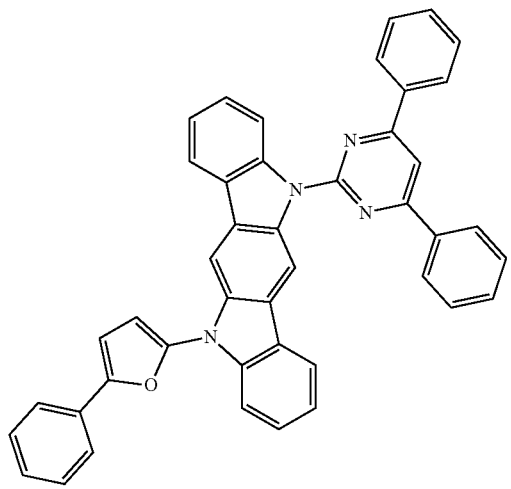
1-64
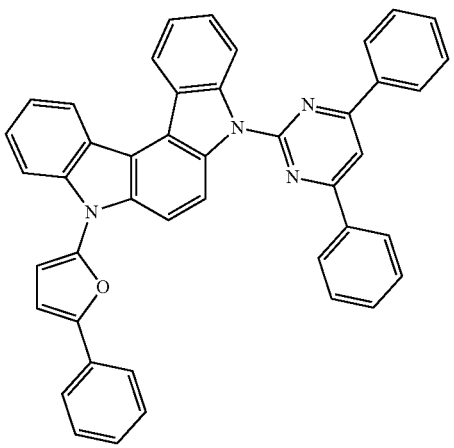

-continued
1-65
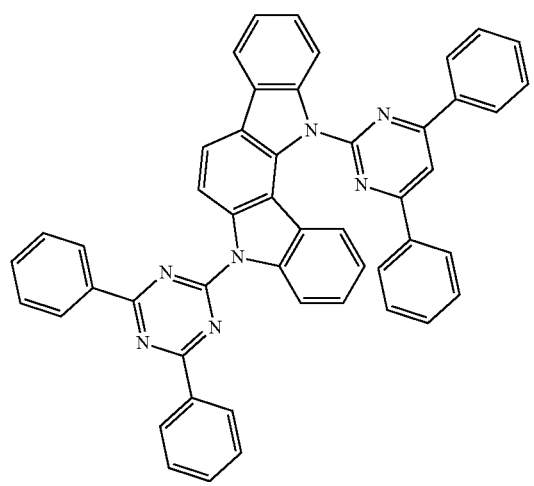
1-66
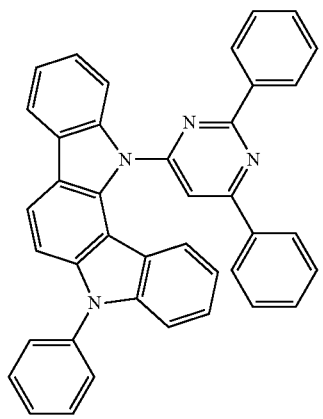
1-67
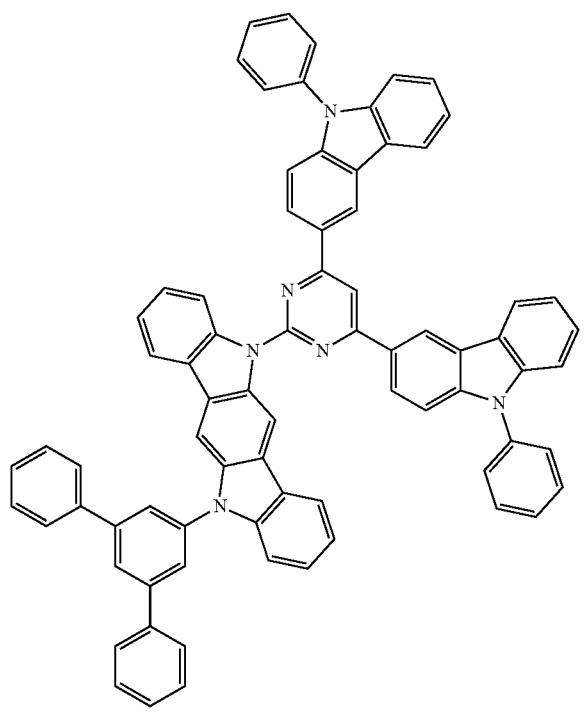
1-68
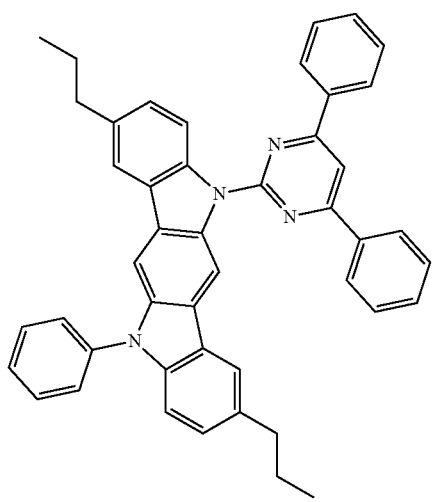

-continued
1-69
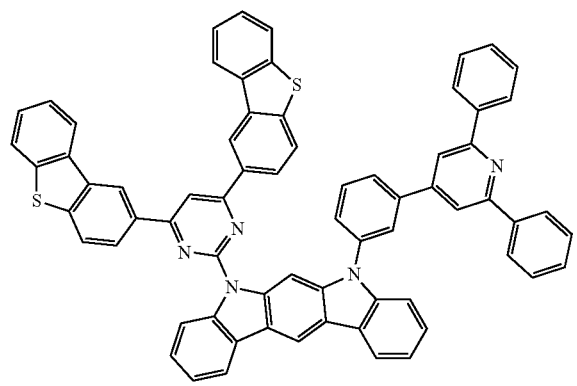
1-70
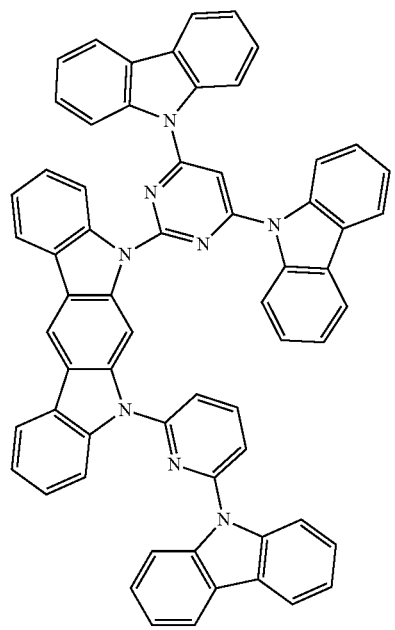
1-71
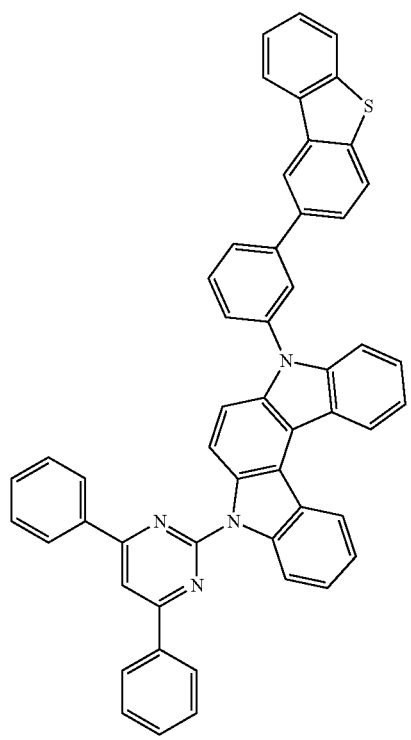
1-72
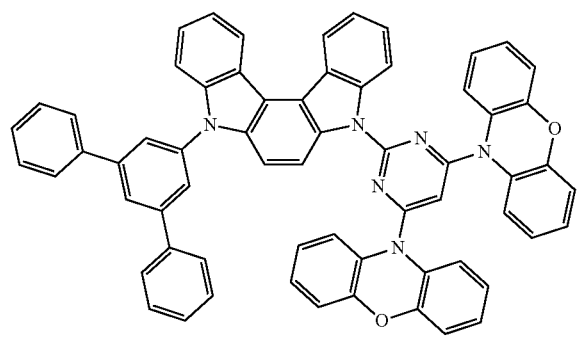

-continued
1-72A
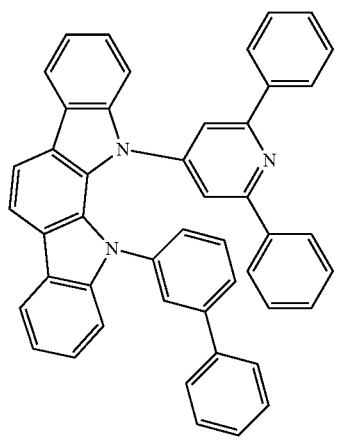
1-73
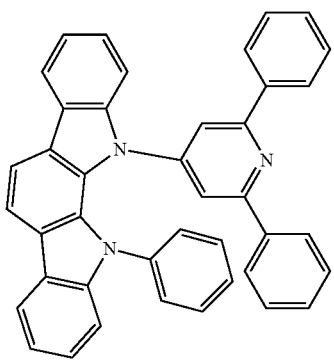
1-74
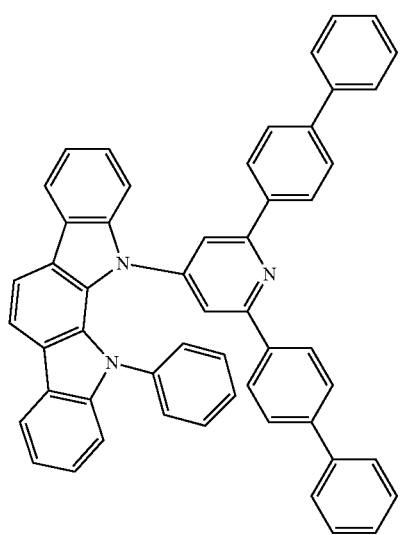
1-75
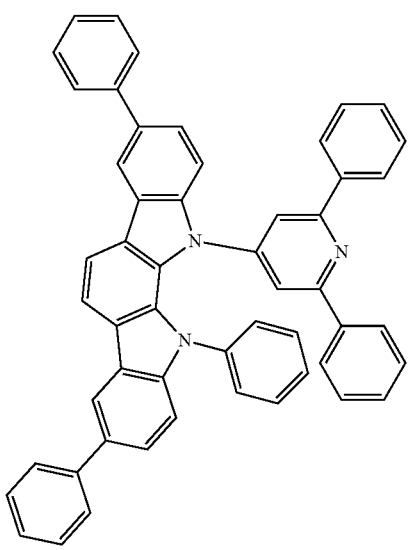
1-76
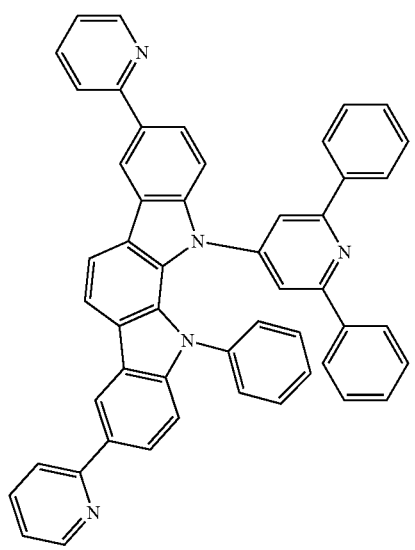
1-77
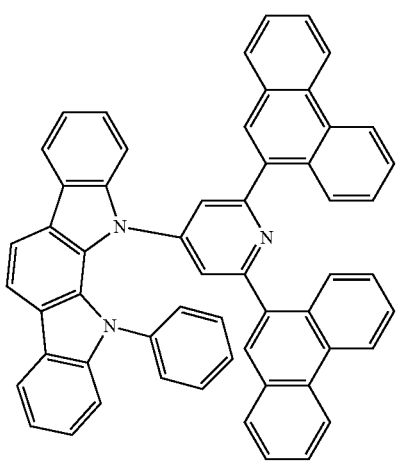

1-78
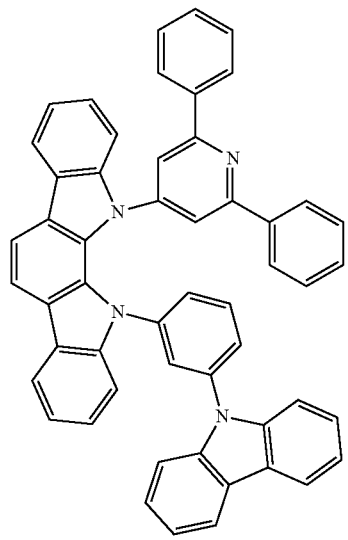
1-79
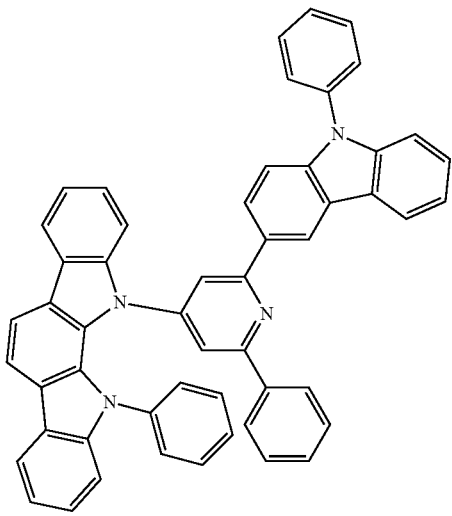
1-80
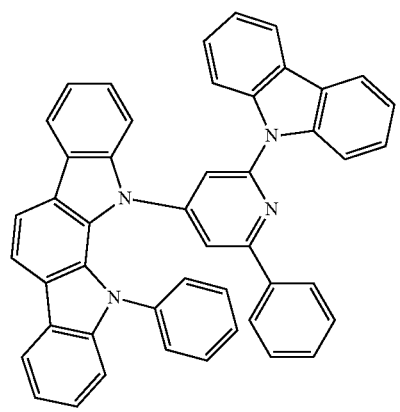
1-81
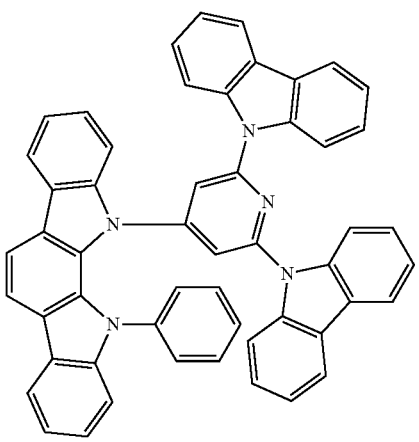
1-82
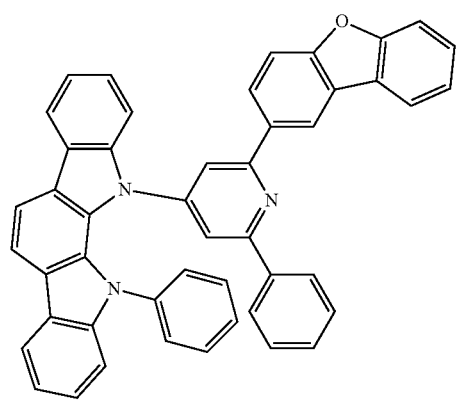
1-83
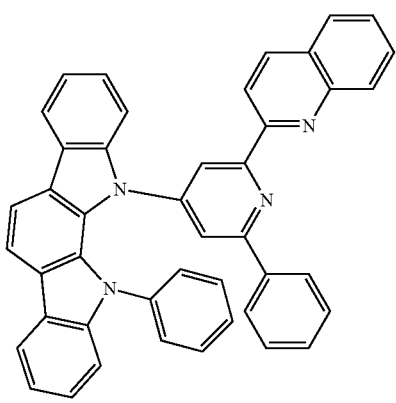

-continued
| 1-84 | 1-85 |
|---|---|
| 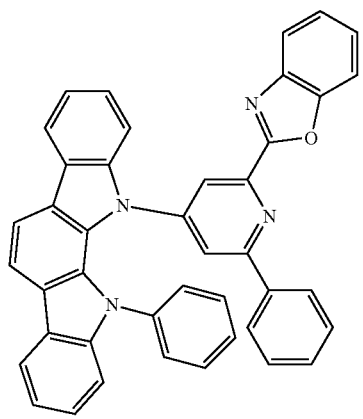 | 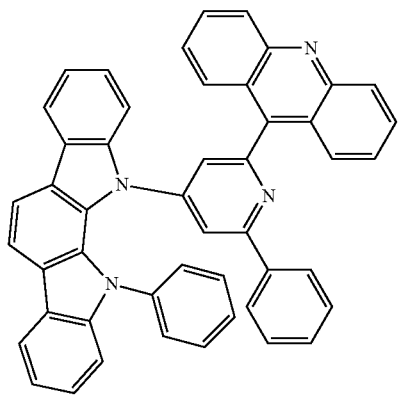 |
| 1-86 | 1-87 |
| 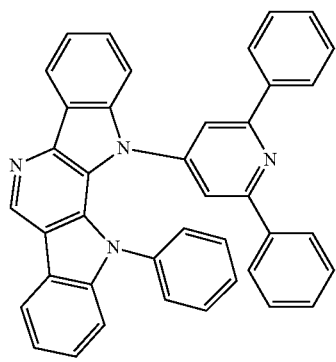 | 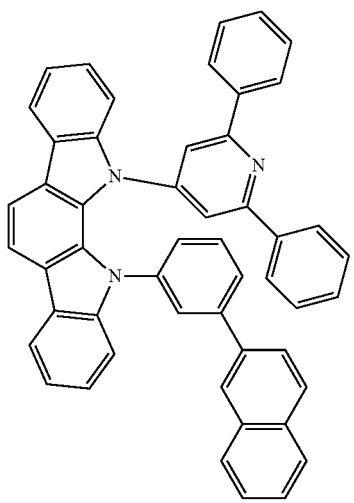 |
| 1-88 | 1-89 |
| 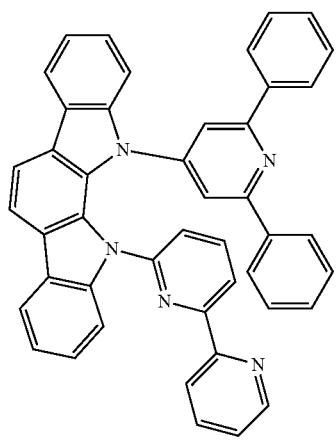 | 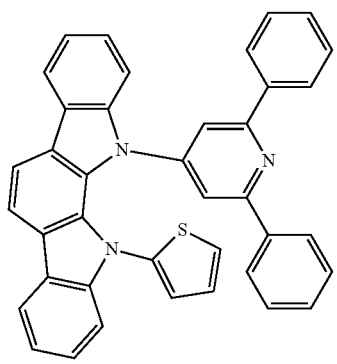 |

-continued
1-90
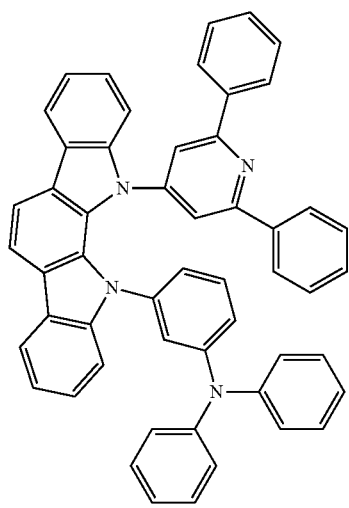
1-91
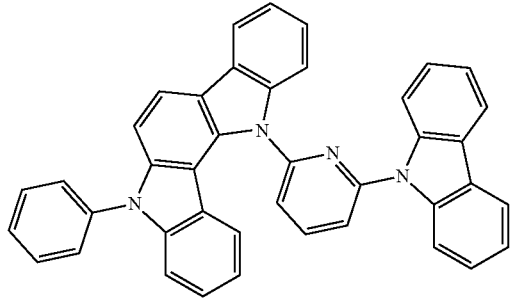
1-92
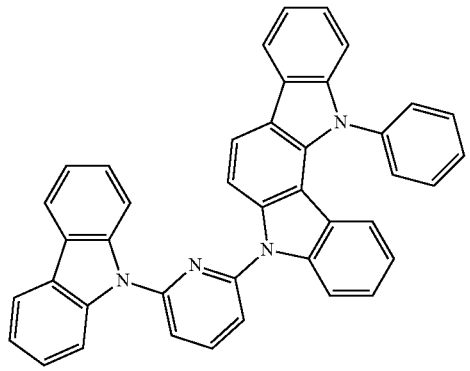
1-93
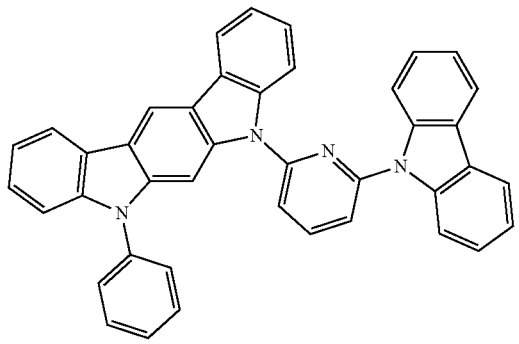
1-94
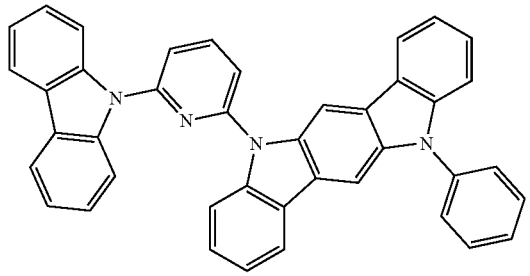
1-95
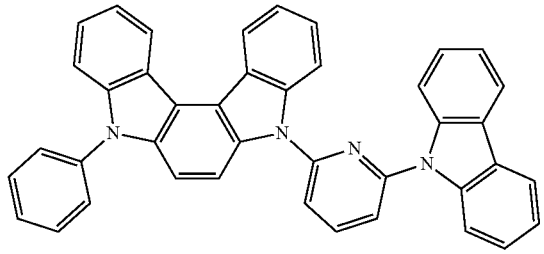
1-96
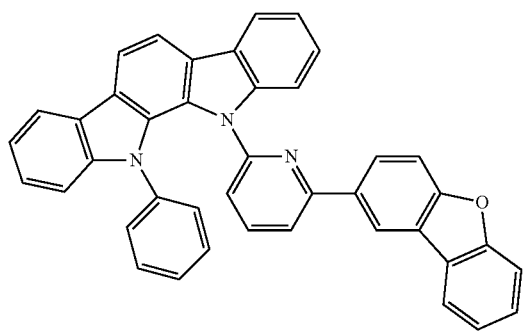
1-97
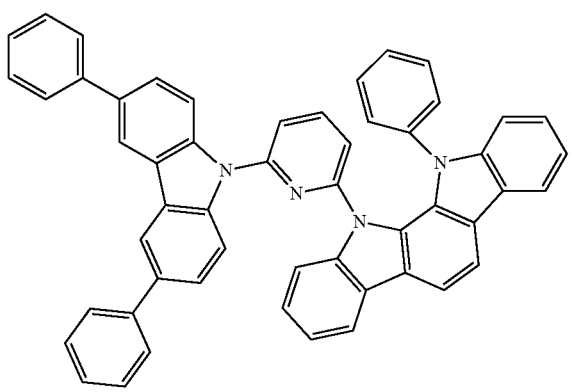

1-98
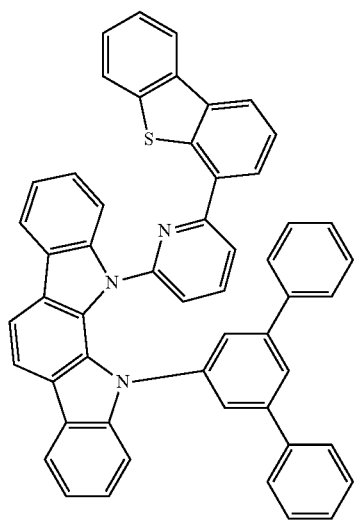
1-99
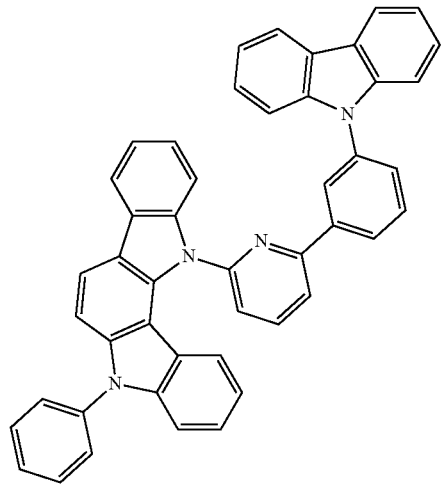
1-100
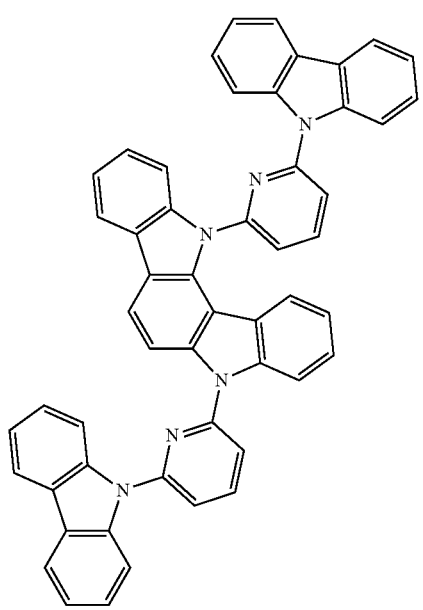
1-101
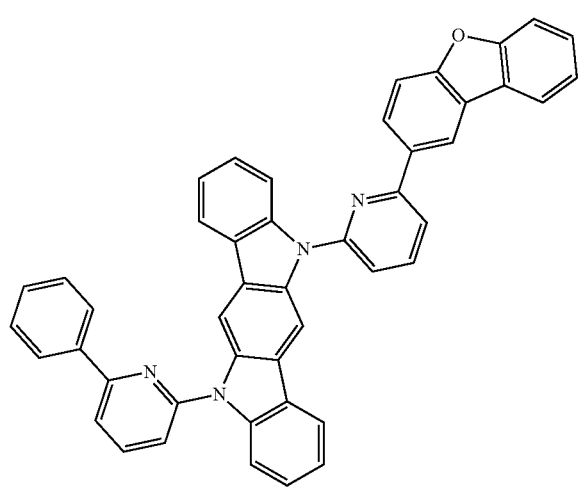

-continued
1-102
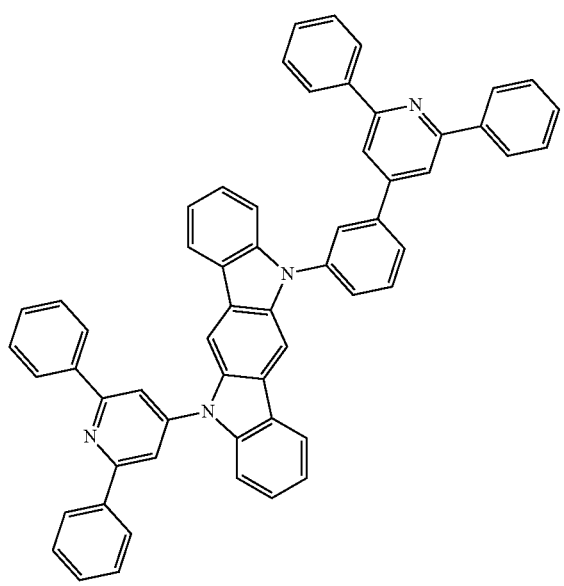
1-103
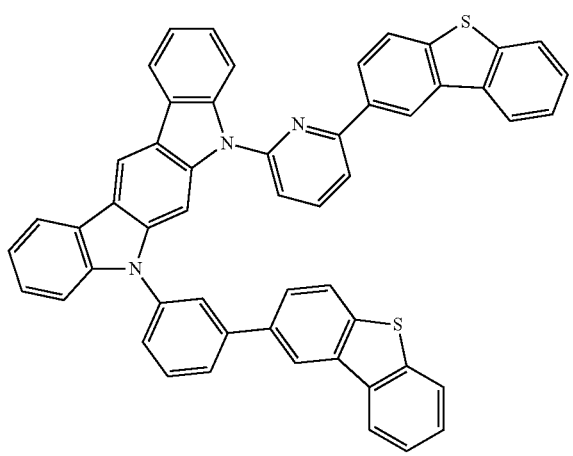
1-104
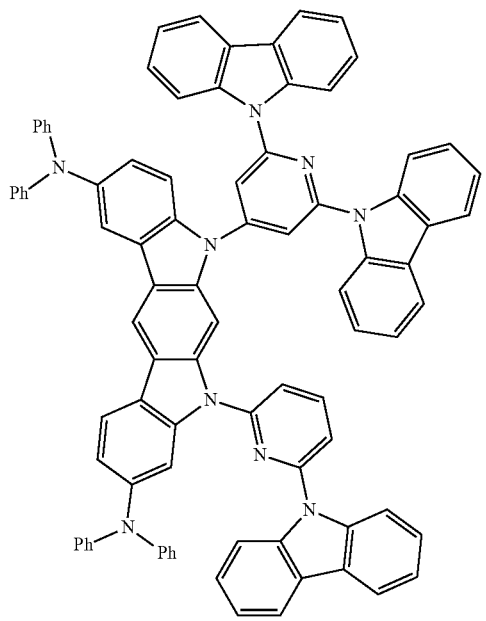
1-105
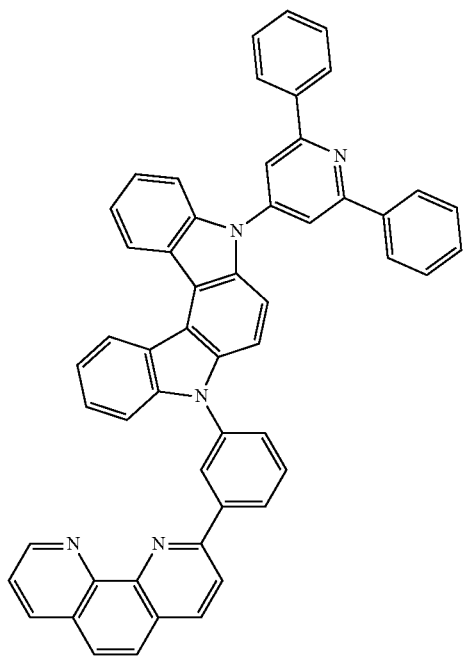

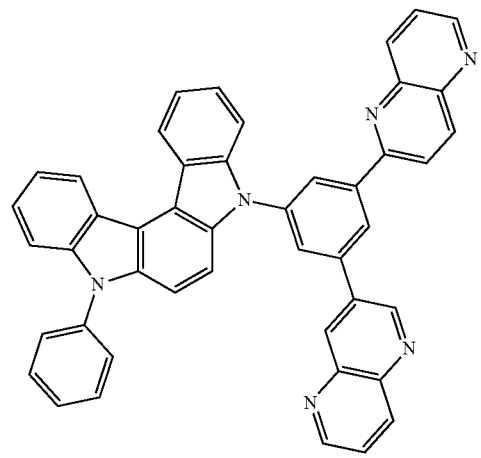
1-106
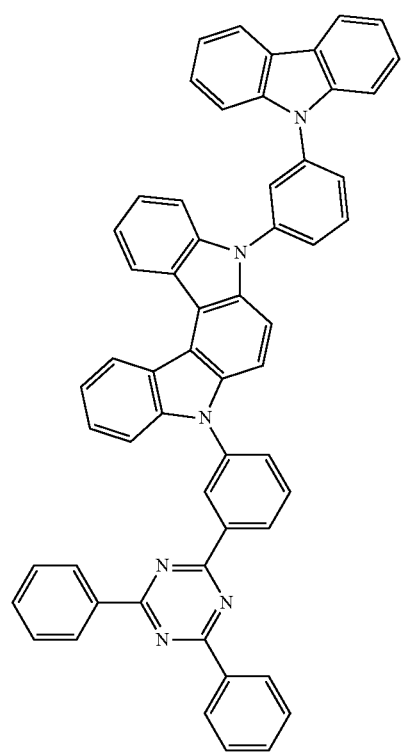
1-107
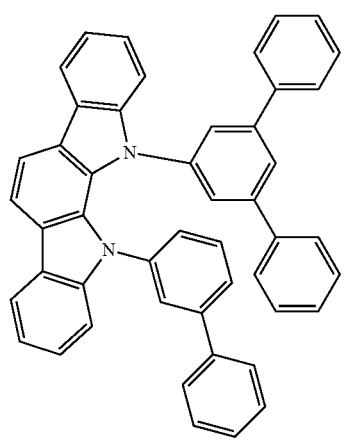
1-108

-continued
1-109
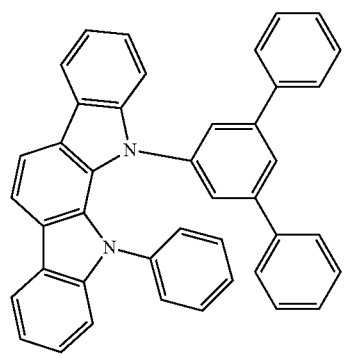
1-110
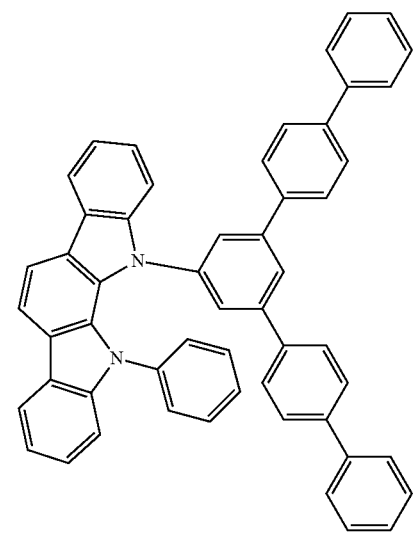
1-111
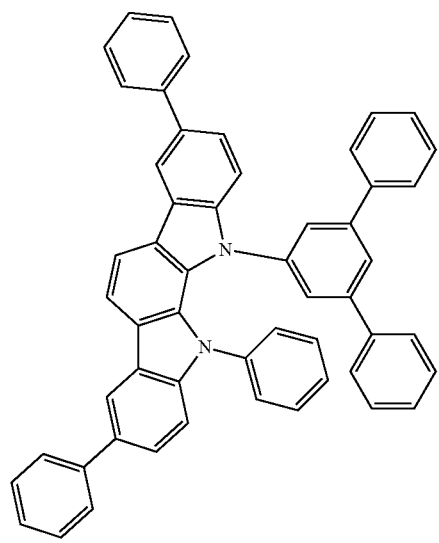
1-112
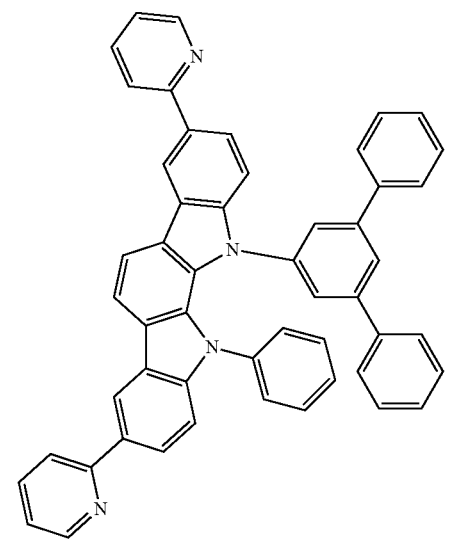
1-113
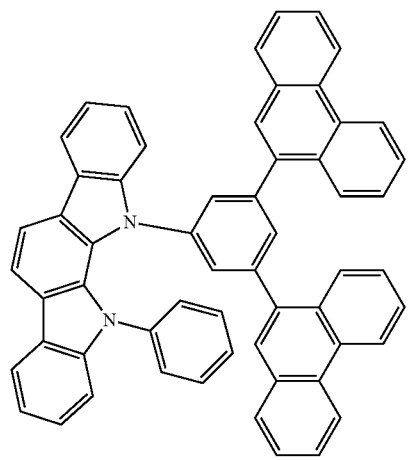
1-114
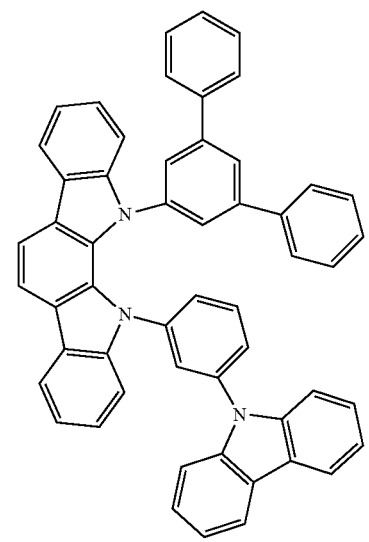

-continued
1-115
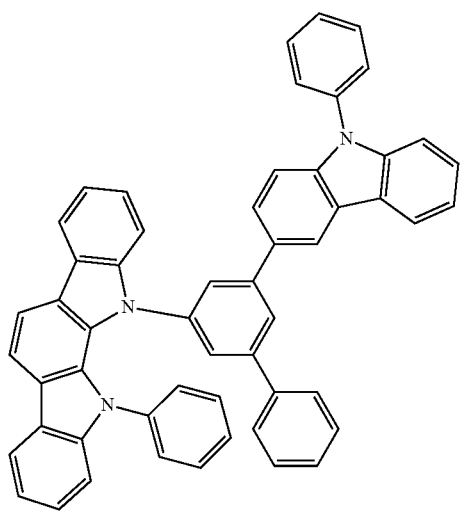
1-116
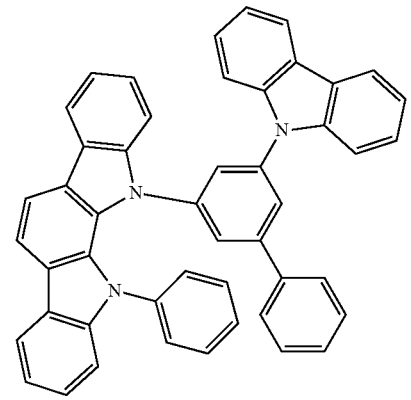
1-117
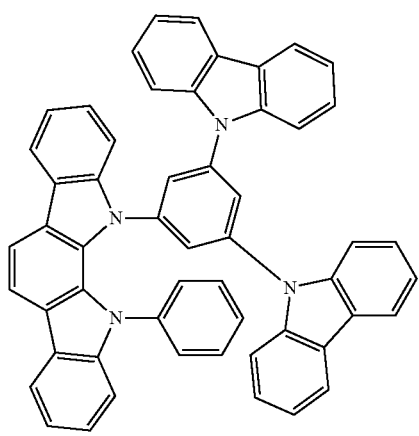
1-118
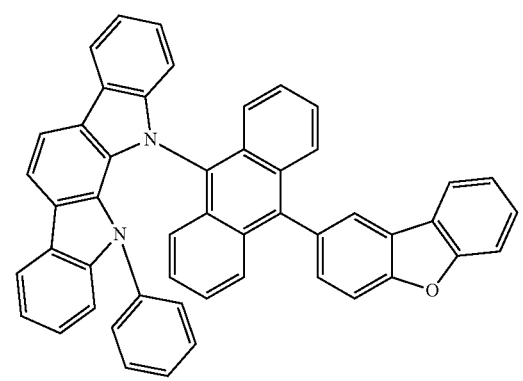
1-119
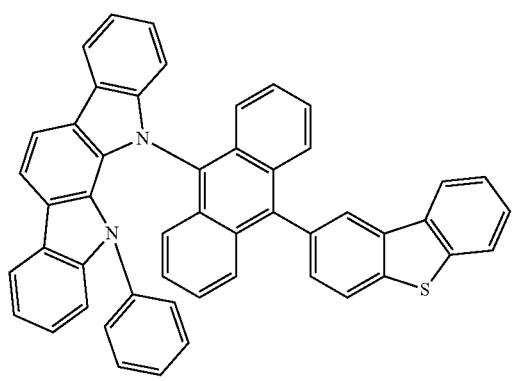
1-120
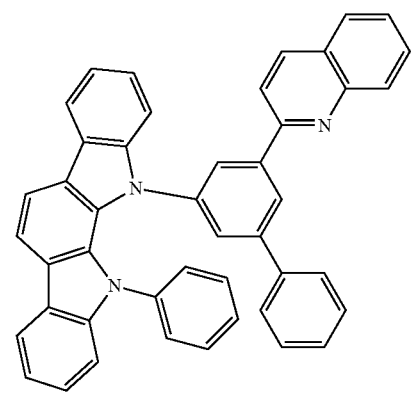

-continued
1-121
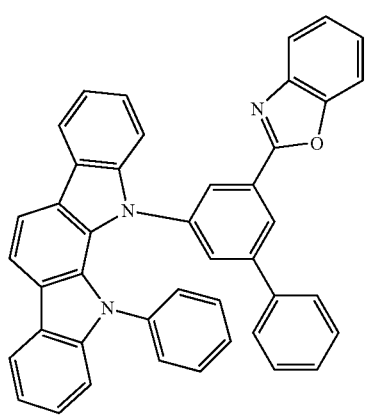
1-122
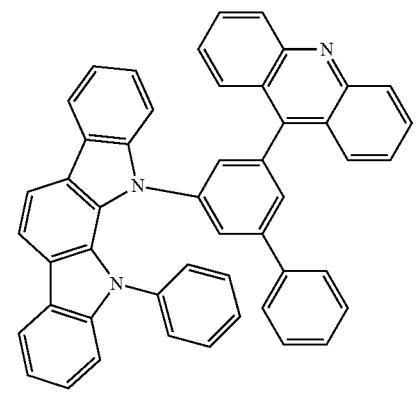
1-123
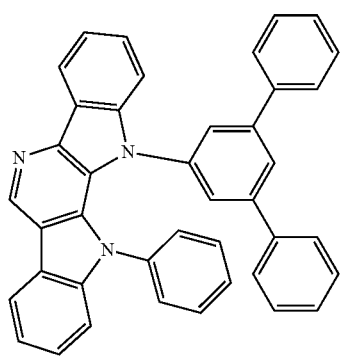
1-124
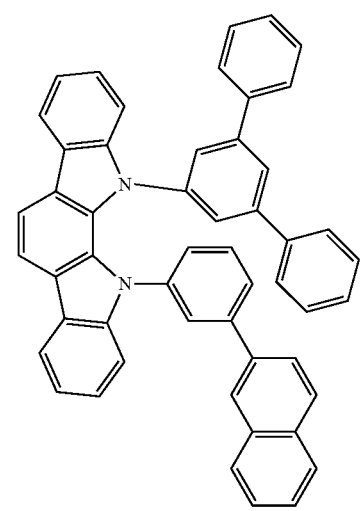
1-125
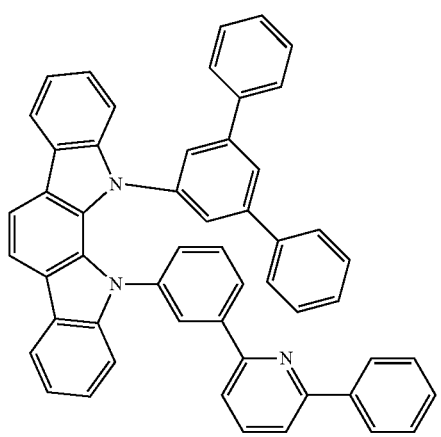
1-126
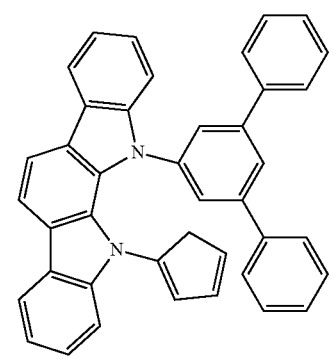

-continued
| 1-127 | 1-128 |
|---|---|
| 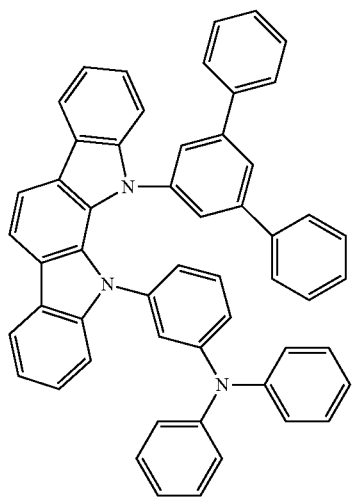 | 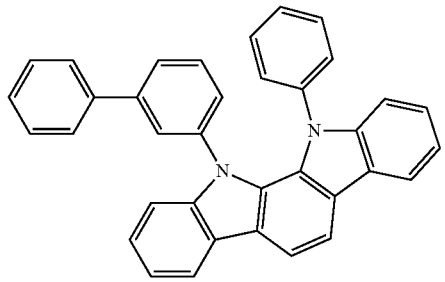 |
| 1-129 | 1-130 |
| 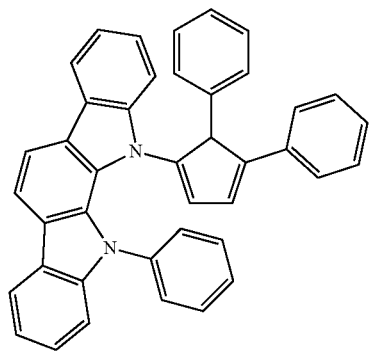 | 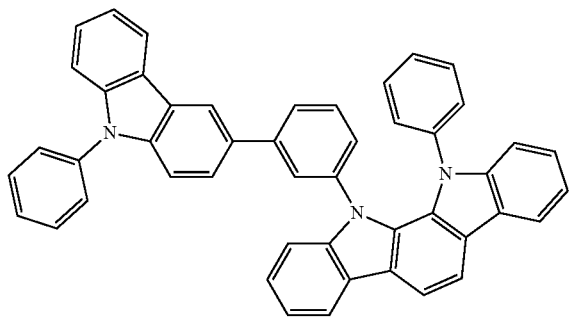 |
| 1-131 | 1-132 |
| 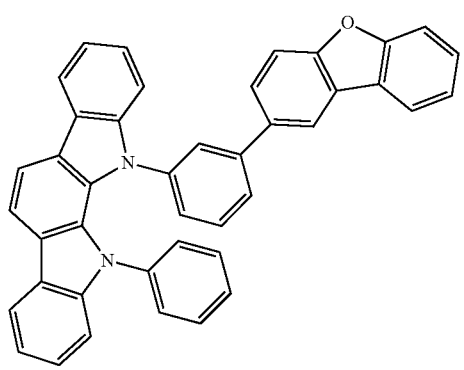 | 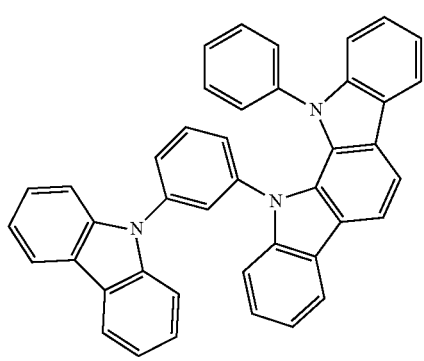 |

-continued
1-133
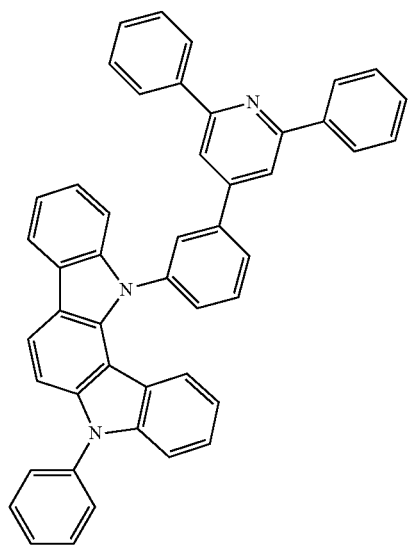
1-134
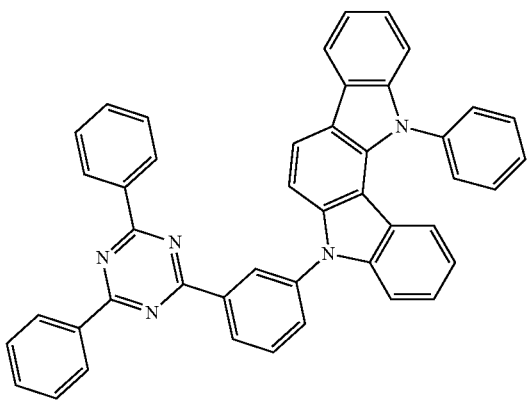
1-135
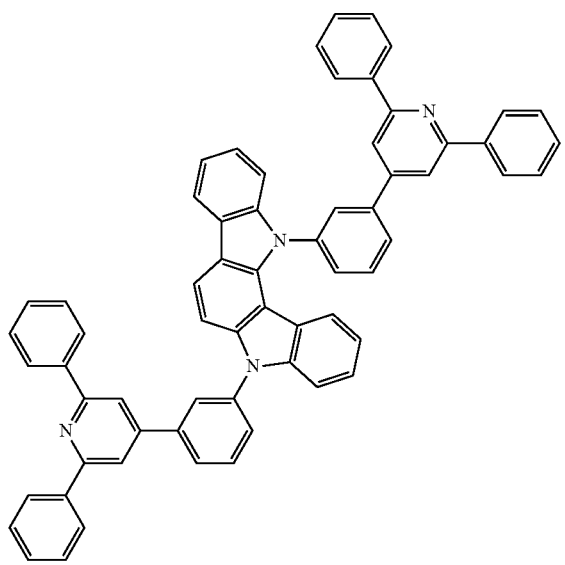
1-136
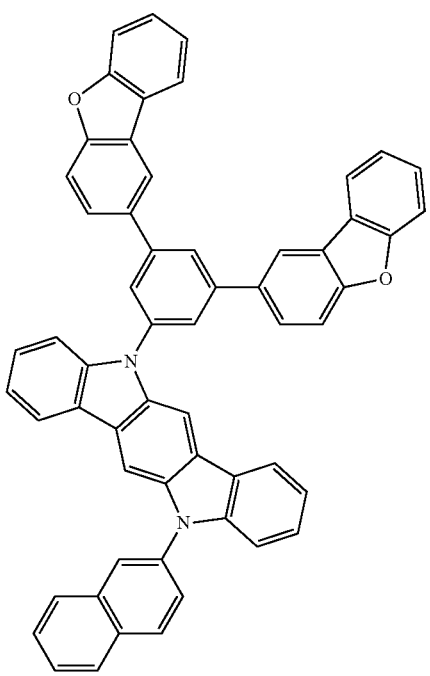

-continued
1-137
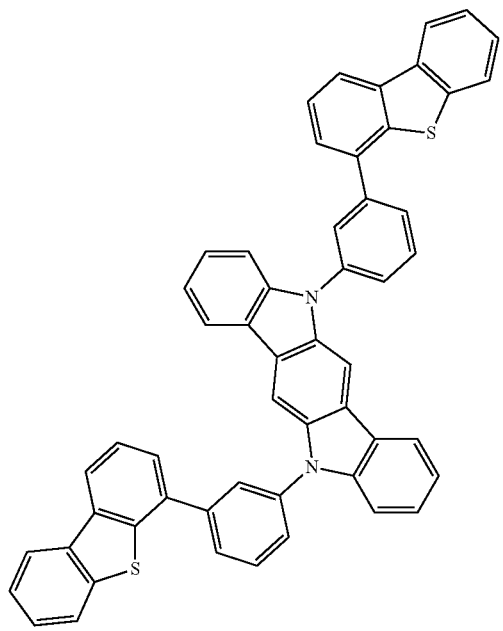
1-138
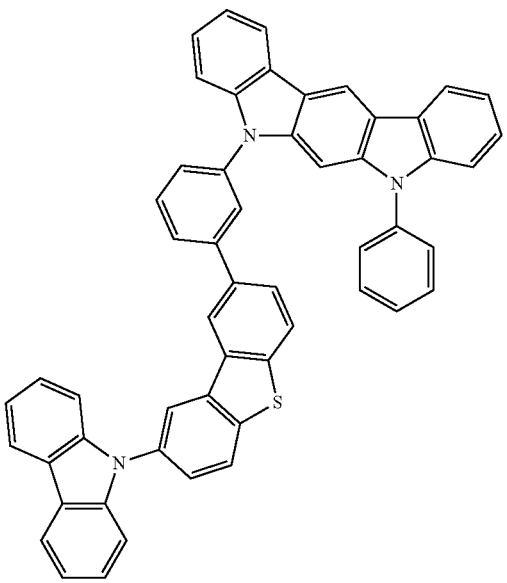
1-139
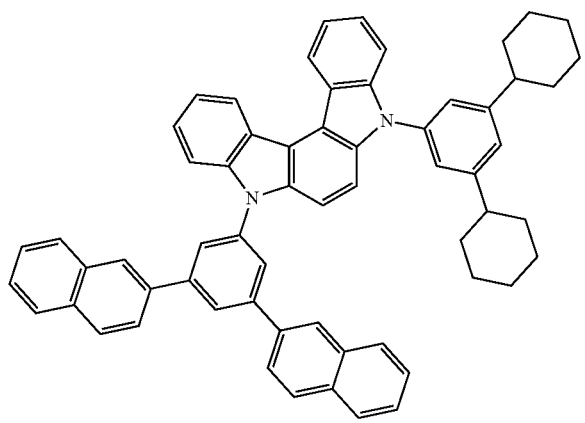
1-140
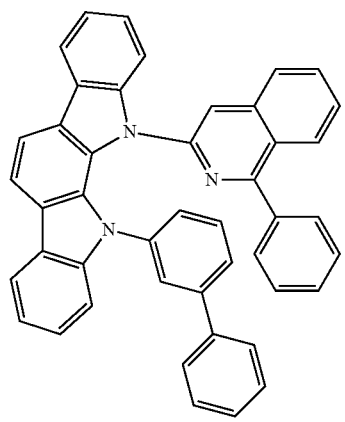
1-141
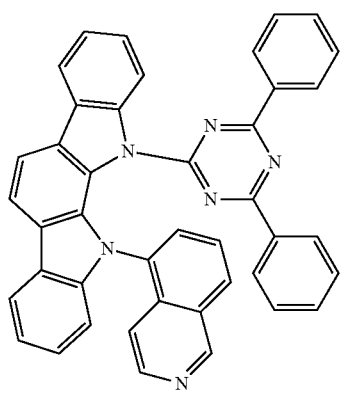
1-142
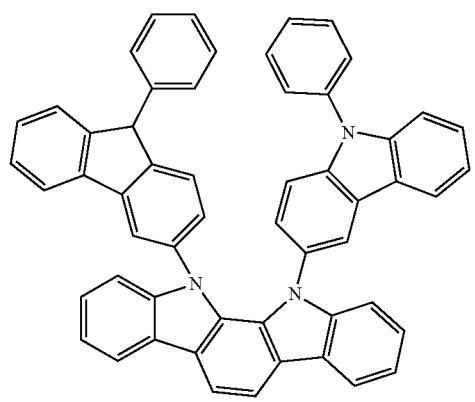

-continued
1-143
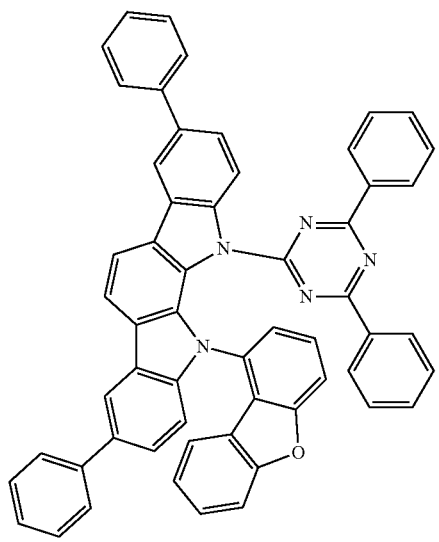
1-144
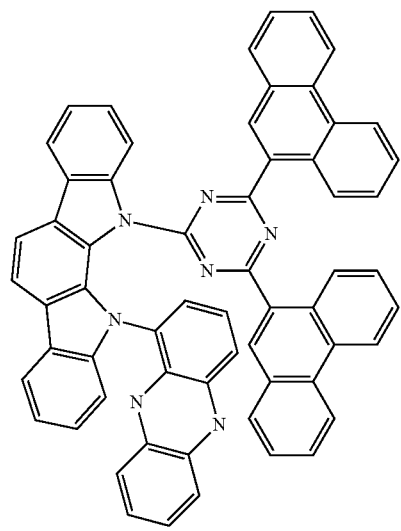
1-145
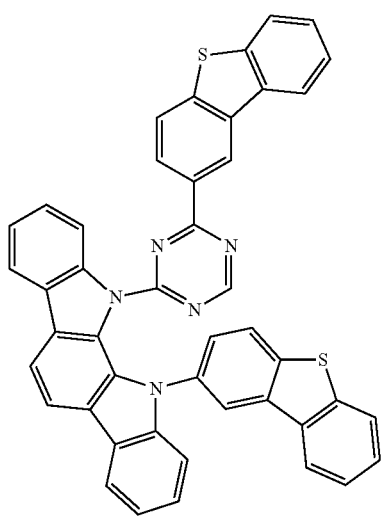
1-146
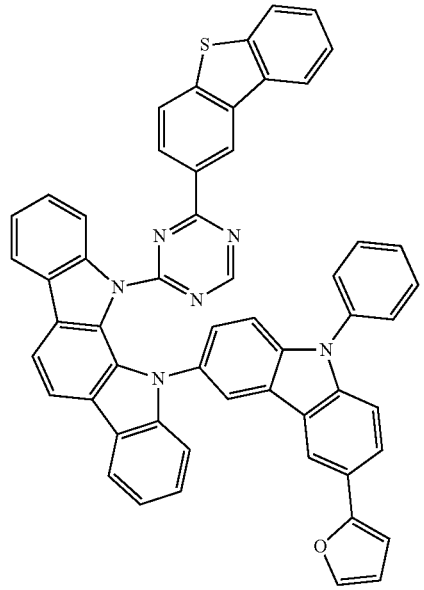
1-147
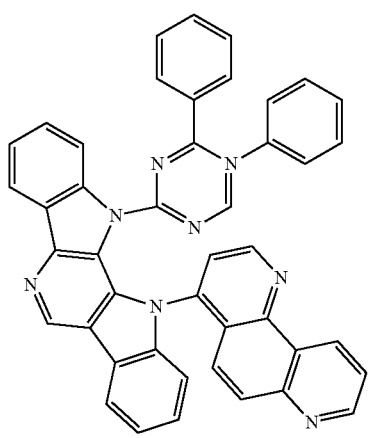
1-148
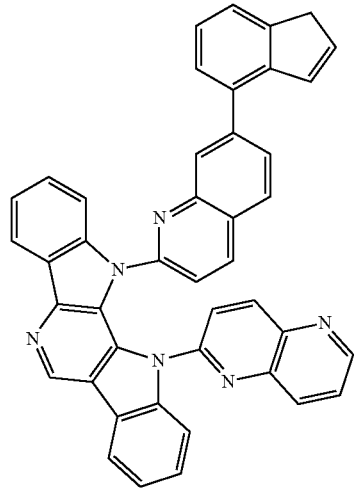

-continued
1-149
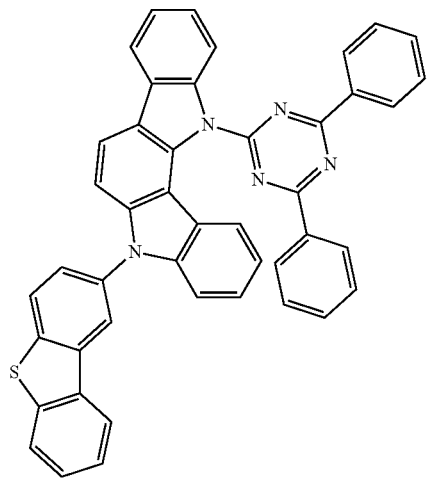
1-150
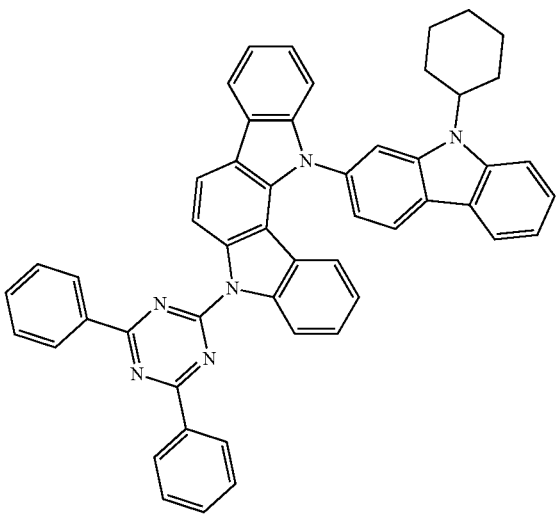
1-151
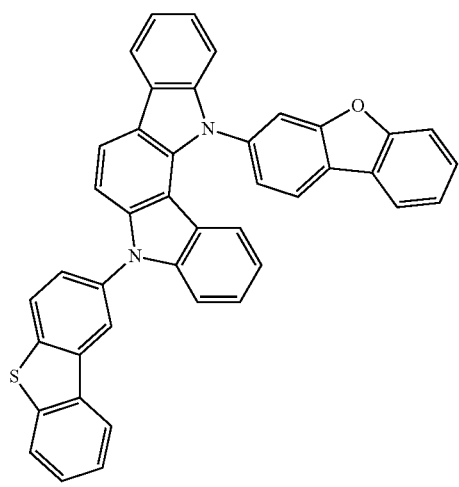
1-152
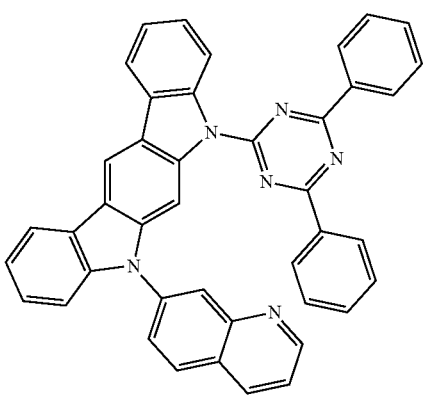
1-153
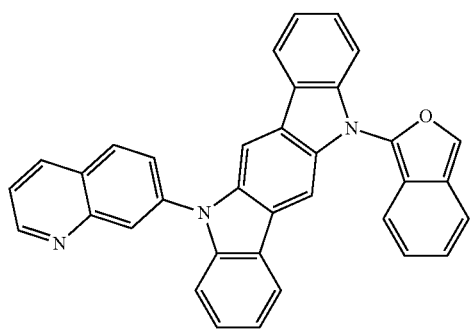
1-154
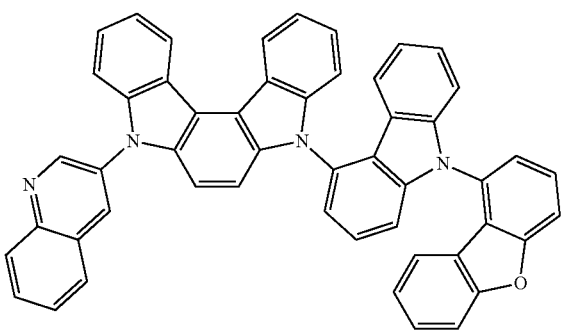

-continued
1-155
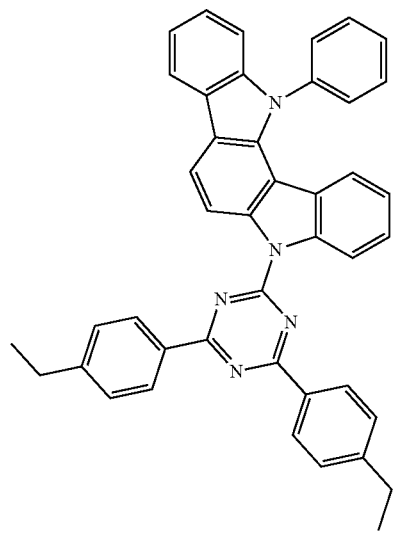
1-156
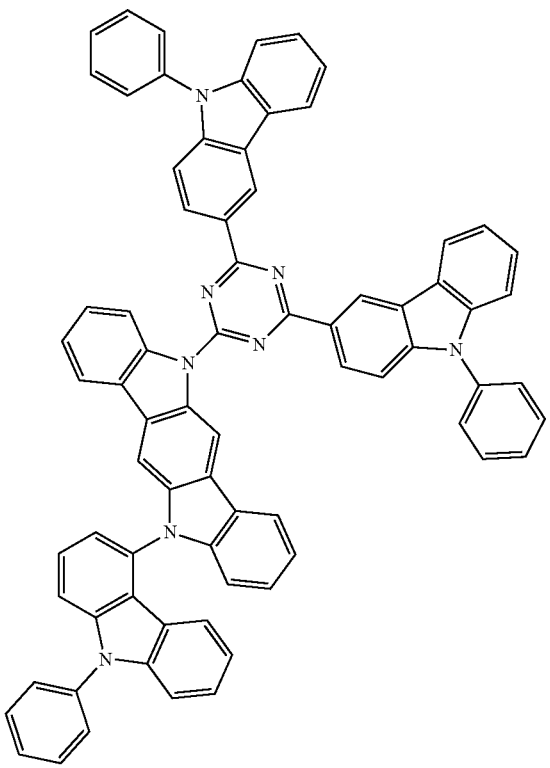
1-157
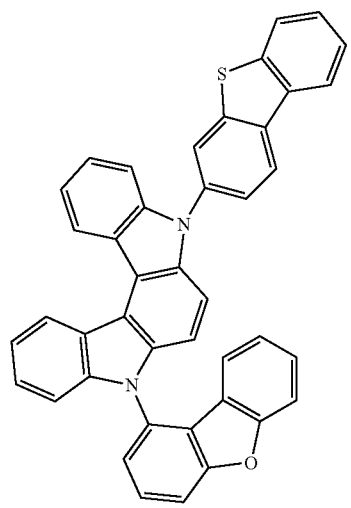
1-158
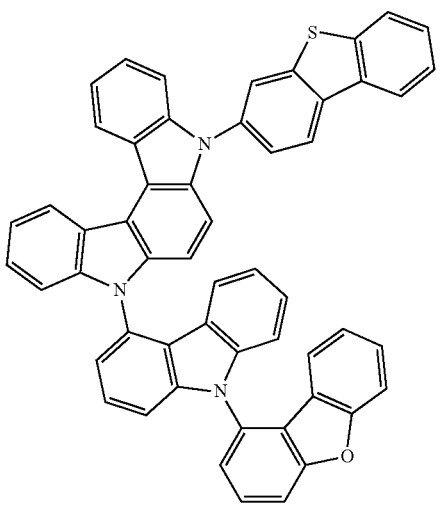

1-159
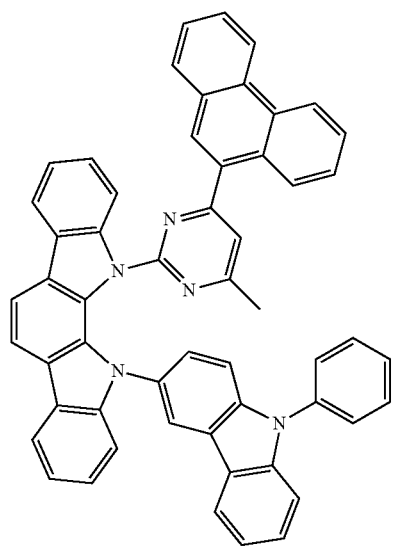
1-160
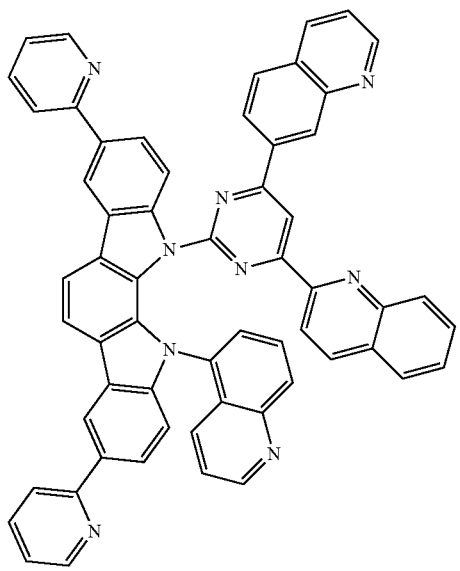
1-161
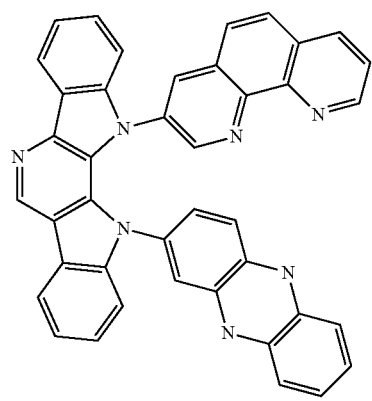
1-162
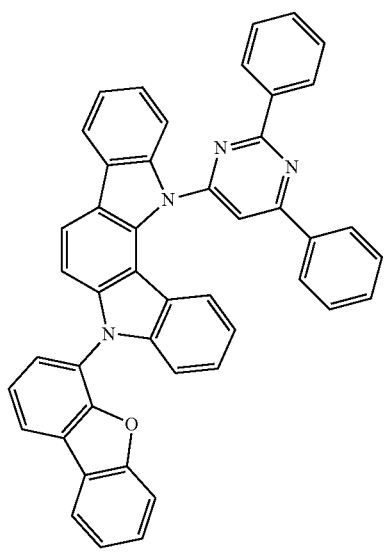

1-163
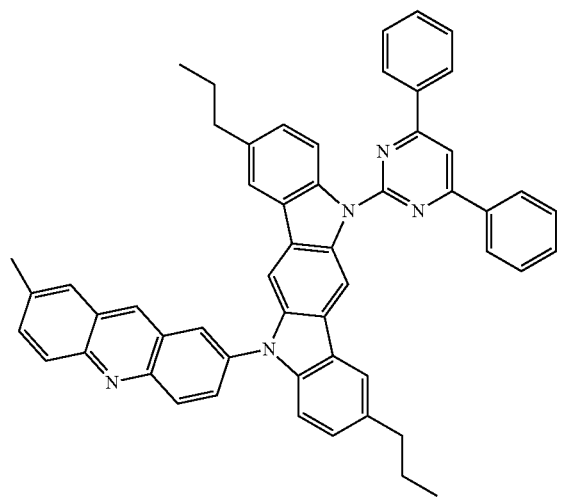
1-164
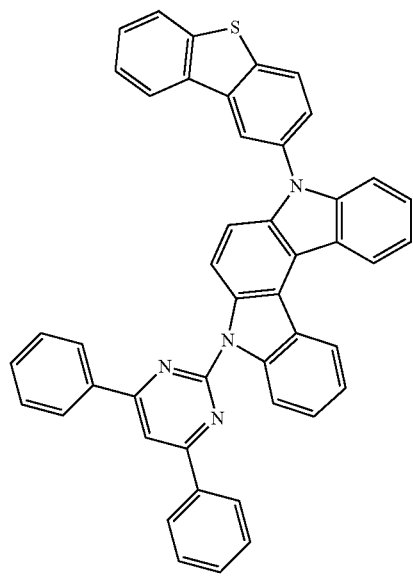
1-165
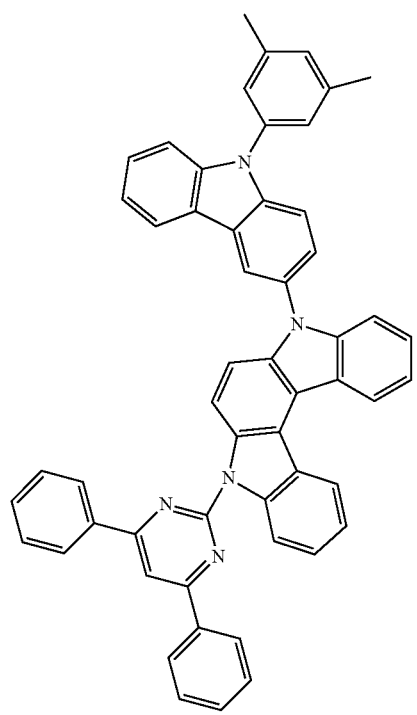
1-166
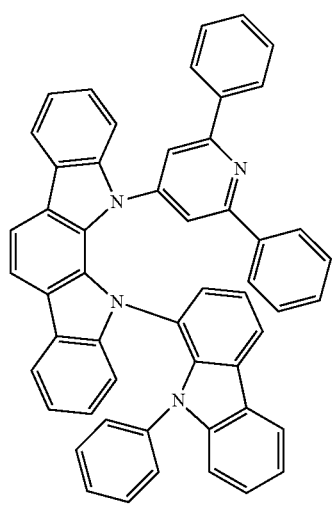

-continued
1-167
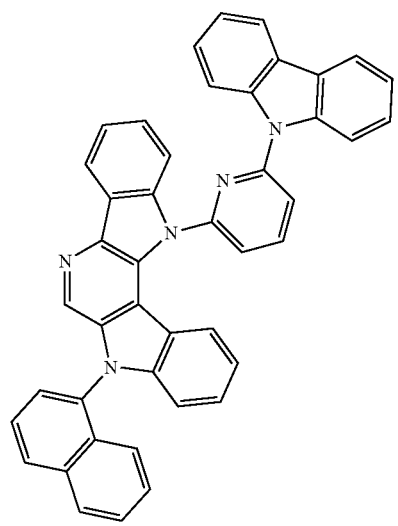
1-168
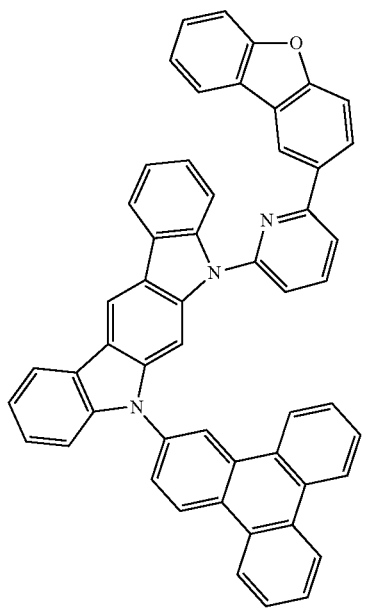
1-169
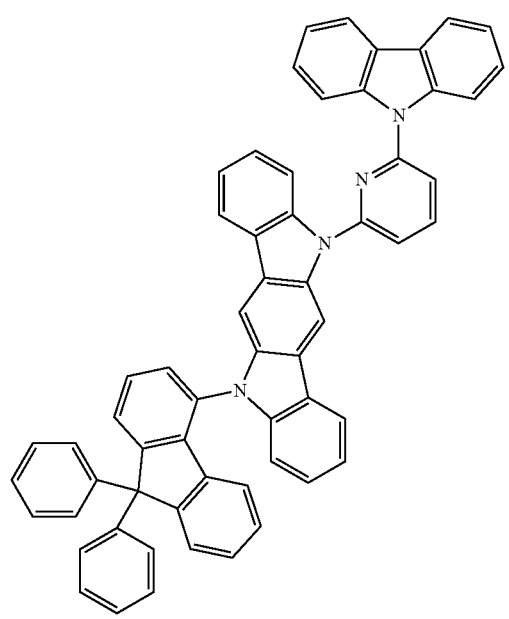
1-170
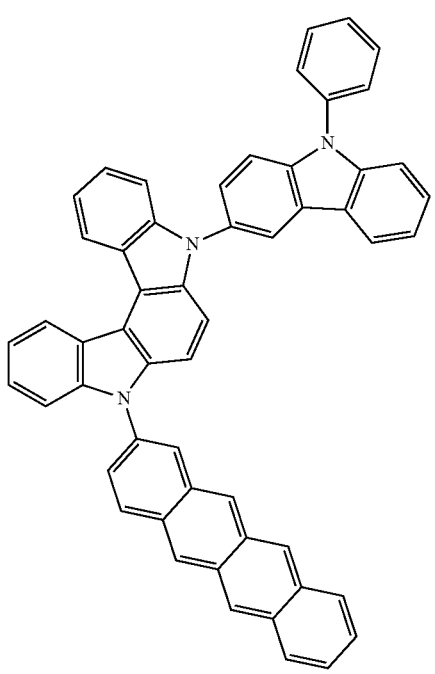

-continued
1-171
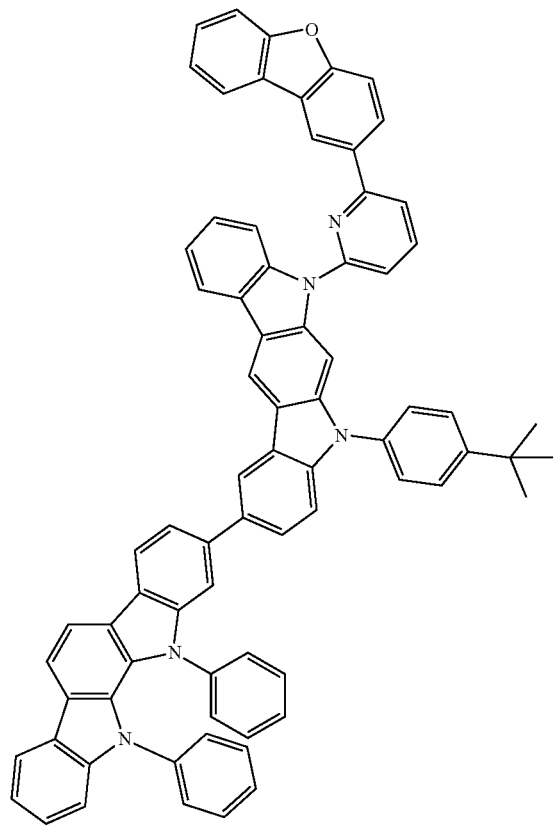
1-172
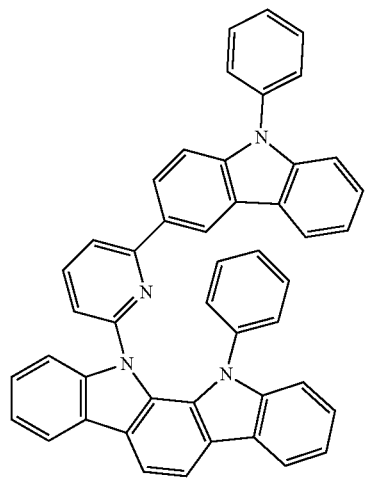
1-173
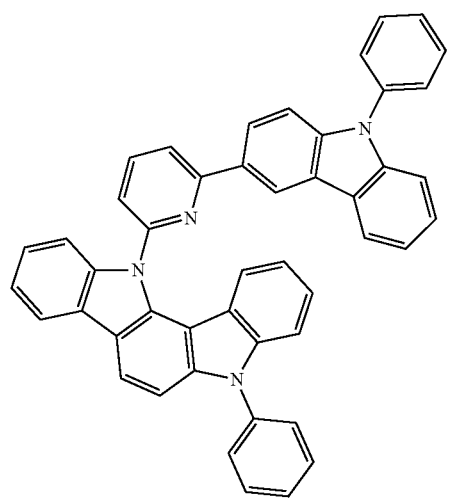
1-174
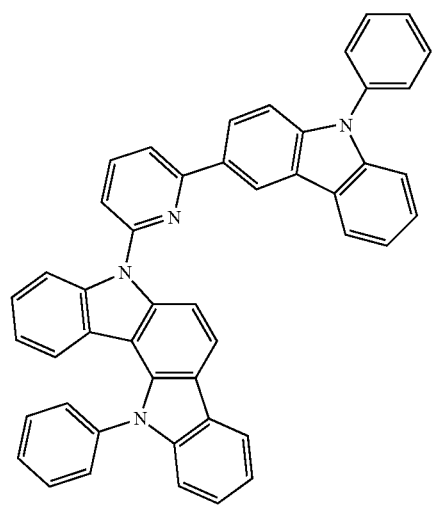

-continued
1-175
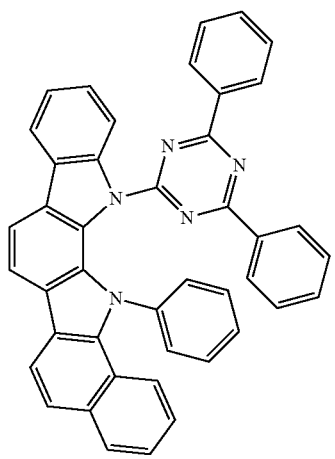
1-176
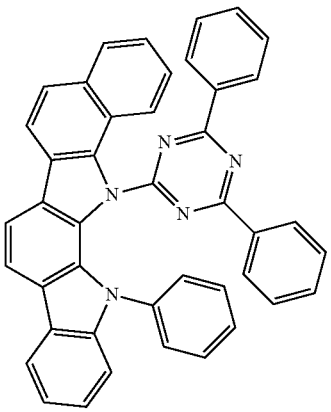
1-177
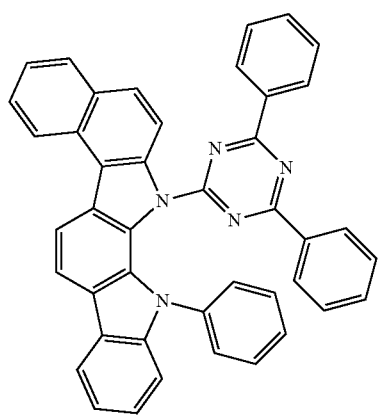
1-178
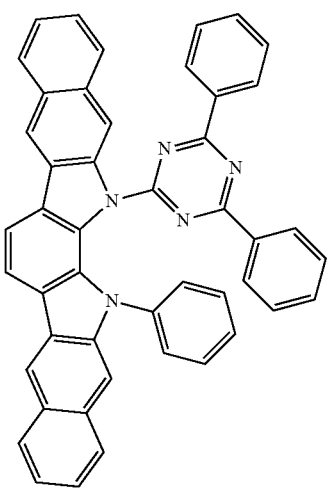
1-179
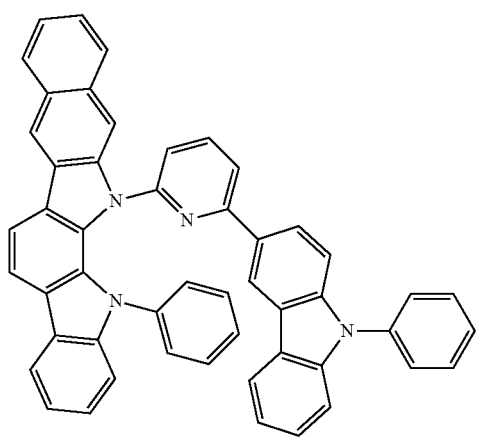
2-1
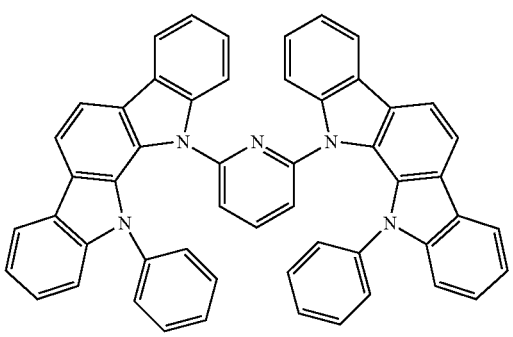

-continued
2-2
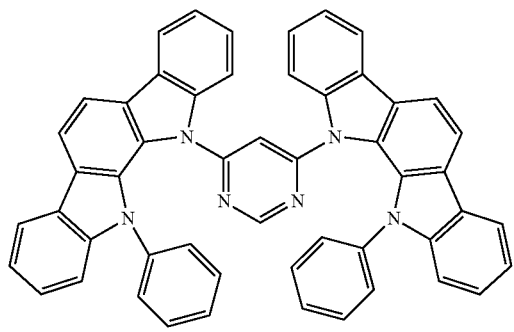
2-3
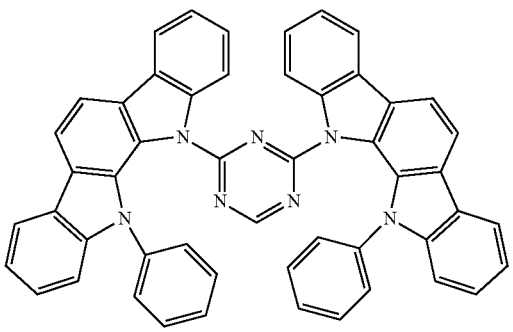
2-4
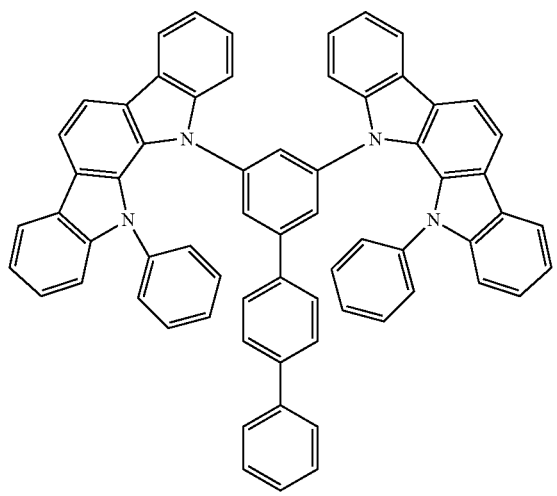
2-5
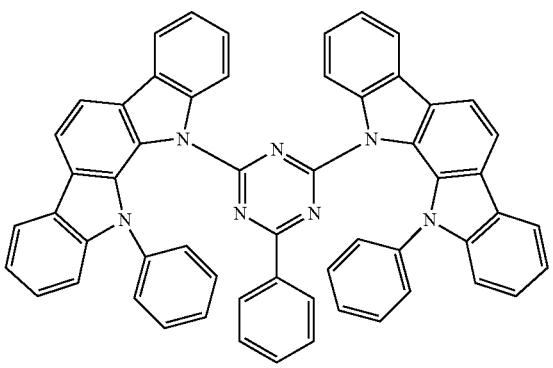
2-6
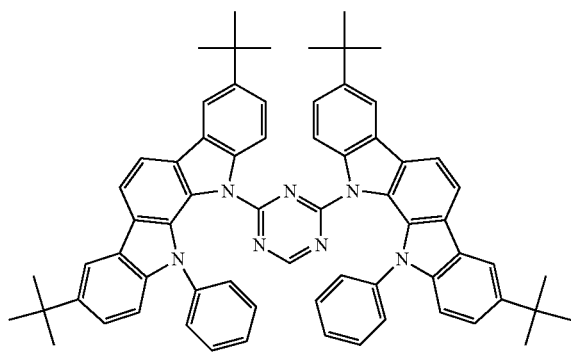
2-7
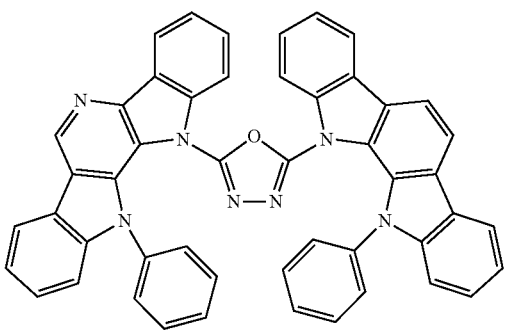
2-8
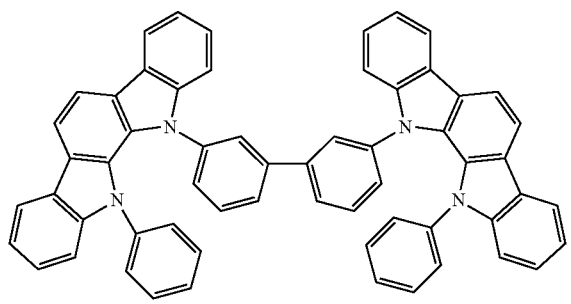
2-9
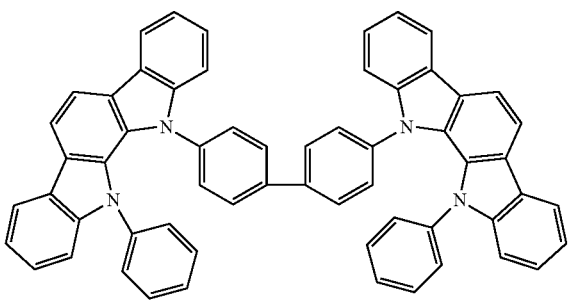

-continued
2-10
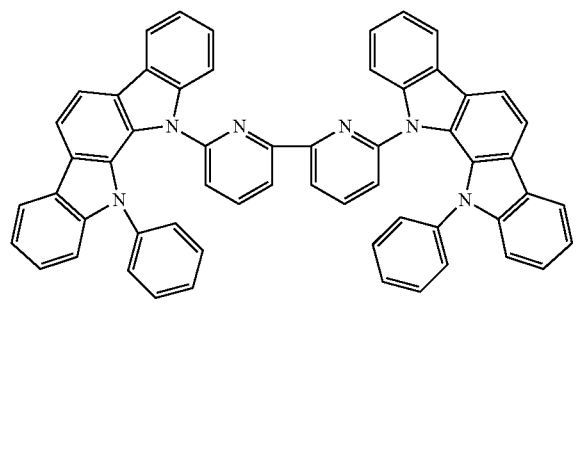
2-11
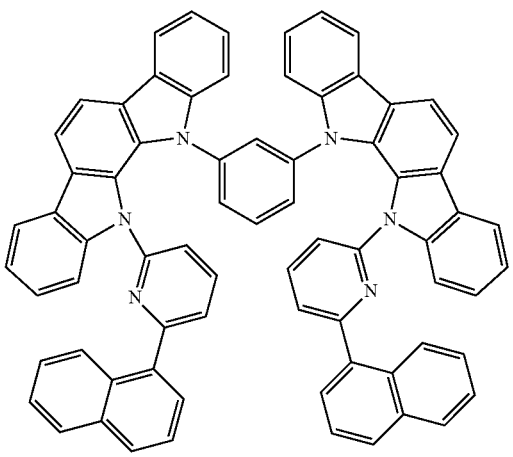
2-12
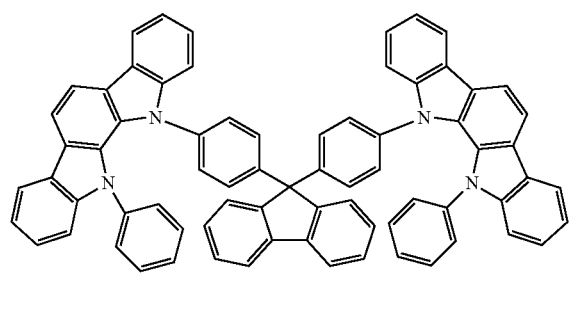
2-13
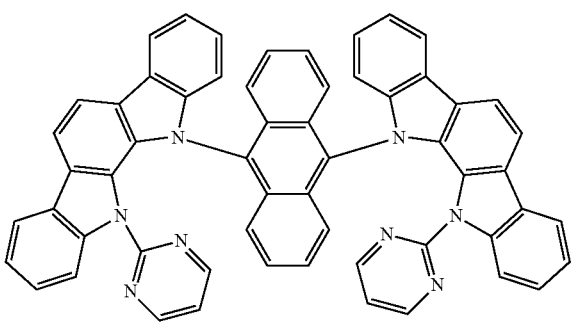
2-14
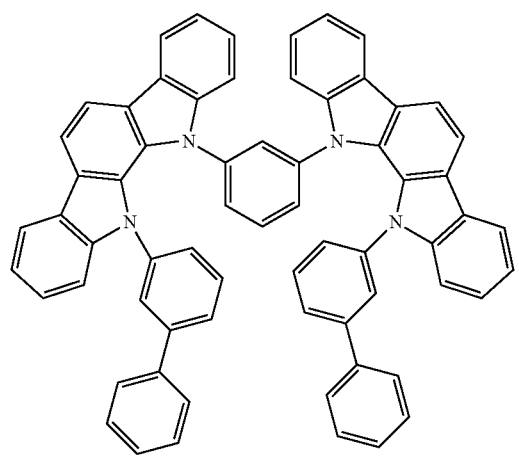
2-15
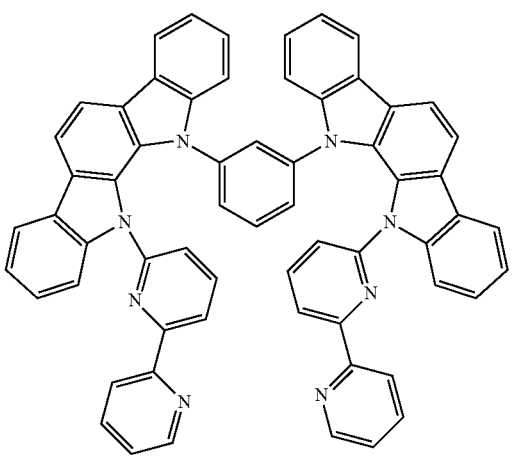

-continued
2-16
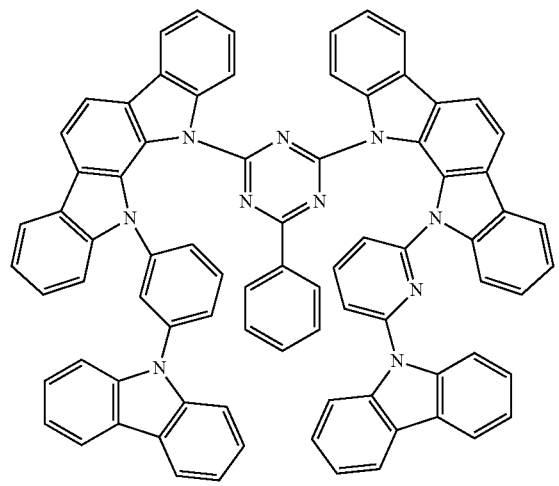
2-17
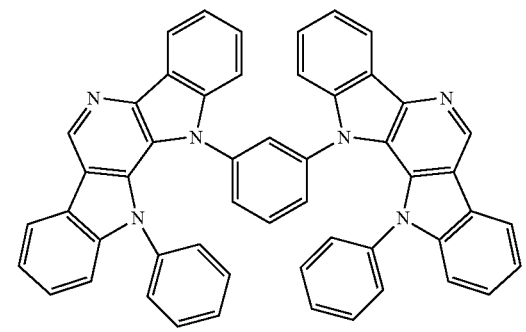
2-18
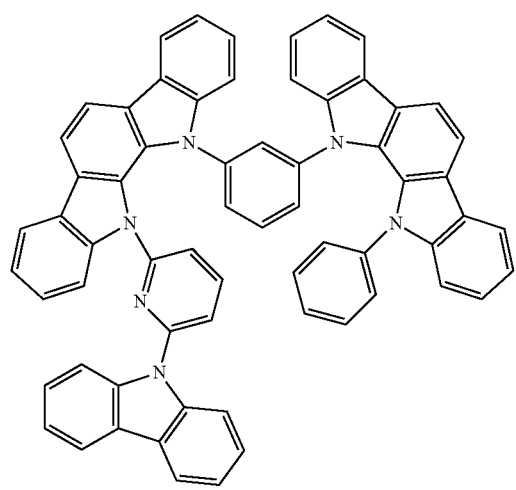
2-19
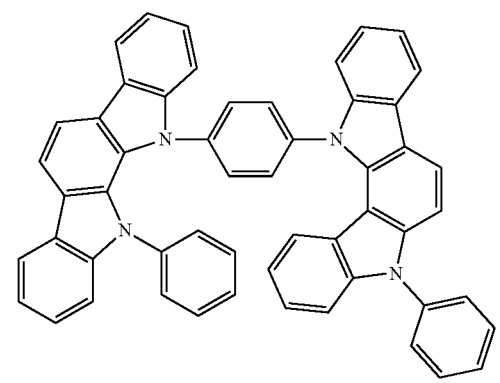
2-20
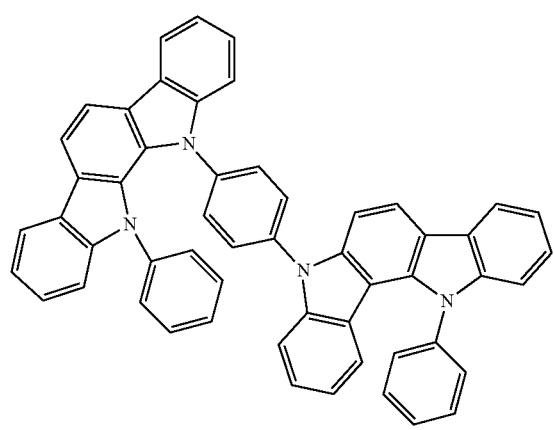
2-21
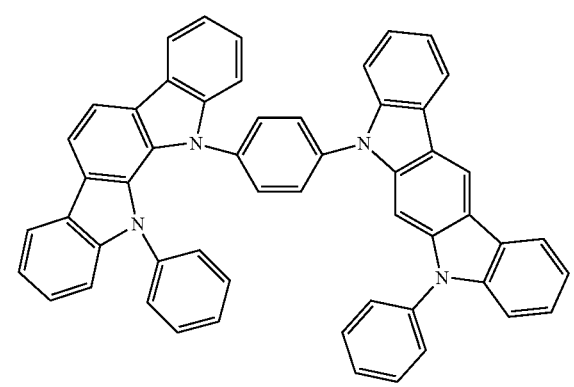

-continued
2-22
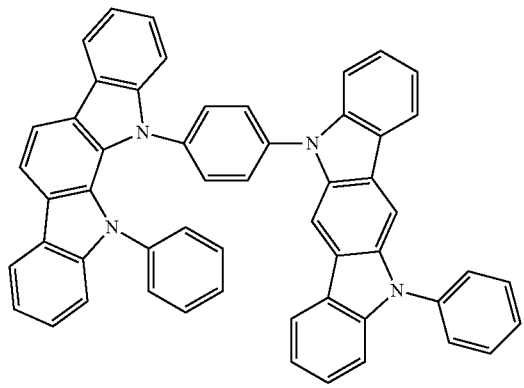
2-23
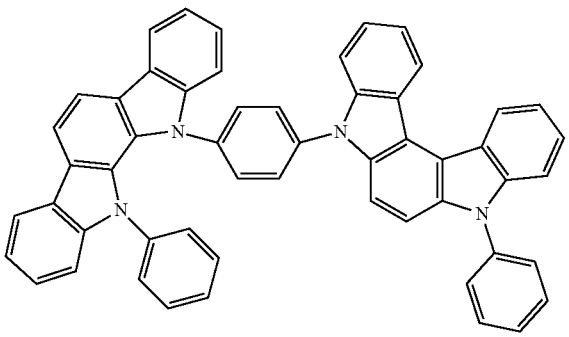
2-24
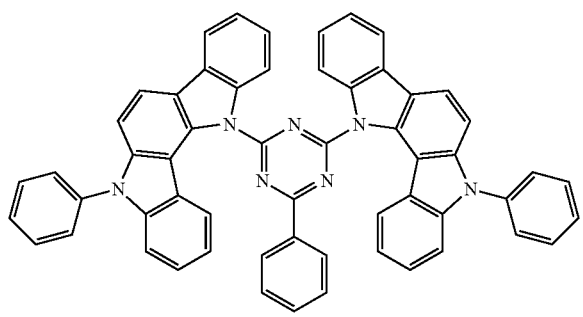
2-25
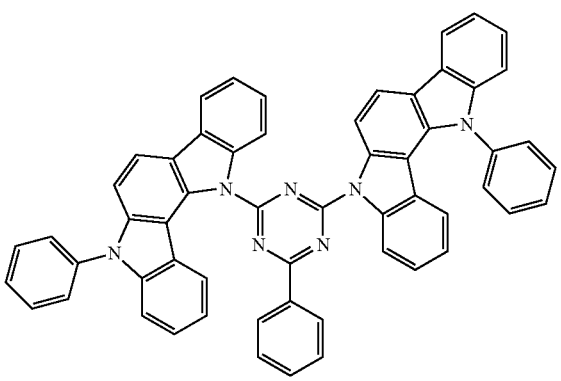
2-26
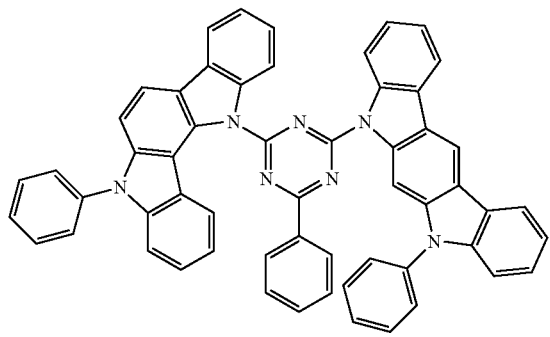
2-27
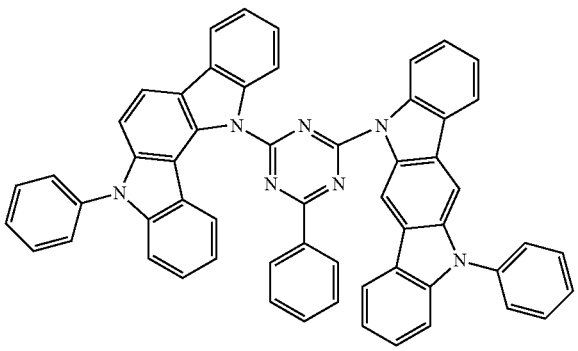
2-28
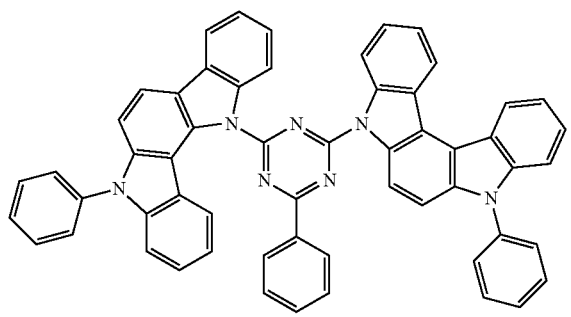
2-29
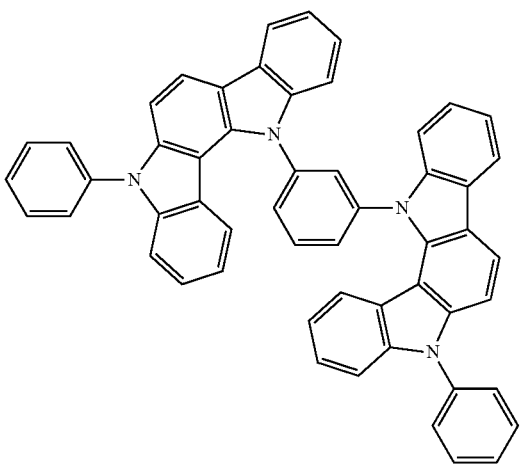

-continued
2-30
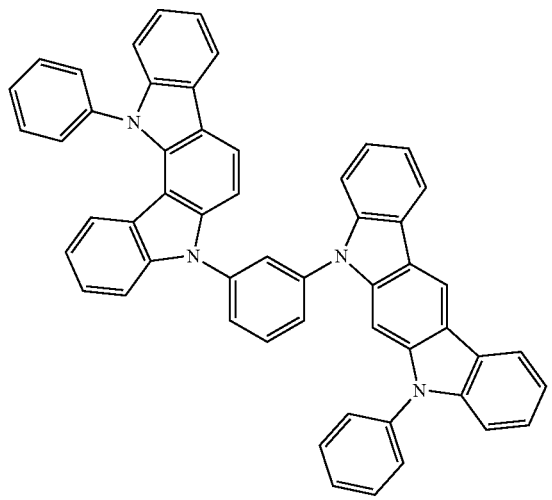
2-31
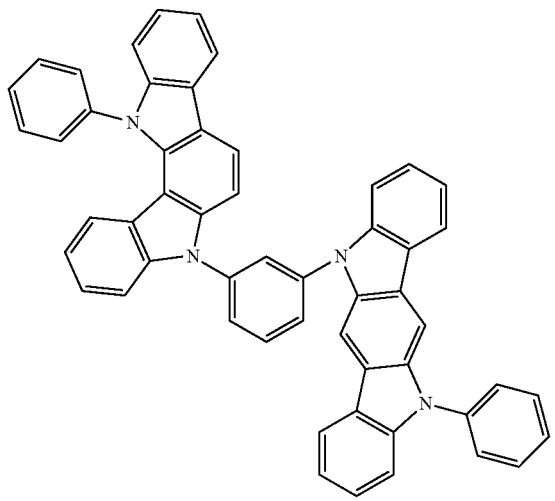
2-32
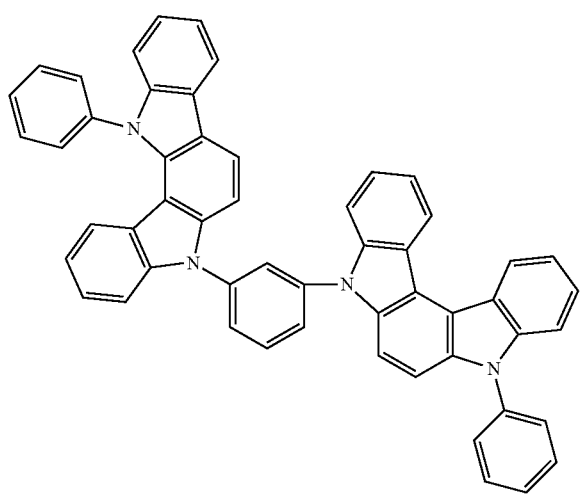
2-33
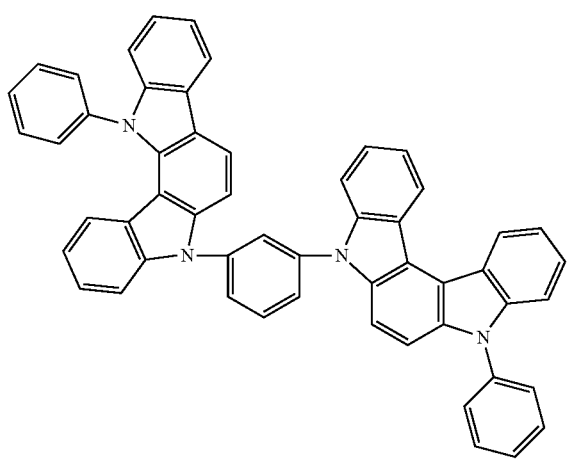
2-34
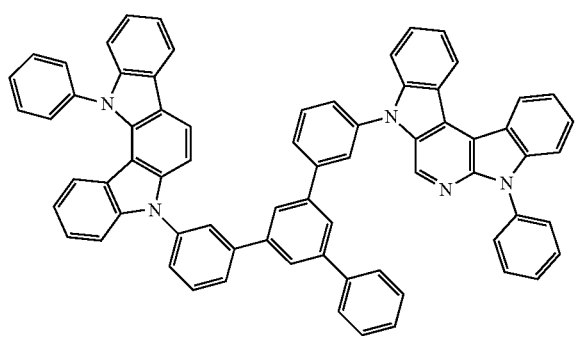
2-35
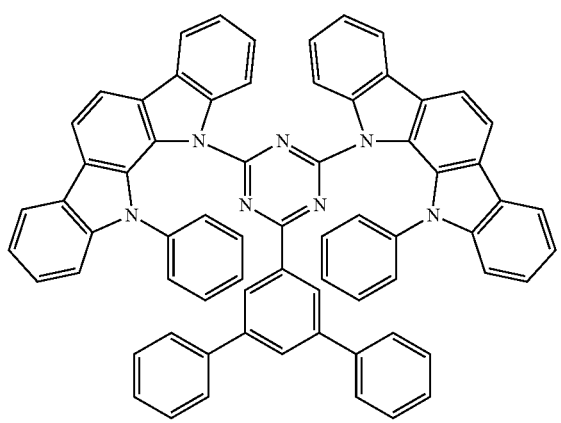

2-36
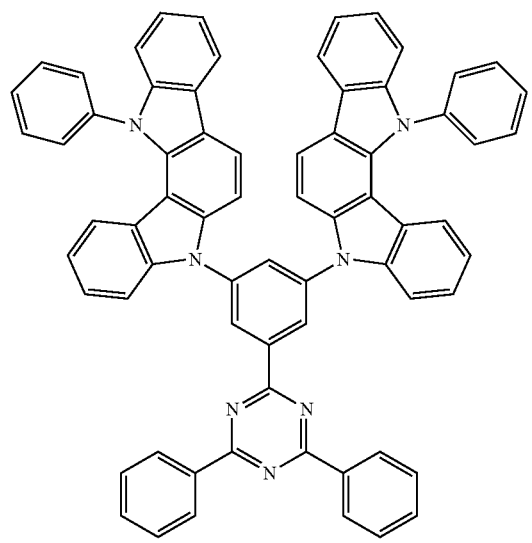
2-37
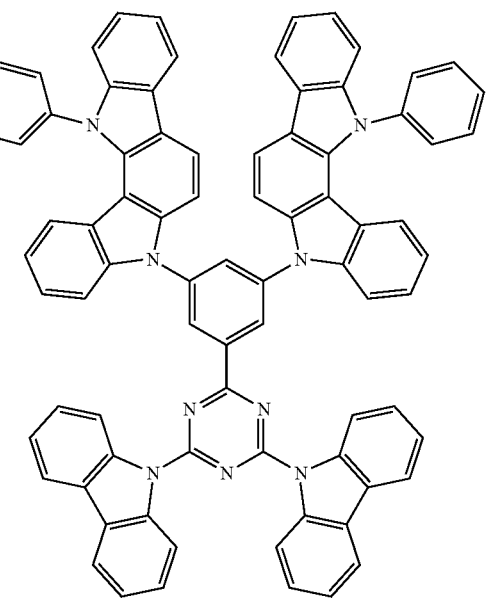
2-38
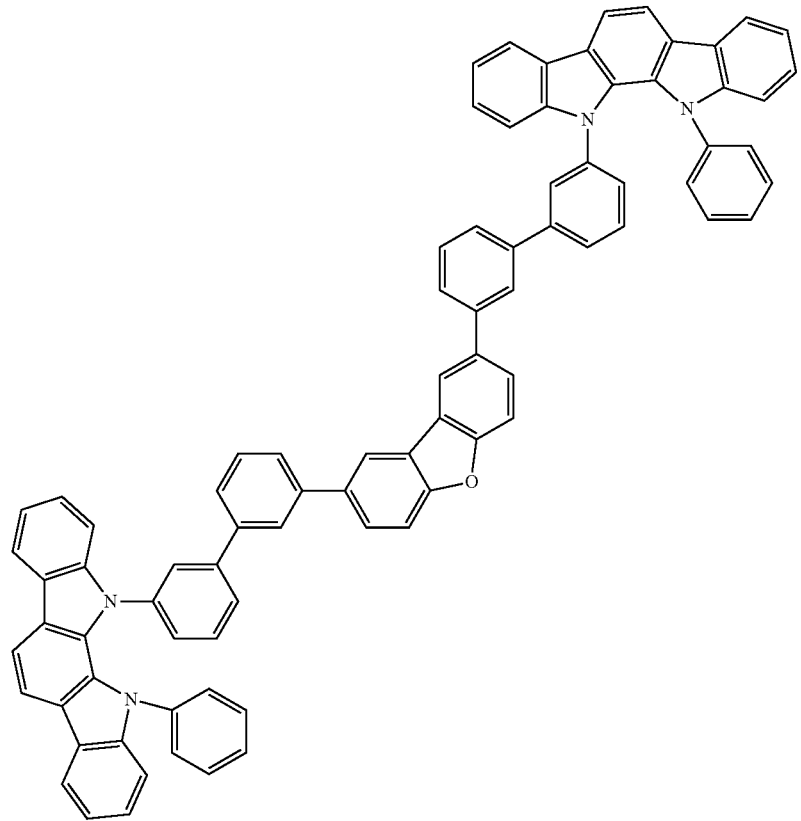

2-39
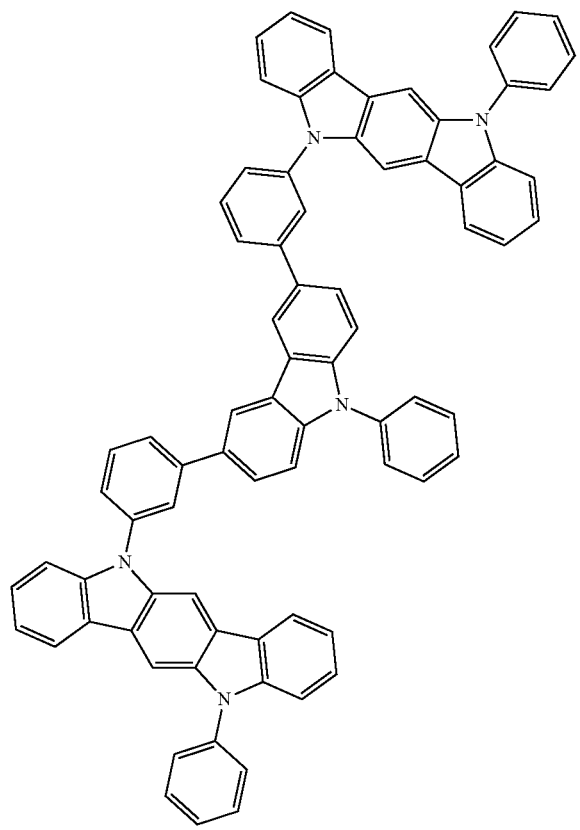
2-40
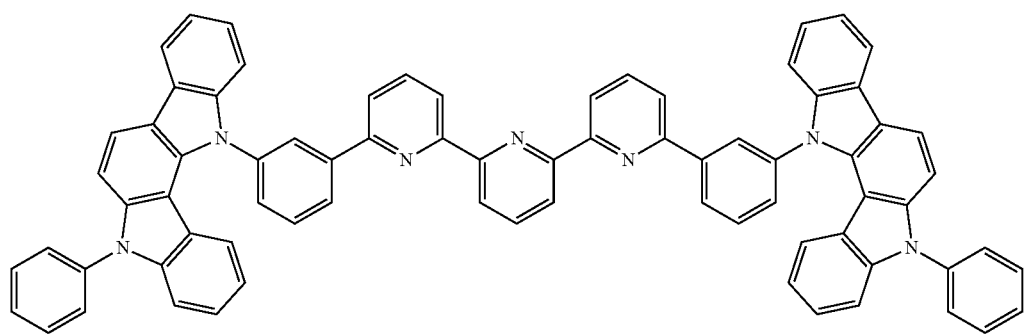

2-41
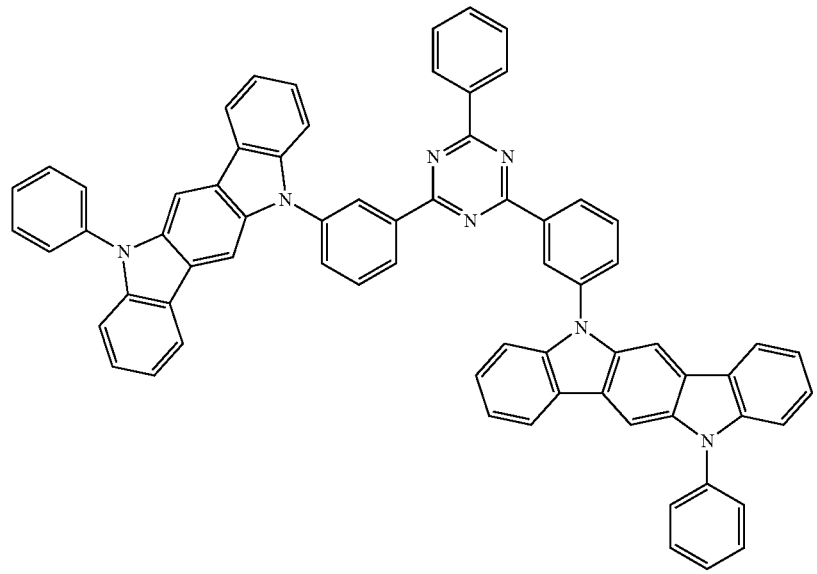
2-42
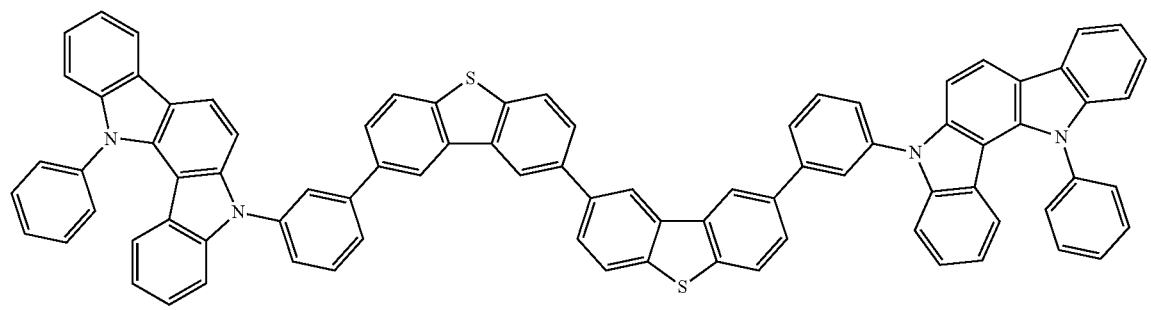
2-43
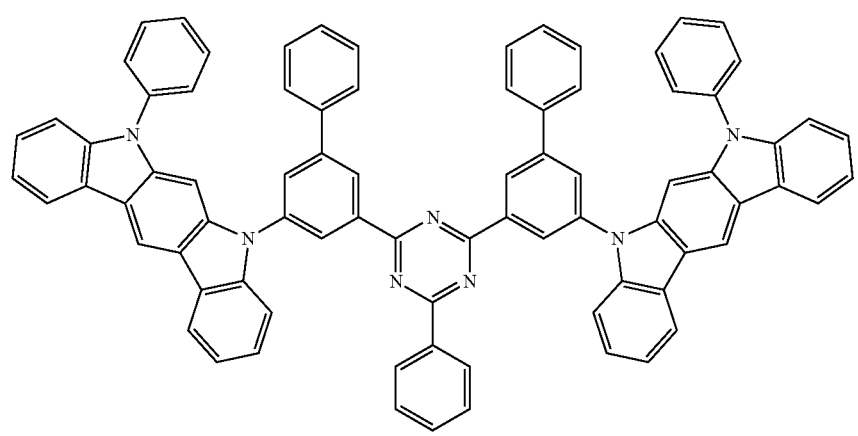

2-44
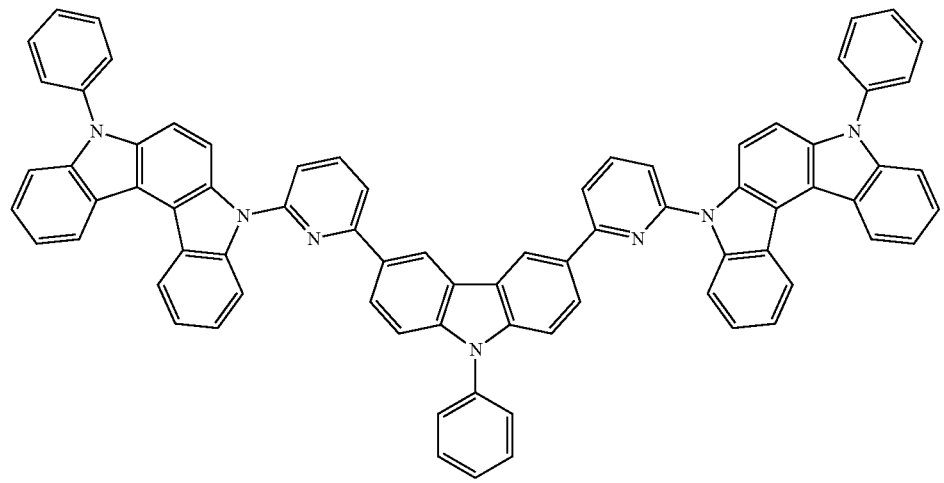
2-45
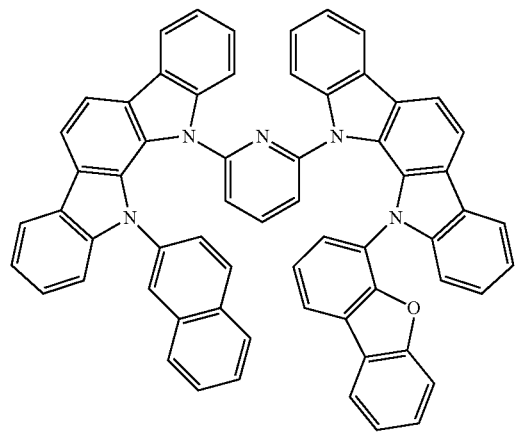
2-46
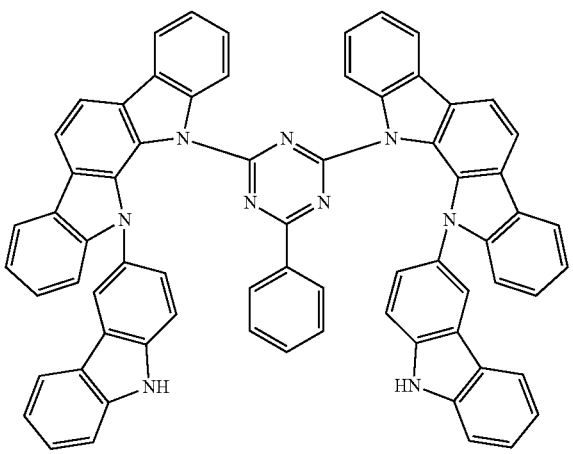
2-47
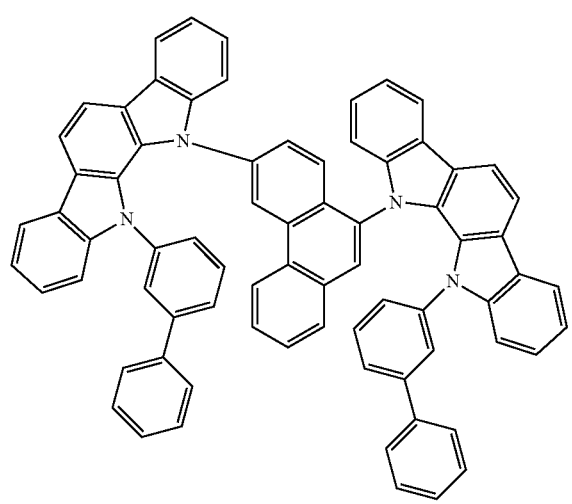
2-48
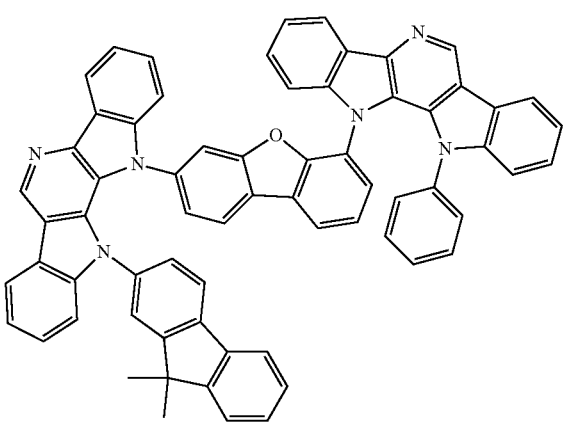

-continued
2-49
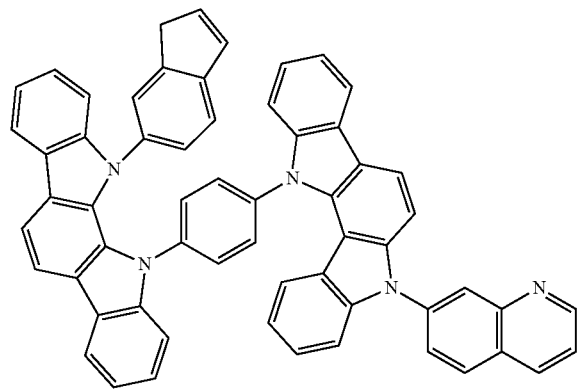
2-50
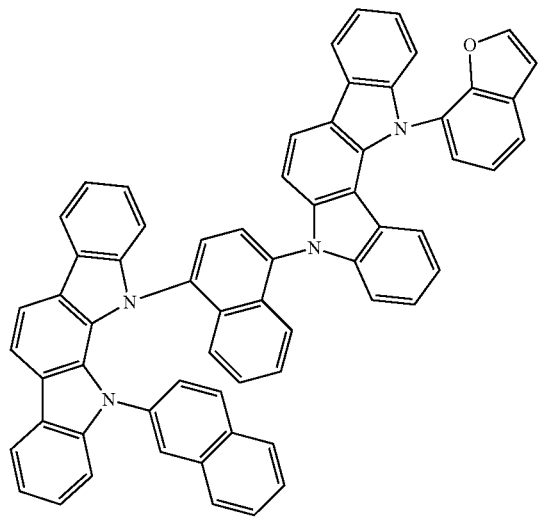
2-51
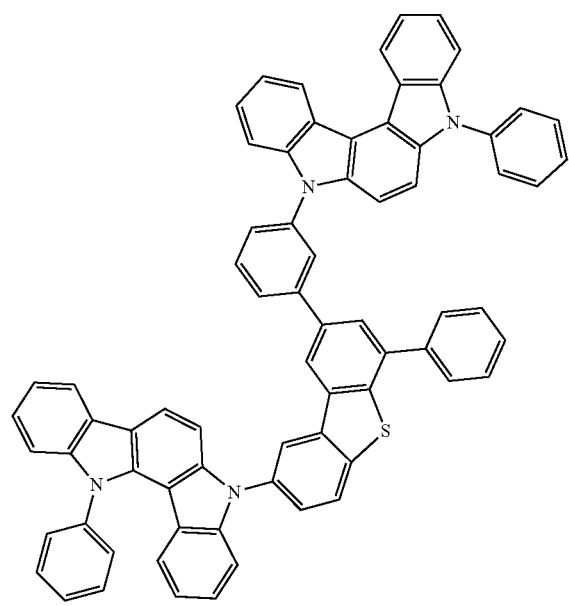
2-52
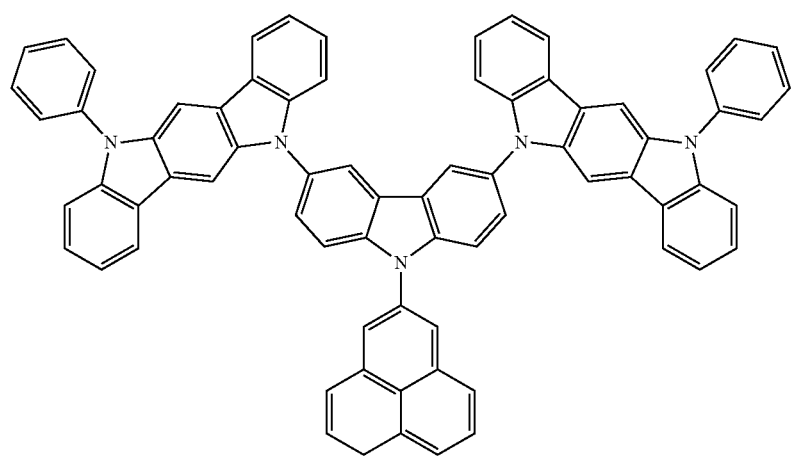

-continued
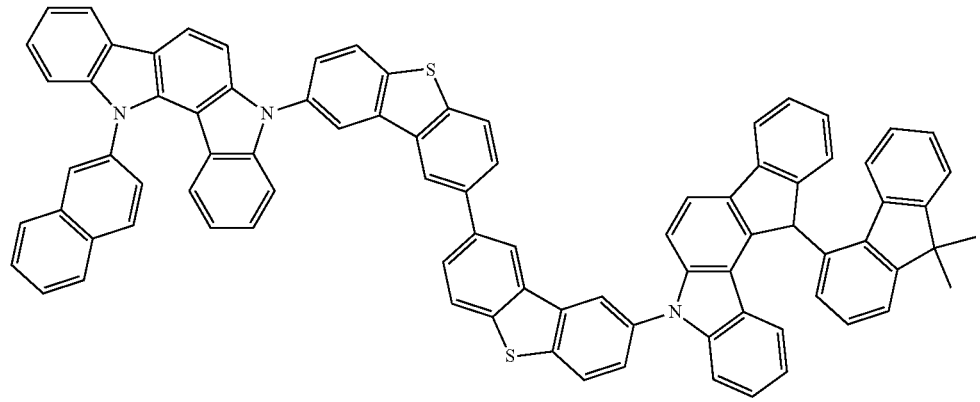
2-53
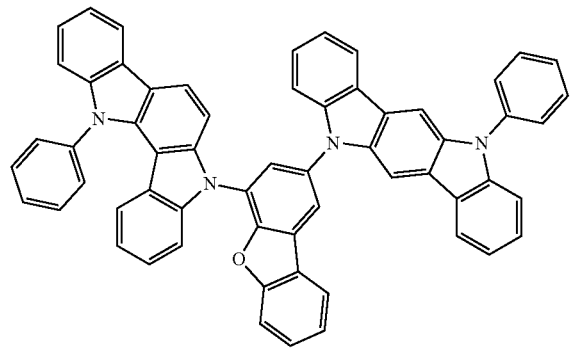
2-54
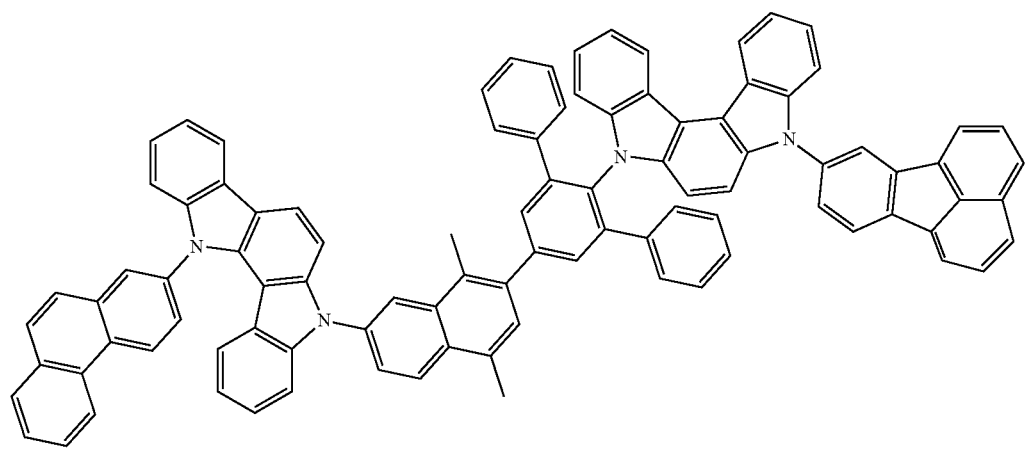
2-55

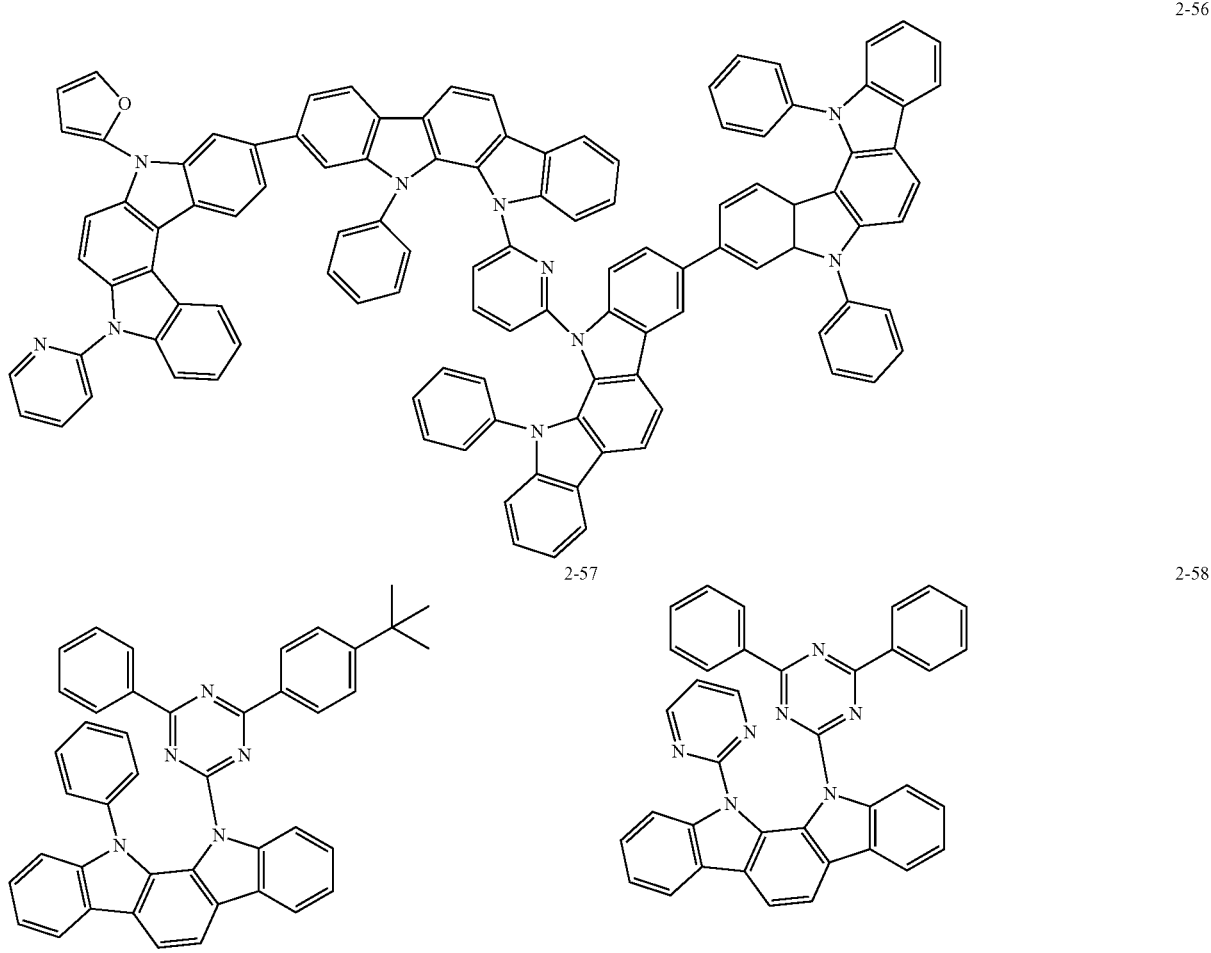

Next, the general formula (3) is described.

In the general formula (3), L represents an m-valent aromatic hydrocarbon group or aromatic heterocyclic group produced by removing m hydrogen atoms from an aromatic hydrocarbon having 6 to 30 carbon atoms or an aromatic heterocyclic compound having 3 to 16 carbon atoms, or an m-valent linked aromatic group obtained by linking 2 to 10 aromatic rings of the groups. L preferably represents an aromatic hydrocarbon group having 6 to 18 carbon atoms or an aromatic heterocyclic group having 3 to 15 carbon atoms, or a linked aromatic group obtained by linking 2 to 10 aromatic rings of the groups. Here, the aromatic hydrocarbon group or the aromatic heterocyclic group may have a substituent. When L represents the aromatic heterocyclic group, the group is preferably a nitrogen-containing heterocyclic group. L does not represent a group containing a carbazole ring. The term "group containing a carbazole ring" as used herein refers to an m-valent group produced by removing m hydrogen atoms from a substituted or unsubstituted carbazole, or a group containing a group produced by removing one or more hydrogen atoms from a substituted or unsubstituted carbazole. When L has a substituent, examples of the substituent include the same examples as those of the substituent in the case where any one of $Ar^1$, Z, and $L^1$ in the formula (1) represents a substituted aromatic hydrocarbon group or a substituted aromatic heterocyclic group. The number of substituents is preferably from 0 to 3, more preferably from 0 to 2 per one aromatic ring.

Specific examples of the aromatic hydrocarbon or the aromatic heterocyclic compound include benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, a helicene, hexaphene, rubicene, coronene, trinaphthylene, heptaphene, pyranthrene, furan, benzofuran, isobenzofuran, xanthene, oxanthrene, dibenzofuran, peri-xanthenoxanthene, thiophene, thioxanthene, thianthrene, phenoxathiin, thionaphthene, isothianaphthene, thiophthene, thiophanthrene, dibenzothiophene, pyrrole, pyrazole, tellurazole, selenazole, thiazole, isothiazole, oxazole, furazan, indolizine, indole, isoindole, indazole, purine, quinolizine, isoquinoline, imidazole, naphthyridine, phthalazine, a benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, benzothiazole, benzimidazole, benzoxazole, benzisoxazole, benzisothiazole, and an aromatic compound in which two or more of the aromatic rings of the compounds are linked.

In the case of the aromatic compound in which a plurality of aromatic rings are linked, the number of the aromatic rings to be linked is preferably from 2 to 10, more preferably from 2 to 7, and the aromatic rings to be linked may be identical to or different from each other. In that case, in the formula (3), a bonding position to be bonded to m carbazolyl groups is not limited, and may be a ring at a terminal portion of the linked aromatic rings or a ring at the central portion thereof. The term "aromatic ring" as used herein is a generic term for an aromatic hydrocarbon ring and an aromatic heterocycle. In addition, when the linked aromatic rings include at least one heterocycle, the rings are included in an aromatic heterocycle.

Specific examples of the group produced by linking a plurality of aromatic rings include monovalent groups each produced by removing a hydrogen atom from biphenyl, terphenyl, quaterphenyl, binaphthalene, phenyltriphenylene, phenyldibenzofuran, phenyldibenzothiophene, bisdibenzofuran, or bisdibenzothiophene.

In the general formula (3), a preferred mode of L is, for example, an m-valent group produced from an aromatic compound represented by any one of the formulae (4) to (7), preferably any one of the formulae (4) to (6). Such m-valent group is an m-valent group produced by removing m hydrogen atoms from carbon atoms forming a ring appearing in any one of the formulae (4) to (7), and when m represents 2 or more, the hydrogen atoms may be removed from one and the same ring or from different rings.

In each of the formulae (5) and (7), $X^2$ represents an oxygen atom or a sulfur atom. In the formula (6), q represents an integer of from 0 to 2, preferably 0 or 1.

In the general formula (3), an aromatic compound that provides preferred L is specifically, for example, benzene, naphthalene, anthracene, biphenyl, terphenyl, dibenzofuran, dibenzothiophene, phenyldibenzofuran, or phenyldibenzothiophene. Of those, benzene, biphenyl, or terphenyl is more preferred.

In the general formula (3), m represents an integer of from 1 to 3, preferably 1 or 2, more preferably 1.

In the general formula (3), n's each independently represent an integer of from 1 to 4, preferably from 1 to 3. However, at least one n represents an integer of from 2 to 4, and at least one bond structure represented by the formula (c1) is present in the general formula (3). All bond structures between carbazole rings are preferably bond structures represented by the formula (c1) or by the formula (c1) and the formula (d1). The product (n×m) of n and m is an integer of from 2 to 12, preferably from 2 to 9, more preferably from 2 to 6. The number is the total number of carbazole rings appearing in the parentheses of the general formula (3).

In the general formula (3), a bond structure represented by the formula (c1) needs to be present, and when n represents 2 or more, all bond structures are preferably bond structures each represented by the formula (c1) or bond structures represented by the formula (c1) and the formula (d1). Here, when n represents 3 or more, two or more bond structures are present, and each of the structures is preferably such bond structure as described above. In each of the bond structures represented by the formula (c1) and the formula (d1), when one carbazole ring is a terminal carbazole ring, one bond is bonded to a hydrogen atom.

In the general formulae (3) to (7), and the formulae (c1) and (d1), R's each independently represent a hydrogen atom, an alkyl group having 1 to 10 carbon atoms, or a cycloalkyl group having 3 toll carbon atoms. R's each represent preferably a hydrogen atom, an alkyl group having 1 to 8 carbon atoms, or a cycloalkyl group having 3 to 8 carbon atoms, more preferably a hydrogen atom, an alkyl group having 1 to 4 carbon atoms, or a cycloalkyl group having 5 to 7 carbon atoms.

Specific examples of the alkyl group include a methyl group, an ethyl group, a propyl group, a butyl group, a pentyl group, a hexyl group, a heptyl group, an octyl group, a nonyl group, and a decyl group. Preferred examples thereof include a methyl group, an ethyl group, a propyl group, a butyl group, a pentyl group, a hexyl group, a heptyl group, and an octyl group. The alkyl group may be linear or branched.

Specific examples of the cycloalkyl group include a cyclopropyl group, a cyclobutyl group, a cyclopentyl group, a cyclohexyl group, a cycloheptyl group, a cyclooctyl group, and a methylcyclohexyl group. Preferred examples thereof include a cyclohexyl group and a methylcyclohexyl group.

Specific examples of the carbazole compound represented by the general formula (3) are shown below. However, the compound is not limited thereto.

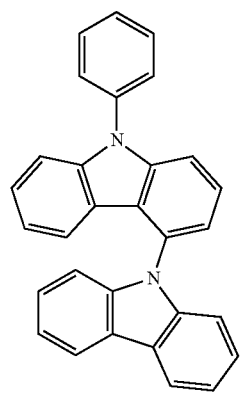

3-1

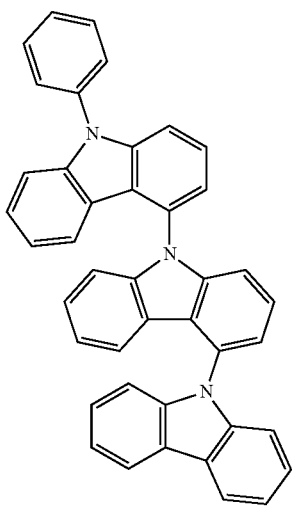

3-2

-continued
3-3
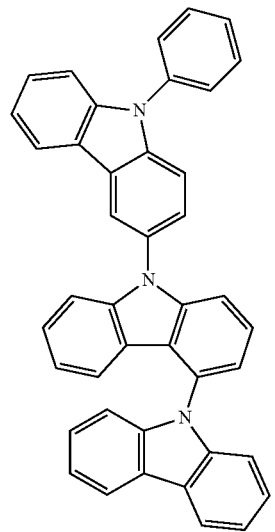
3-4
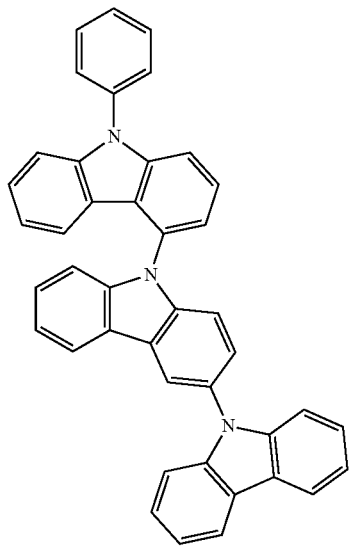
3-5
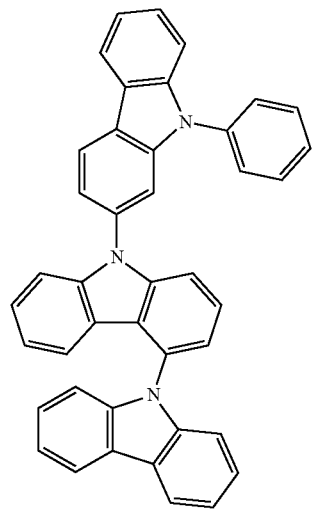
3-6
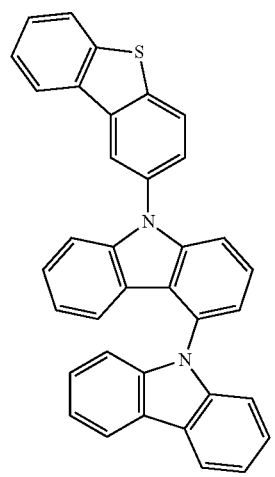
3-7
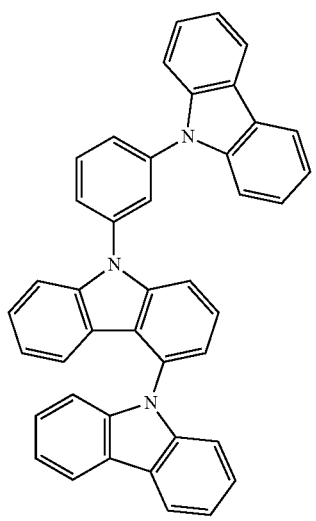
3-8

-continued
3-9
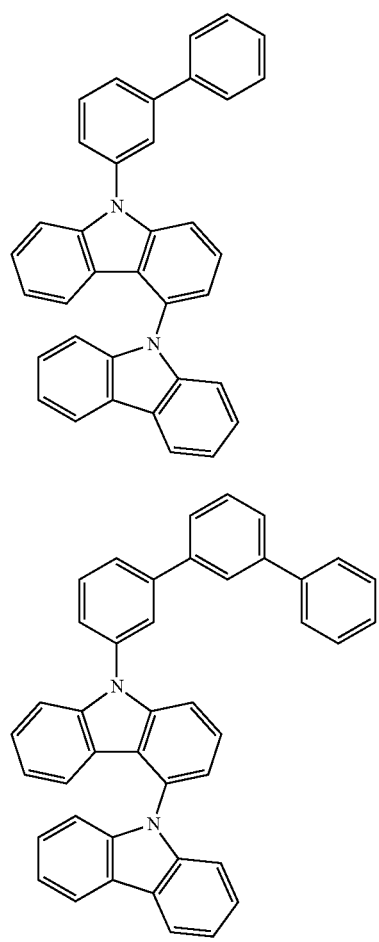
3-10
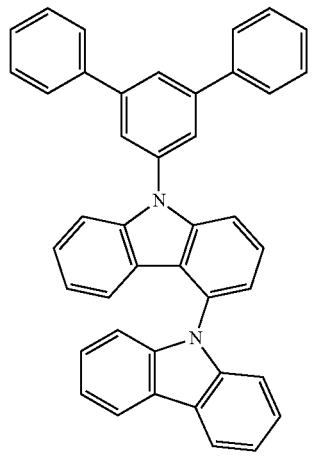
3-11
3-12
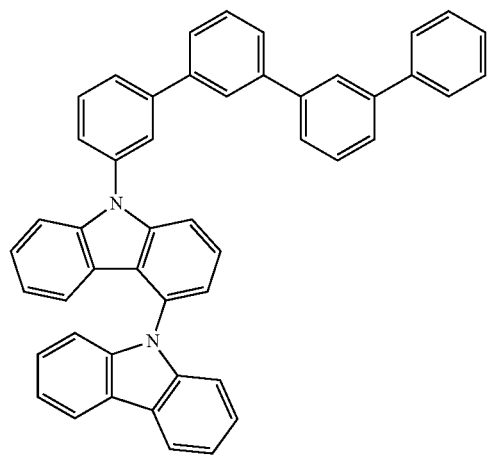
3-13
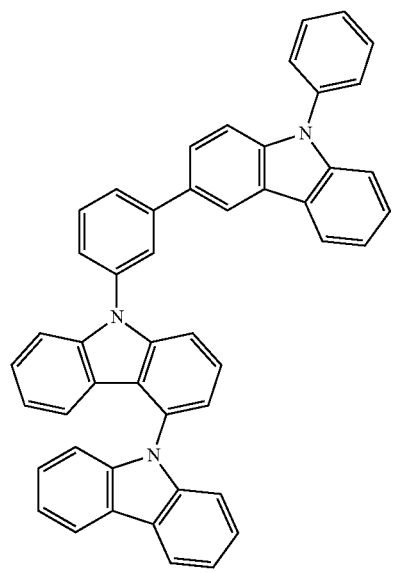
3-14
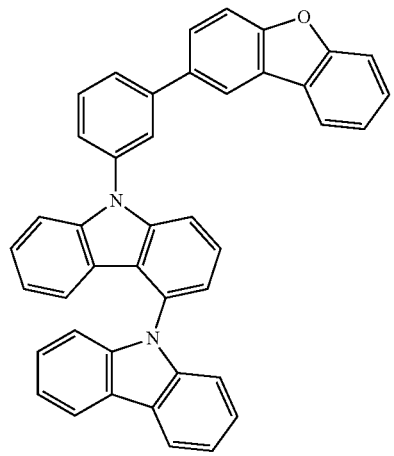

-continued
3-15
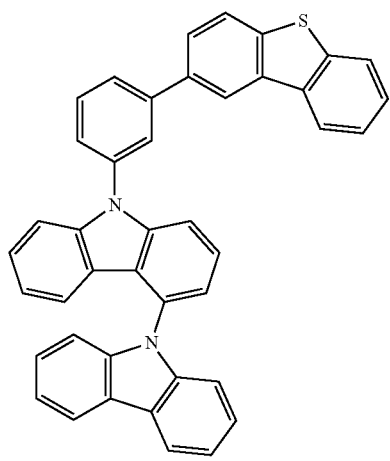
3-16
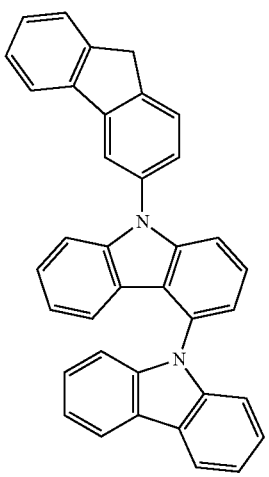
3-17
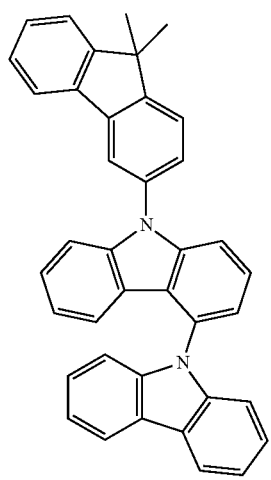
3-18
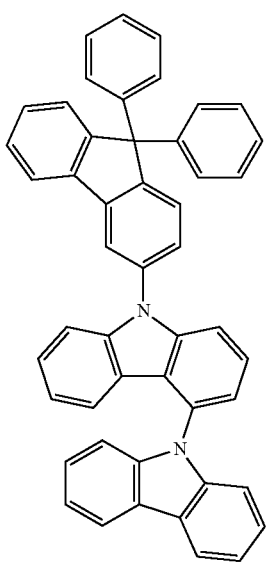
3-19
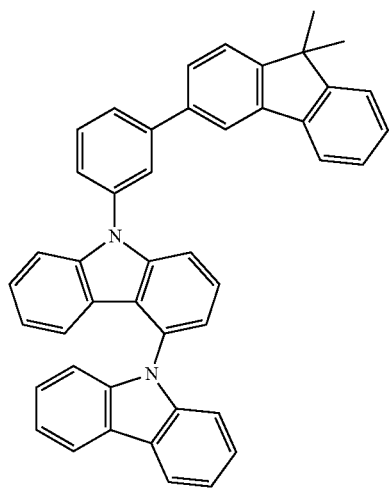
3-19
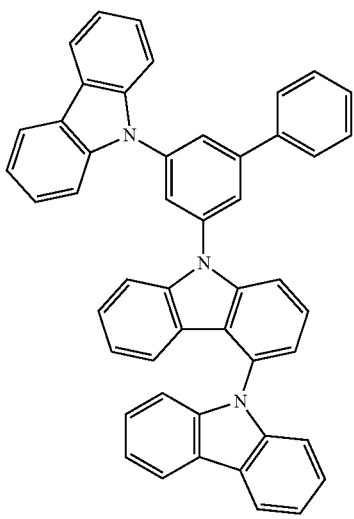

3-20
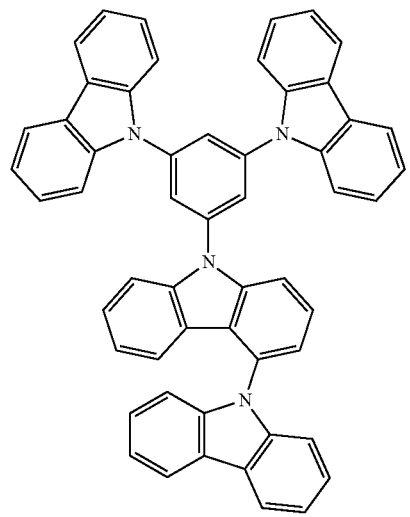
3-21
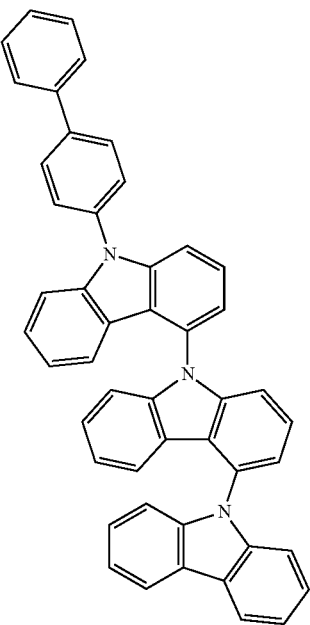
3-22
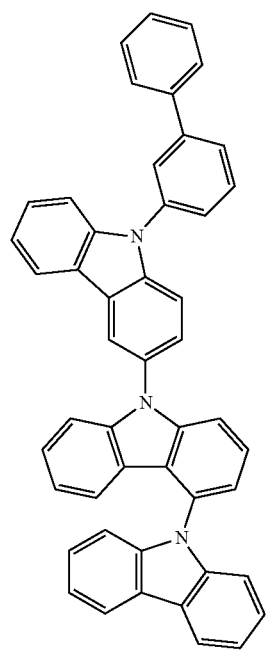
3-23
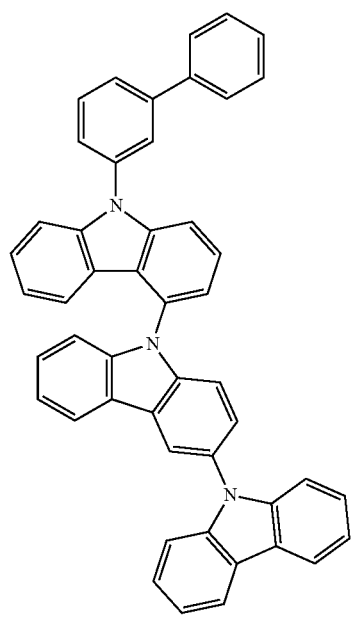

-continued
3-23
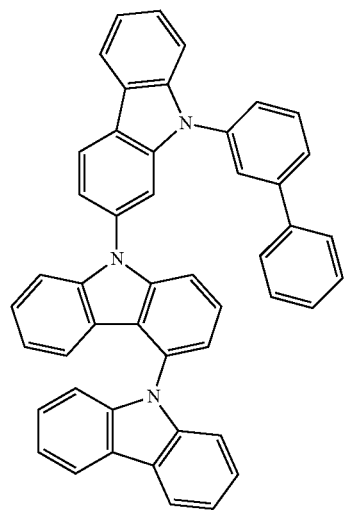
3-24
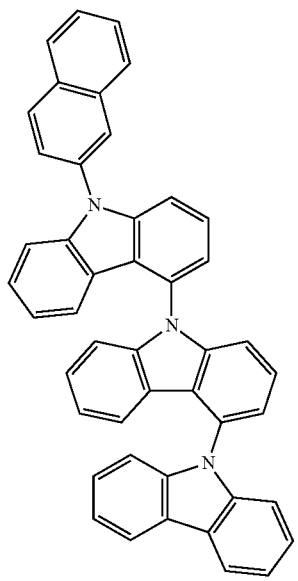
3-25
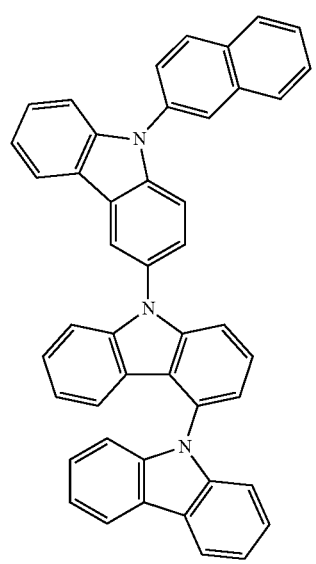
3-26
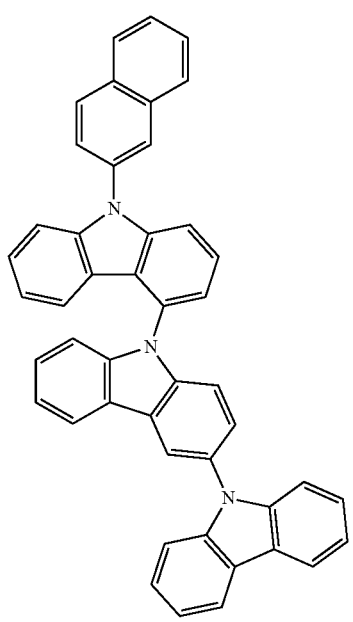

-continued
3-27
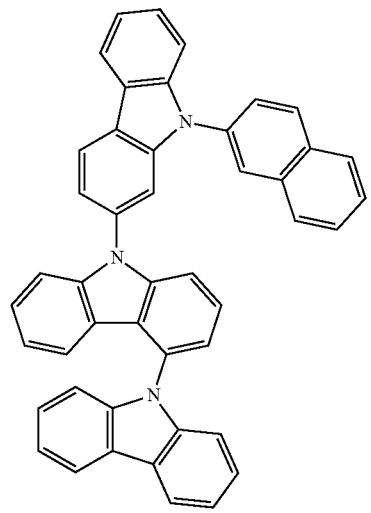
3-28
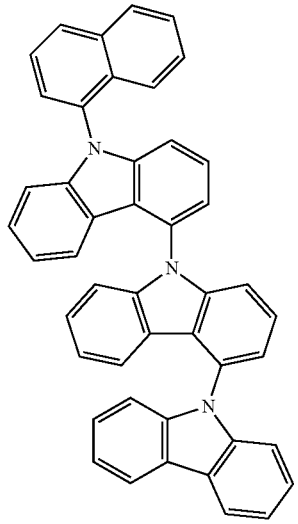
3-29
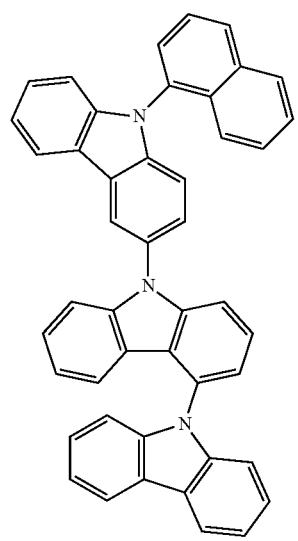
3-30
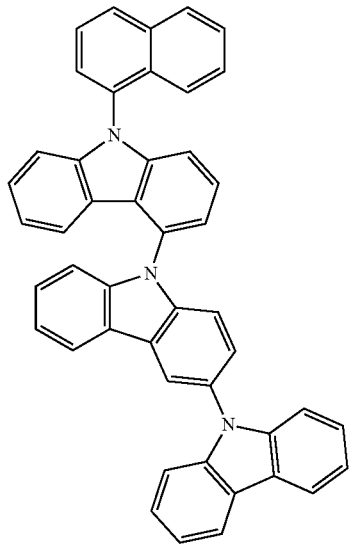

-continued
3-31
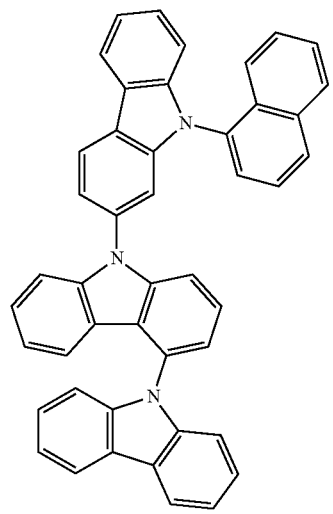
3-32
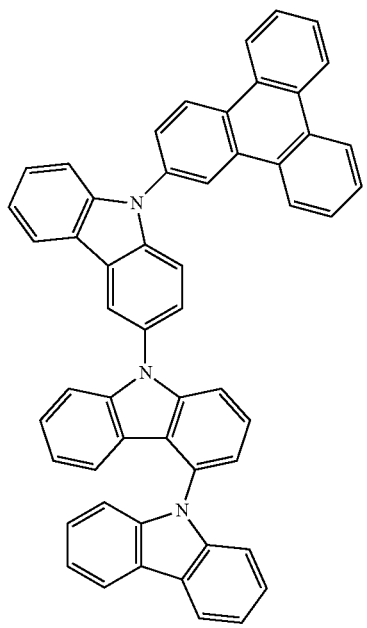
3-33
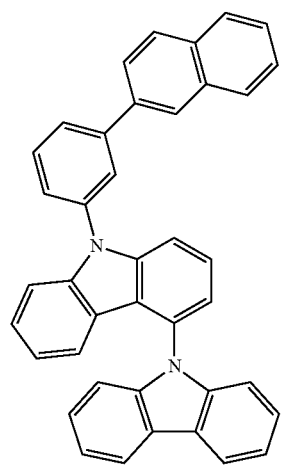
3-34
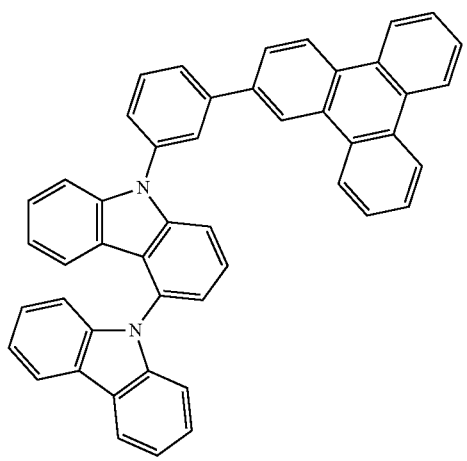
3-35
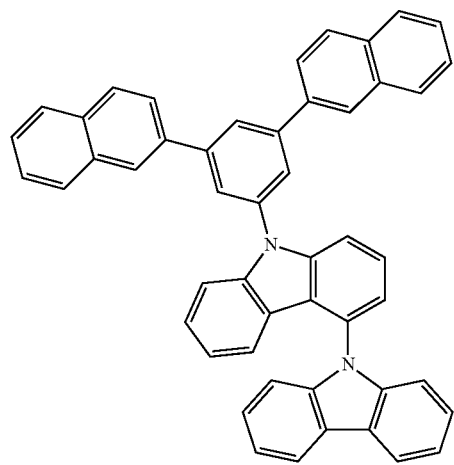
3-36
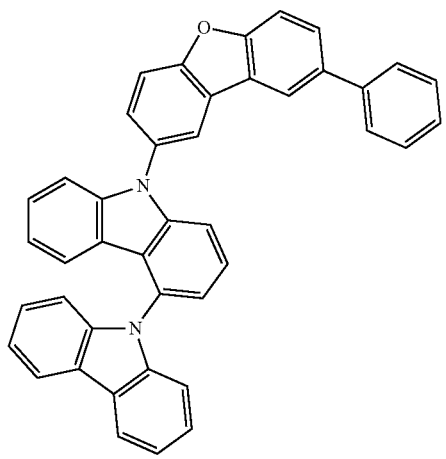

-continued
3-37
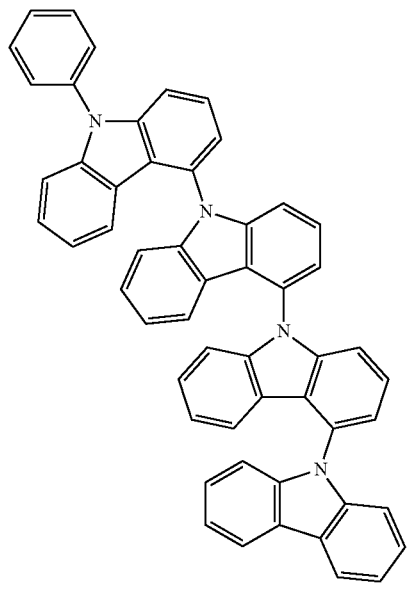
3-38
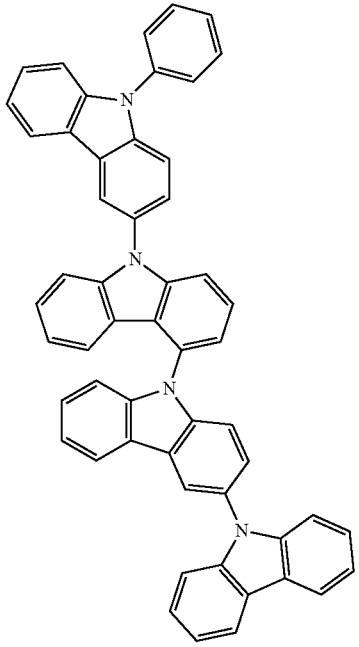
3-39
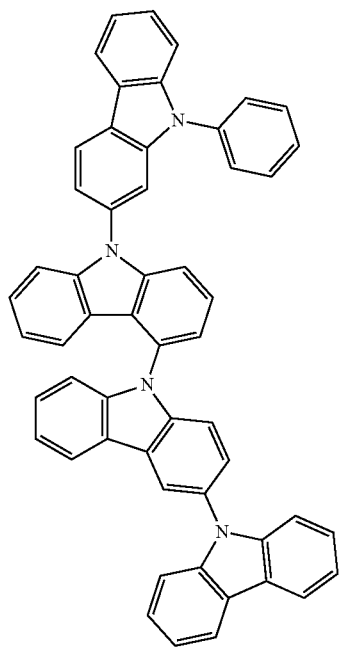
3-40
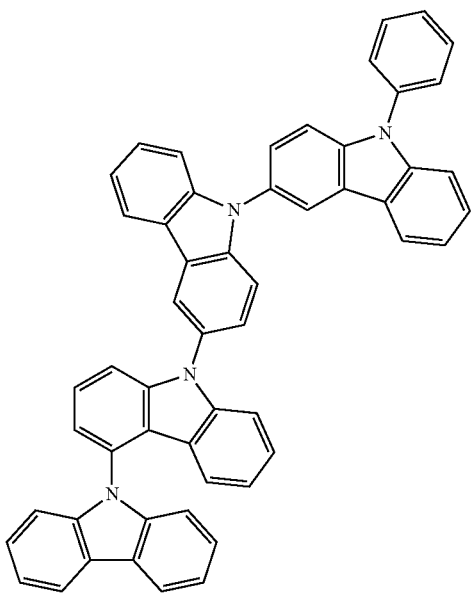

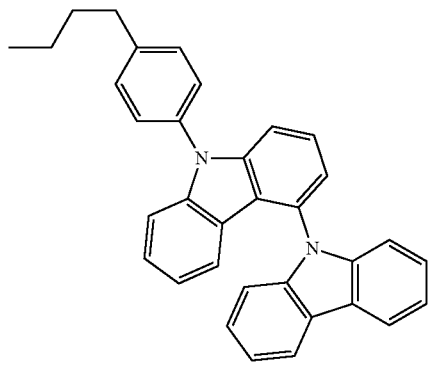
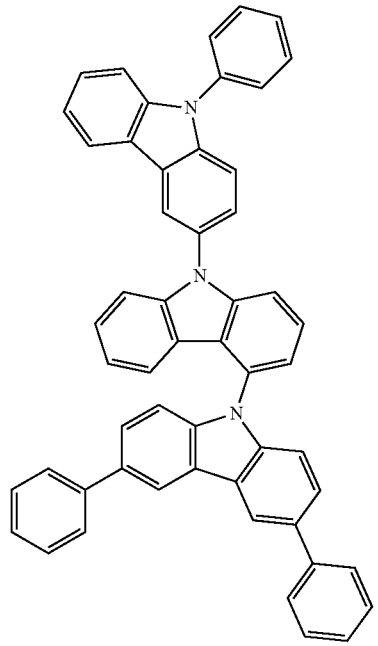
-continued
3-41
3-42
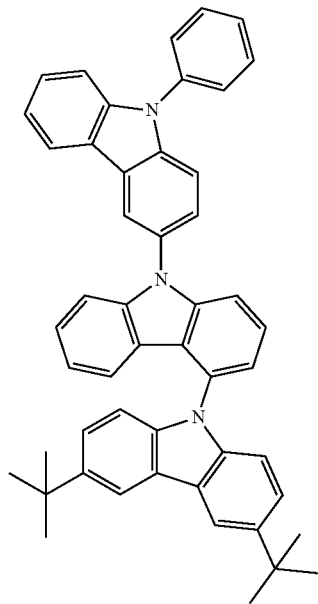
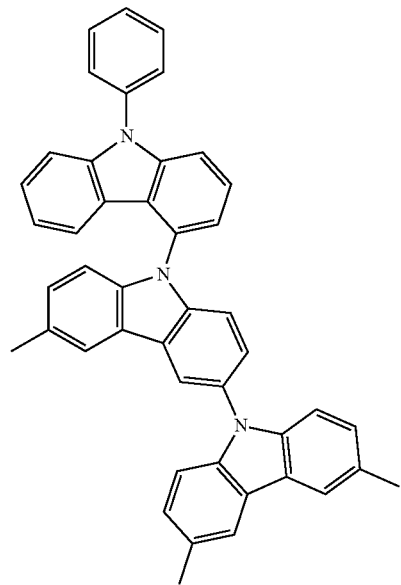
3-43
3-44

-continued
3-45
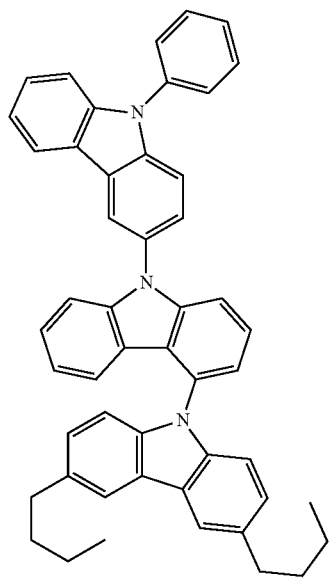
3-46
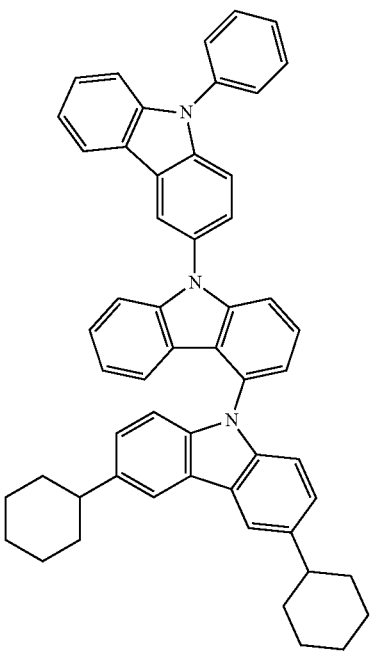
3-47
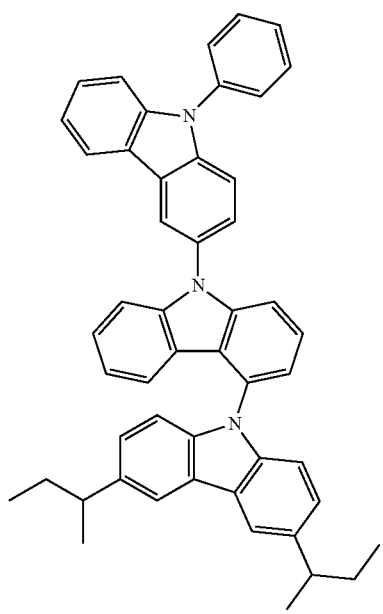
3-48
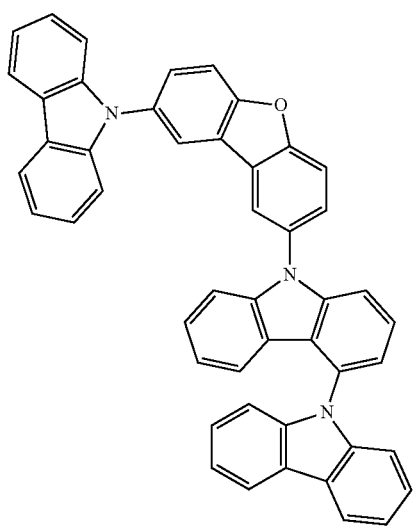

-continued
3-49
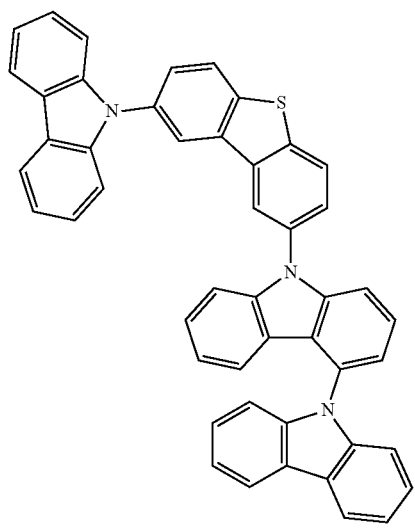
3-50
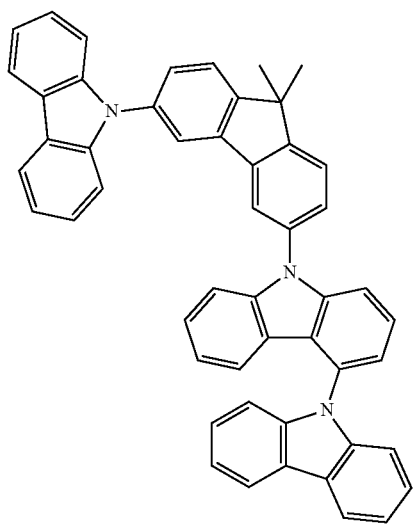
3-51
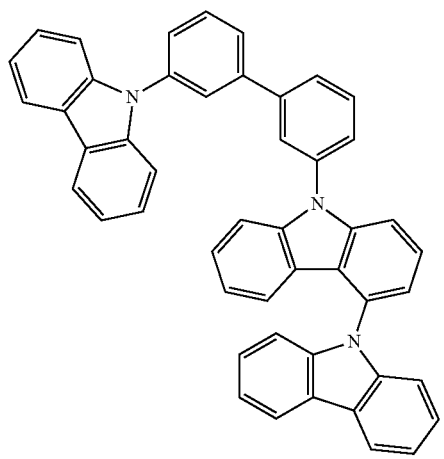
3-52
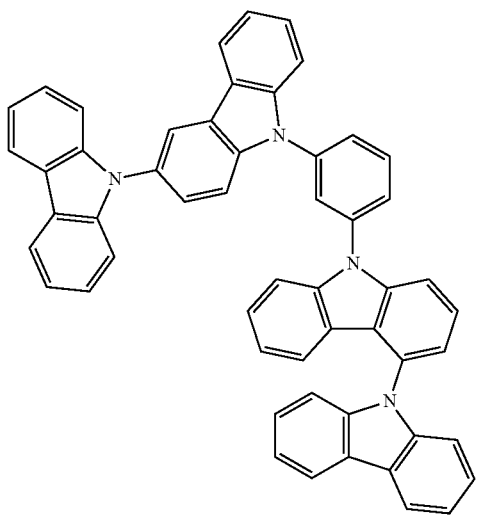
3-53
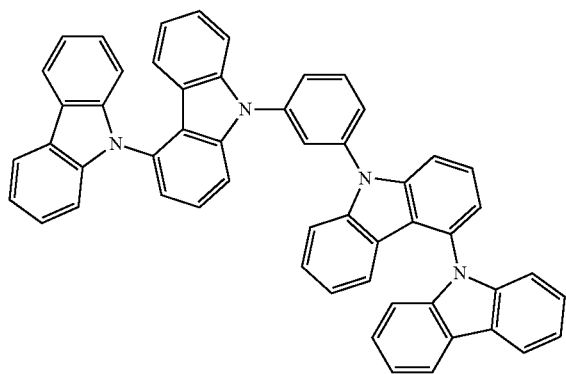
3-54
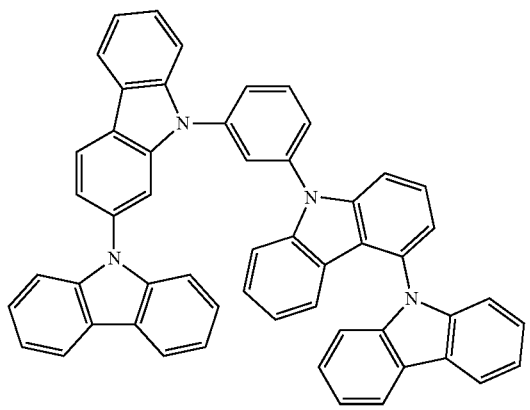

-continued
3-55
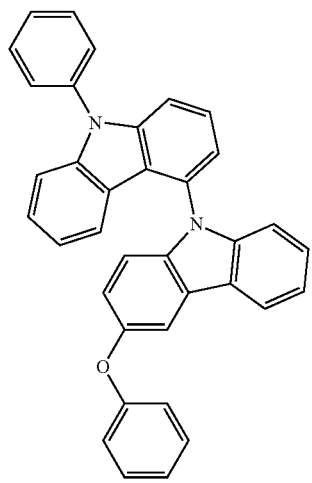
3-56
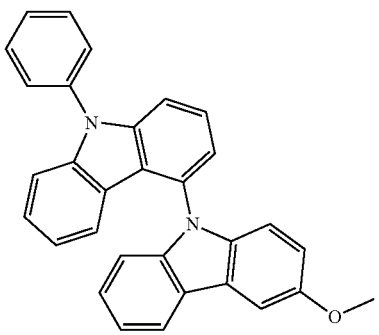
3-57
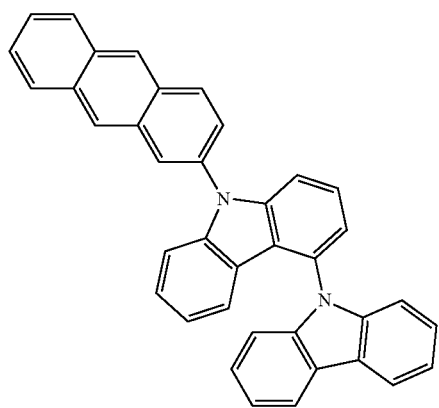
3-58
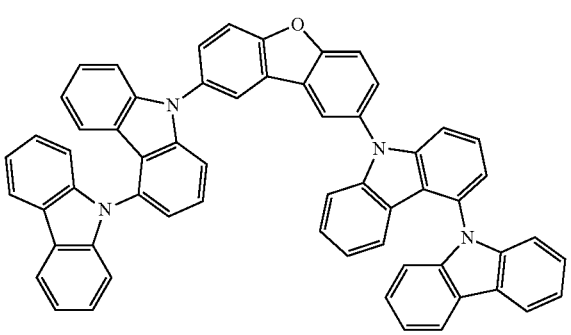
3-59
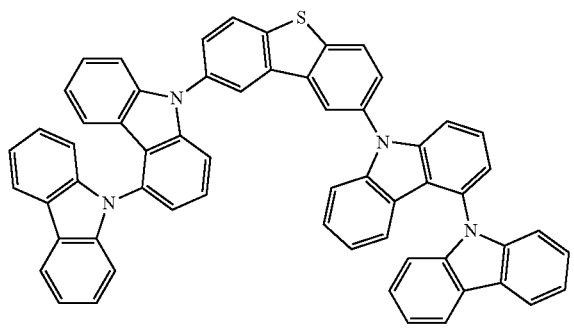
3-60
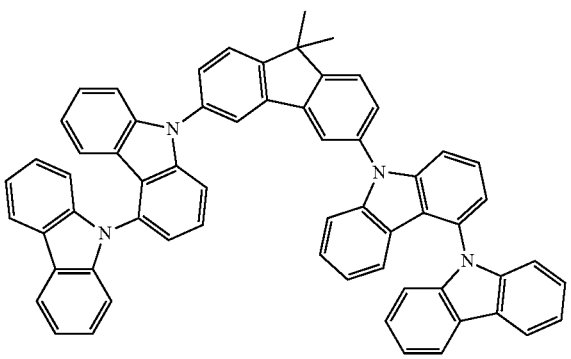

3-61
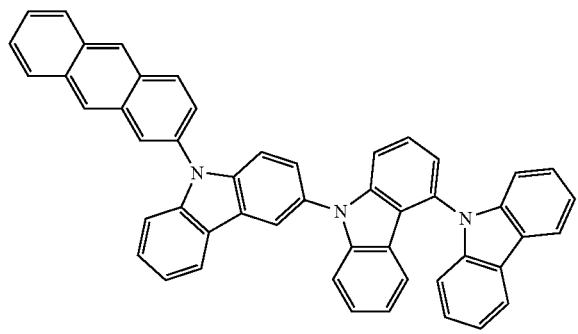
3-62
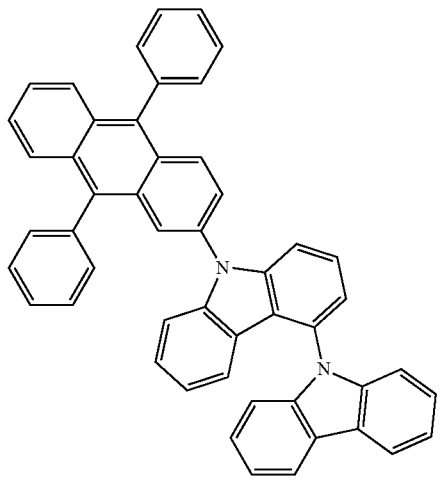
3-63
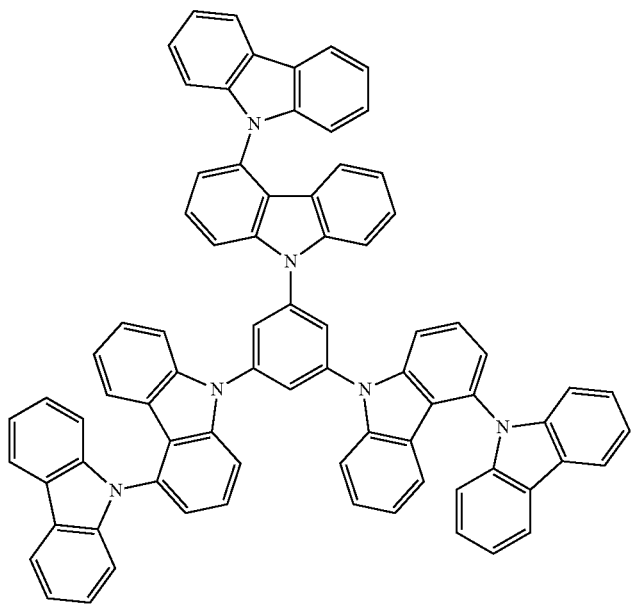
3-64
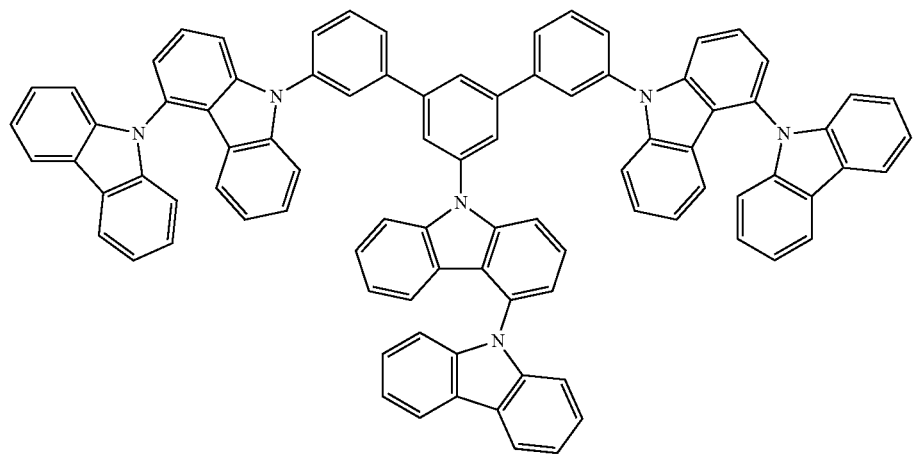

-continued 3-65

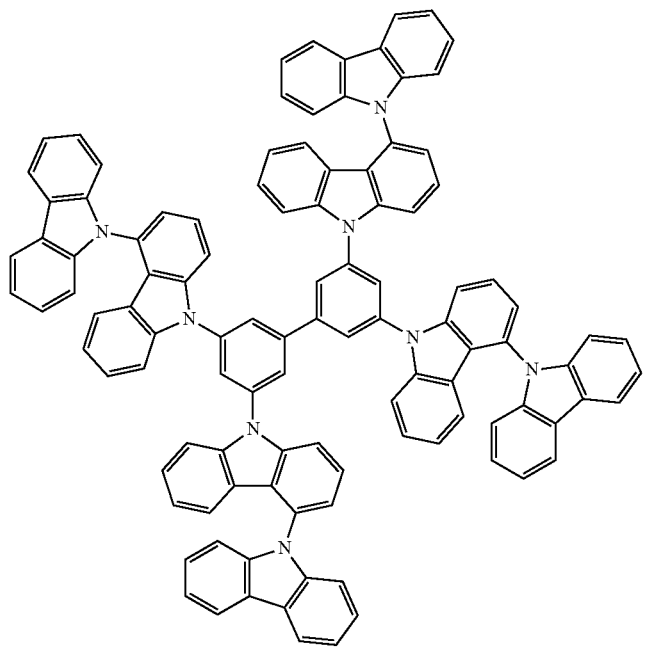

The host materials including the first host material (H1) and the second host material (H2) may be mixed before the production of the device and vapor-deposited by using one vapor deposition source, or may be mixed at the time of the production of the device by an operation, such as co-deposition involving using a plurality of vapor deposition sources. A mixing ratio (weight ratio) between the host materials, which is not particularly limited, preferably falls within the range of from 95:5 to 5:95.

Next, the structure of the organic EL device of the present invention is described with reference to the drawings. However, the structure of the organic EL device of the present invention is by no means limited to one illustrated in the drawings.

(1) Construction of Organic EL Device

FIG. 1 is a sectional view for schematically illustrating a structure example of a general organic EL device. Reference numeral 1 represents a substrate, reference numeral 2 represents an anode, reference numeral 3 represents a hole-injecting layer, reference numeral 4 represents a hole-transporting layer, reference numeral 5 represents a light-emitting layer, reference numeral 6 represents an electron-transporting layer, reference numeral 7 represents an electron-injecting layer, and reference numeral 8 represents a cathode. The organic EL device of the present invention includes the anode, the light-emitting layer, and the cathode as its essential layers, and may include any other layer as required. Examples of the other layer include, but not limited to, a hole-injecting/transporting layer, an electron-blocking layer, and a hole-blocking layer. The hole-injecting/transporting layer means any one or both of the hole-injecting layer and the hole-transporting layer. The organic EL device preferably includes the layers illustrated in FIG. 1 as its essential layers.

(2) Substrate

The substrate 1 serves as a support for the organic electroluminescent device, and a quartz or glass plate, a metal plate or a metal foil, a plastic film or sheet, or the like is used. A glass plate, or a smooth and transparent plate made of a synthetic resin, such as polyester, polymethacrylate, polycarbonate, or polysulfone, is particularly preferred. When a synthetic resin substrate is used, attention needs to be paid to its gas barrier property. The case where the gas barrier property of the substrate is excessively small is not preferred because the organic electroluminescent device may deteriorate owing to outside air that has passed the substrate. Accordingly, a method involving providing at least one surface of the synthetic resin substrate with a dense silicon oxide film or the like to secure the gas barrier property is one preferred method.

(3) Anode

The anode 2 is formed on the substrate 1 and the anode serves to inject a hole into the hole-transporting layer. The anode is typically formed of, for example, a metal, such as aluminum, gold, silver, nickel, palladium, or platinum, a metal oxide, such as an oxide of indium and/or tin, or an oxide of indium and/or zinc, a metal halide, such as copper iodide, carbon black, or a conductive polymer, such as poly(3-methylthiophene), polypyrrole, or polyaniline. The formation of the anode is typically performed by, for example, a sputtering method or a vacuum deposition method in many cases. In addition, in the case of, for example, a metal fine particle made of silver or the like, a fine particle made of copper iodide or the like, carbon black, a conductive metal oxide fine particle, or conductive polymer fine powder, the anode can be formed by dispersing such particle or powder in a proper binder resin solution and applying the dispersion onto the substrate. Further, in the case of a conductive polymer, the anode can be formed by directly forming a thin film of the conductive polymer on the substrate through electrolytic polymerization or by applying the conductive polymer onto the substrate 1. The anode can also be formed by laminating different substances. The thickness of the anode varies depending on transparency to be required. When the transparency is required, the visible light transmittance of the anode is desirably set to 60% or more, preferably 80% or more in ordinary cases. In such cases, the thickness is typically from about 5 nm to about 1,000 nm, preferably from about 10 nm to about 500 nm. When the anode may be opaque, the anode may have be the same transmittance material as that of the substrate. In addition, another conductive material can be further laminated on the anode.

(4) Hole-Transporting Layer

The hole-transporting layer 4 is formed on the anode 2. The hole-injecting layer 3 can be formed therebetween. A material for the hole-transporting layer is required to satisfy the following conditions: the material needs to have high efficiency with which a hole is injected from the anode and be capable of efficiently transporting the injected hole. To this end, the material is required to have a small ionization potential, have high transparency for visible light, have a large hole mobility, be excellent in stability, and hardly produce an impurity serving as a trap at the time of the production or use. In addition, the layer is in contact with the light-emitting layer 5, and is hence required neither to quench light emitted from the light-emitting layer nor to form an exciplex between itself and the light-emitting layer to reduce the efficiency. In addition to the above-mentioned general requirements, the device is required to further have heat resistance when its application to anon-vehicle display is considered. Therefore, a material having a Tg of 85° C. or more is desired.

A known compound that has heretofore been used in the layer can be used as a hole-transporting material. Examples thereof include: an aromatic diamine which contains two or more tertiary amines and in which a nitrogen atom is substituted with two or more fused aromatic rings; an aromatic amine compound having a starburst structure, such as 4,4',4"-tris(1-naphthylphenylamino)triphenylamine; an aromatic amine compound formed of a tetramer of triphenylamine; and a spiro compound, such as 2,2',7,7'-tetrakis-(diphenylamino)-9,9'-spirobifluorene. Those compounds may be used alone or as a mixture thereof as required.

In addition, examples of the material for the hole-transporting layer other than the above-mentioned compounds include polymer materials, such as polyvinylcarbazole, polyvinyltriphenylamine, and tetraphenylbenzidine-containing polyarylene ether sulfone.

When the hole-transporting layer is formed by an application method, the hole-transporting layer is formed by: adding and dissolving one or two or more kinds of hole-transporting materials, and as required, an additive that does not serve as a trap for a hole, such as a binder resin or an applicability improver, to prepare an application solution; applying the solution onto the anode by a method such as a spin coating method; and drying the applied solution. Examples of the binder resin include polycarbonate, polyarylate, and polyester. When the binder resin is added in a large amount, a hole mobility reduces. Accordingly, the addition amount is desirably as small as possible and is preferably 50 wt % or less in ordinary cases.

When the hole-transporting layer is formed by the vacuum deposition method, the hole-transporting layer is formed by: loading a hole-transporting material into a crucible placed in a vacuum chamber; evacuating the inside of the vacuum chamber to about 10-4 Pa with a proper vacuum pump; and heating the crucible after the evacuation to evaporate the hole-transporting material. Thus, the hole-transporting layer is formed on the substrate having formed thereon the anode, the substrate being placed to face the crucible. The thickness of the hole-transporting layer is typically from 1 nm to 300 nm, preferably from 5 nm to 100 nm. In general, the vacuum deposition method is frequently employed for uniformly forming such thin film.

(5) Hole-Injecting Layer

The hole-injecting layer 3 has been inserted between the hole-transporting layer 4 and the anode 2 for the purposes of additionally improving the hole injection efficiency and improving the adhesive force of the entire organic layer to the anode. The insertion of the hole-injecting layer provides the following effects: the initial driving voltage of the device reduces, and at the same time, an increase in voltage when the device is continuously driven at a constant current is suppressed. A material to be used in the hole-injecting layer is required to satisfy the following conditions: the material can be formed into a uniform thin film, which can be satisfactorily brought into contact with the anode, and is thermally stable, i.e., has a high glass transition temperature. The material is required to have a glass transition temperature of 100° C. or more. Further, the material is required to satisfy, for example, the following conditions: the material has a low ionization potential and hence facilitates the injection of a hole from the anode; and the material has a large hole mobility.

For this purpose, the following materials have been reported hitherto: a phthalocyanine compound, such as copper phthalocyanine, an organic compound, such as polyaniline or polythiophene, a sputtered carbon film, a metal oxide, such as a vanadium oxide, a ruthenium oxide, or a molybdenum oxide, and a P-type organic substance, such as 1,4,5,8-naphthalenetetracarboxylic dianhydride (NTCDA) or hexanitrilehexaazatriphenylene (HAT). Those compounds may be used alone or as a mixture thereof as required. A thin film serving as the hole-injecting layer can be formed as in the hole-transporting layer. In the case of inorganic matter, however, the sputtering method, an electron beam deposition method, or a plasma CVD method is further employed. The thickness of the hole-injecting layer to be formed as described above is typically from 1 nm to 300 nm, preferably from 5 nm to 100 nm.

(6) Light-Emitting Layer

The light-emitting layer 5 is formed on the hole-transporting layer 4. The light-emitting layer may be formed of a single light-emitting layer, or may be formed by laminating a plurality of light-emitting layers so that the layers may be in direct contact with each other. The light-emitting layer contains a host material and a light-emitting dopant. The light-emitting dopant comes in a fluorescent light-emitting material, a delayed fluorescent light-emitting material, and a phosphorescent light-emitting material. Two or more kinds of light-emitting dopants may be used in combination.

The host material contains the first host material (H1) selected from compounds each represented by any one of the general formulae (1) and (2), and the second host material (H2) selected from compounds each represented by the general formula (3). It is preferred that a compound represented by the general formula (1) or (2) be used as the first host material, and a compound represented by the general formula (3) be used as the second host material. Those compounds may contain two or more compounds included in the formulae.

A usage ratio (weight ratio) "H1;H2" between the first host material (H1) and the second host material (H2) falls within the range of preferably from 10:90 to 90:10, more preferably from 20:80 to 80:20.

The first host material (H1) and the second host material (H2) can be preliminarily mixed and vapor-deposited from one evaporation source (preliminary mixing evaporation). When the first host material (H1) and the second host material (H2) are preliminarily mixed, the usage ratio (mixing ratio) between the H1 and the H2 preferably changes by an amount within 5% relative to a preliminary mixing ratio therebetween before the vapor deposition. The change amount is determined from a difference between: the preliminary mixing ratio between the H1 or the H2 before the vapor deposition; and the mixing ratio of a deposited product.

When the first host material (H1) and the second host material (H2) are preliminarily mixed and vapor-deposited, a difference in vaporization temperature (including evaporation and sublimation) between the H1 and the H2 is preferably within 30° C., more preferably within 10° C.

In the case of a fluorescent organic EL device, a fused ring derivative, such as perylene or rubrene, a quinacridone derivative, phenoxazone 660, DCM1, perinone, a coumarin derivative, a pyrromethene (diazaindacene) derivative, a cyanine dye, or the like can be used as the fluorescent light-emitting material to be added to the host material.

In the case of a delayed fluorescent organic EL device, examples of the delayed fluorescent light-emitting material in the light-emitting layer include a carborane derivative, a tin complex, an indolocarbazole derivative, a copper complex, and a carbazole derivative. Specific examples thereof include the compounds disclosed in the following literatures, but are not limited to these compounds.

1) Adv. Mater. 2009, 21, 4802-4806, 2) Appl. Phys. Lett. 98, 083302 (2011), 3) JP 2011-213643 A, 4) J. Am. Chem. Soc. 2012, 134, 14706-14709.

Specific examples of the delayed light-emitting material are shown, but the material is not limited to the compounds shown below.

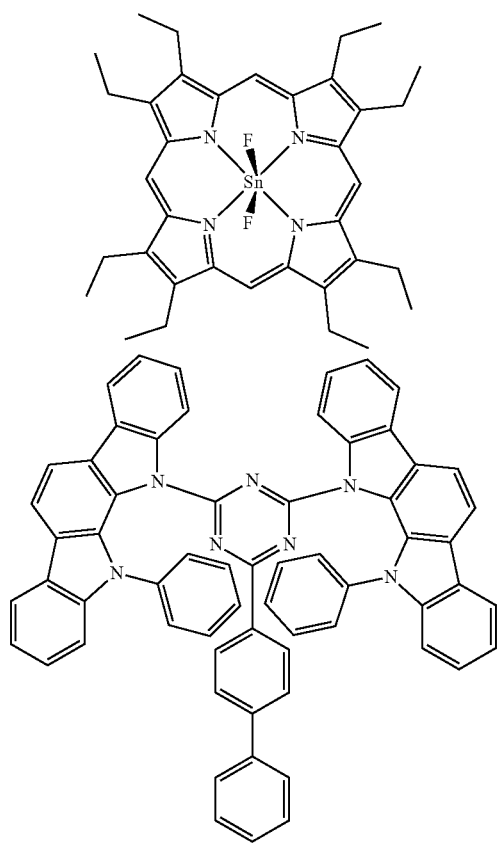

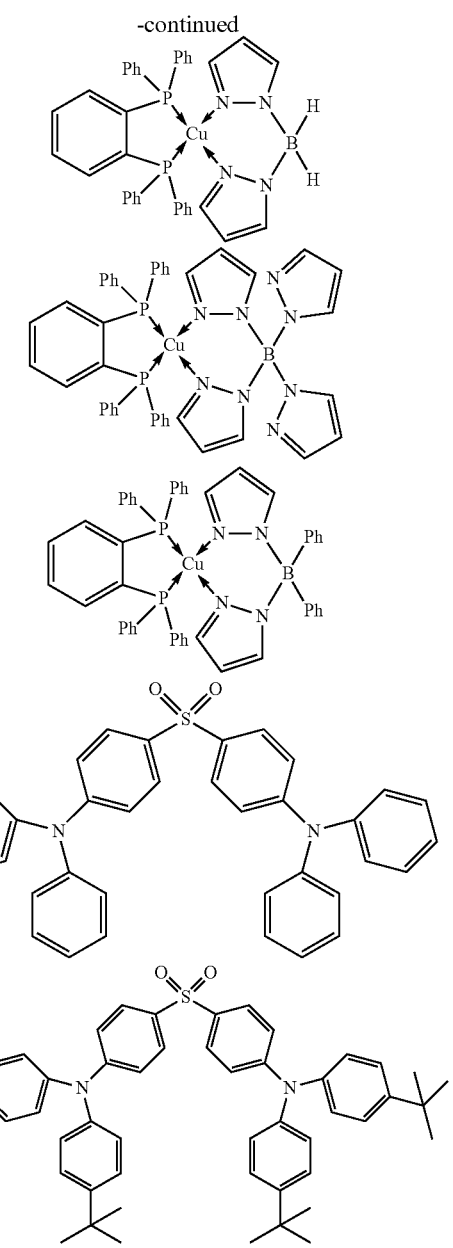

When the delayed fluorescent light-emitting material is used as a delayed fluorescent light-emitting dopant, and the light-emitting layer contains the host material, it is desired that the content of the delayed fluorescent light-emitting dopant in the light-emitting layer fall within the range of from 0.01 wt % to 50 wt %, preferably from 0.1 wt % to 20 wt %, more preferably from 0.01% to 10%.

In the case of a phosphorescent organic EL device, it is recommended to use, as the phosphorescent light-emitting dopant, a material containing an organometallic complex containing at least one metal selected from, for example, ruthenium, rhodium, palladium, silver: rhenium, osmium, iridium, platinum, and gold. Specific examples thereof include, but not limited to, the compounds disclosed in the following patent publications.

For example, WO 2009/073245 A1, WO 2009/046266 A1, WO 2007/095118A2, WO2008/156879A1, WO2008/140657A1, US 2008/261076 A1, JP 2008-542203 A, WO 2008/054584 A1, JP 2008-505925 A, JP 2007-522126 A, JP 2004-506305 A, JP 2006-513278 A, JP 2006-50596 A, WO 2006/046980 A1, WO 2005/113704 A2, US 2005/260449 A1, US 2005/2260448 A1, US 2005/214576 A1, and WO 2005/076380 A2.

Preferred examples of the phosphorescent light-emitting dopant include complexes such as Ir(ppy)3, complexes such as Ir(bt)2·acac3, and complexes such as PtOEt3, the complexes each having a noble metal element such as Ir as a central metal. Specific examples of those complexes are shown below, but the complexes are not limited to the compounds shown below.

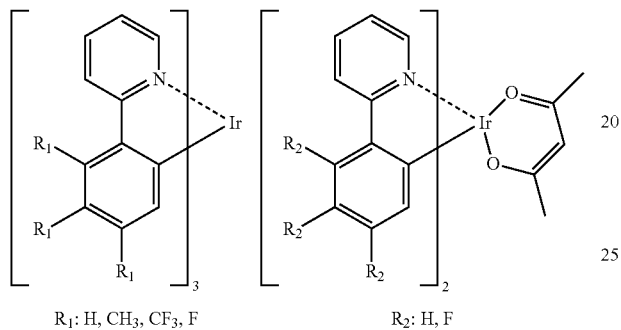

R₁: H, CH₃, CF₃, F          R₂: H, F

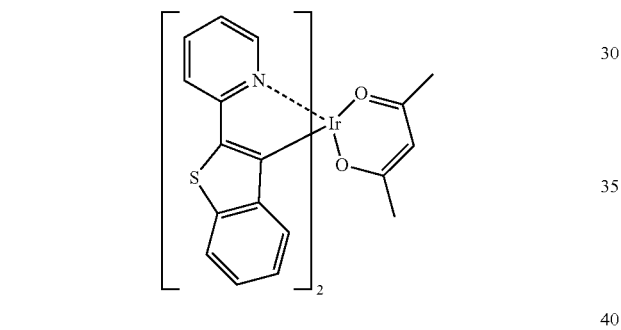

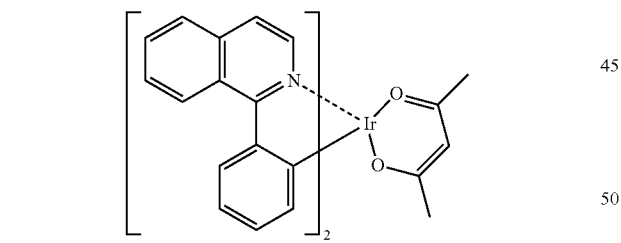

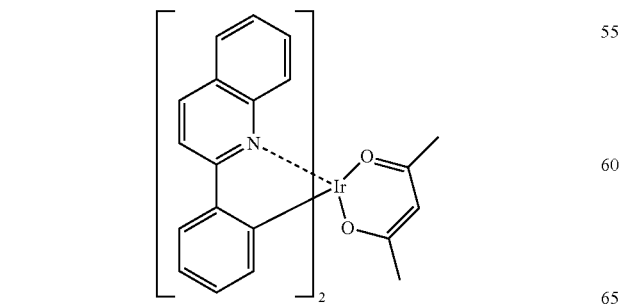

-continued

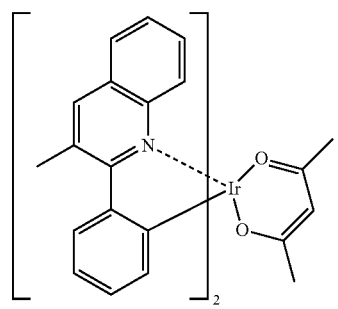

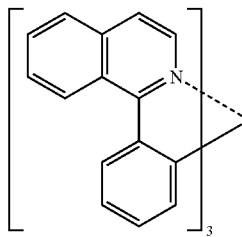

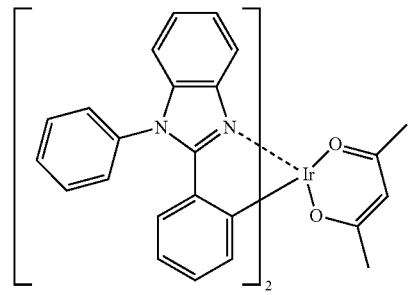

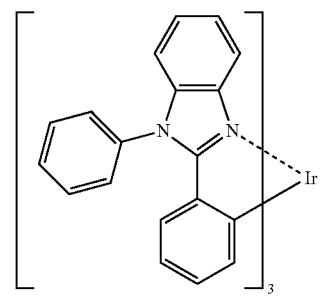

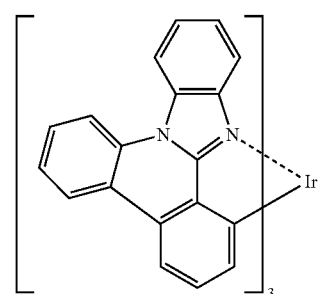

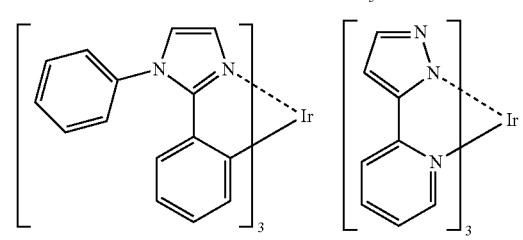

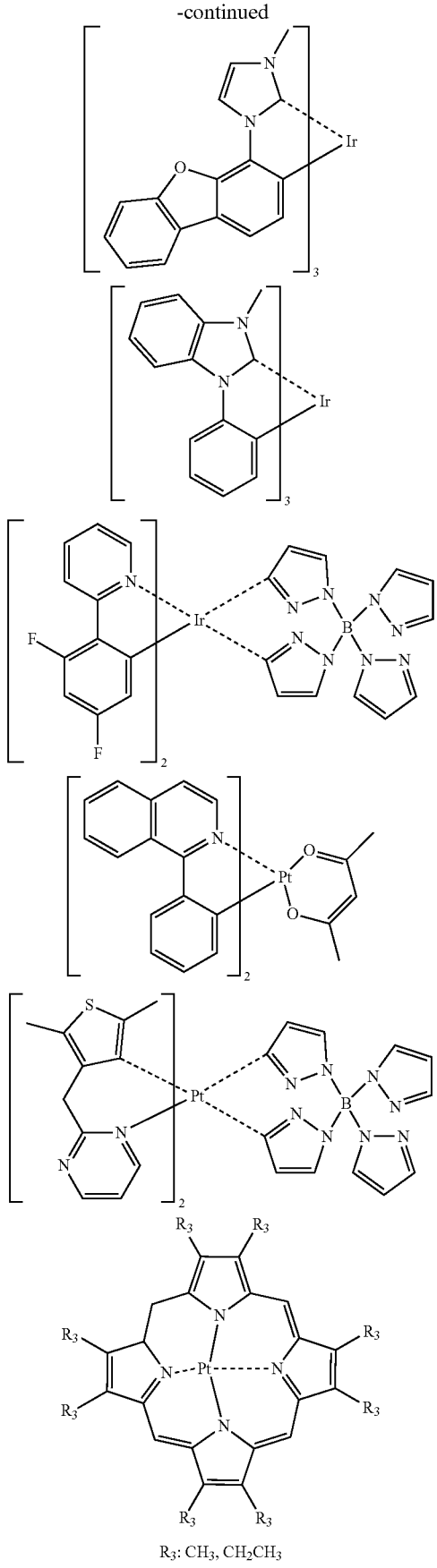

It is desired that the content of the phosphorescent light-emitting dopant in the light-emitting layer fall within the range of from 2 wt % to 40 wt %, preferably from 5 wt % to 30 wt %.

The thickness of the light-emitting layer, which is not particularly limited, is typically from 1 nm to 300 nm, preferably from 5 nm to 100 nm, and a thin film serving as the layer is formed by the same method as that for the hole-transporting layer.

(7) Electron-Transporting Layer

The electron-transporting layer 6 is formed between the light-emitting layer 5 and the cathode 8 for the purpose of additionally improving the luminous efficiency of the device. A material for the electron-transporting layer is preferably an electron-transportable material that enables smooth injection of an electron from the cathode, and an arbitrary material that has been generally used can be used. Examples of the electron-transporting material that satisfies such condition include a metal complex, such as Alq3, a metal complex of 10-hydroxybenzo[h]quinoline, an oxadiazole derivative, a distyrylbiphenyl derivative, a silole derivative, a 3- or 5-hydroxyflavone metal complex, a benzoxazole metal complex, a benzothiazole metal complex, trisbenzimidazolylbenzene, a quinoxaline compound, a phenanthroline derivative, 2-t-butyl-9,10-N,N'-dicyanoanthraquinonediimine, n-type hydrogenated amorphous silicon carbide, n-type zinc sulfide, and n-type zinc selenide.

The thickness of the electron-transporting layer is typically from 1 nm to 300 nm, preferably from 5 nm to 100 nm. The electron-transporting layer is formed through lamination on the light-emitting layer by the application method or the vacuum deposition method as in the hole-transporting layer. The vacuum deposition method is typically employed.

(8) Cathode

The cathode 8 serves to inject an electron into the electron-transporting layer 6. Although the material to be used in the anode 2 can be used as a material to be used as the cathode, a metal having a low work function is preferred for efficient electron injection, and a proper metal, such as tin, magnesium, indium, calcium, aluminum, or silver, or an alloy thereof is used. Specific examples of the cathode include low-work function alloy electrodes made of a magnesium-silver alloy, a magnesium-indium alloy, and an aluminum-lithium alloy.

The thickness of the cathode is typically the same as that of the anode. When a metal layer that has a high work function and is stable against the air is further laminated on the cathode formed of a low-work function metal for the purpose of protecting the cathode, the stability of the device improves. A metal, such as aluminum, silver, copper, nickel, chromium, gold, or platinum, is used for the purpose.

Further insertion of an extremely thin insulating film (having a thickness of from 0.1 nm to 5 nm) made of LiF, $MgF_2$, $Li_2O$, or the like as the electron-injecting layer 7 between the cathode 8 and the electron-transporting layer 6 is also an effective method of improving the efficiency of the device.

A structure in inverse relation to that illustrated in FIG. 1 is permitted, i.e., the cathode 8, the electron-injecting layer 7, the electron-transporting layer 6, the light-emitting layer 5, the hole-transporting layer 4, the hole-injecting layer 3, and the anode 2 can be laminated in the stated order on the substrate 1. In this case as well, a layer can be added or omitted as required.

The organic EL device of the present invention can be any one of a single device, a device formed of structures arranged in an array manner, and a structure in which the anode and the cathode are arranged in an X-Y matrix manner. According to the organic EL device of the present invention, when the light-emitting layer is formed by using a mixed host formed of two host materials, and a specific compound is used as at least one of the host materials, a device that has high luminous efficiency and is significantly improved in driving stability while being capable of being driven at a low voltage is obtained, and the device can exhibit excellent performance in its application to a full-color or multi-color panel.

EXAMPLES

The present invention is described in more detail below by way of Examples. However, the present invention is not limited to Examples below, and can be carried out in various modes as long as the modes do not deviate from the gist thereof.

Example 1

Each thin film was laminated by a vacuum deposition method at a degree of vacuum of $2.0 \times 10^{-5}$ Pa on a glass substrate on which an anode formed of indium tin oxide (ITO) having a thickness of 70 nm had been formed. First, copper phthalocyanine (CuPC) was formed into a hole-injecting layer having a thickness of 30 nm on the ITO. Next, 4,4-bis[N-(l-naphthyl)-N-phenylamino]biphenyl (NPB) was formed into a hole-transporting layer having a thickness of 15 nm. Next, Compound 1-30 serving as a first host (H1), Compound 3-2 serving as a second host (H2), and an iridium complex [iridium(III) bis(4,6-difluorophenyl)-pyridinato-N,C2'] picolinate (FIrpic) which is a blue phosphorescent material, serving as a light-emitting layer guest (dopant) were co-deposited from vapor deposition sources different from one another to form a light-emitting layer having a thickness of 30 nm. At this time, a vapor deposition rate ratio among the first host, the second host, and FIrpic was 47:47:6. Next, $Alq_3$ was formed into an electron-transporting layer having a thickness of 25 nm. Further, lithium fluoride (LiF) was formed into an electron-injecting layer having a thickness of 1.0 nm on the electron-transporting layer. Finally, aluminum (Al) was formed into an electrode having a thickness of 70 nm on the electron-injecting layer. Thus, an organic EL device was produced.

Examples 2 to 11

Organic EL devices were each produced in the same manner as in Example 1 except that a compound shown in Table 1 was used as the second host of the light-emitting layer.

Examples 12 to 24

Organic EL devices were each produced in the same manner as in Example 1 except that: Compound 1-99 was used as the first host of the light-emitting layer; and a compound shown in Table 1 was used as the second host thereof.

Example 25

An organic EL device was produced in the same manner as in Example 1 except that: Compound 1-91 was used as the first host of the light-emitting layer; and Compound 3-3 was used as the second host thereof.

Example 26

An organic EL device was produced in the same manner as in Example 25 except that the first host and second host of the light-emitting layer were preliminarily mixed and vapor-deposited from one evaporation source.

An external power source was connected to each of the resultant organic EL devices to apply a DC voltage thereto. As a result, an emission spectrum having a local maximum wavelength of 475 nm from each of the organic EL devices was observed, and hence it was found that light emission from FIrpic was obtained. The characteristics of the produced organic EL devices are shown in Table 1.

Comparative Examples 1 to 15

Organic EL devices were each produced in the same manner as in Example 1 except that a compound shown in Table 2 was used alone as the light-emitting layer host. A host amount was set to the same amount as the total of the first host and second host in Example 1, and a guest amount was similarly set. A power source was connected to each of the resultant organic EL devices to apply a DC voltage thereto. As a result, an emission spectrum having a local maximum wavelength of 475 nm from each of the organic EL devices was observed, and hence it was found that light emission from FIrpic was obtained. The characteristics of the produced organic EL devices are shown in Table 2.

In each of Tables 1 and 2, luminance, a voltage, and luminous efficiency are values at a driving current of 2.5 $mA/cm^2$, and a luminance half time is a value at an initial luminance of 1,000 $cd/m^2$. Compound Nos. are numbers attached to the chemical formulae. H1 means the first host and H2 means the second host. The same holds true for Table 3 and subsequent tables unless otherwise stated.

TABLE 1

| Example | H1 Compound No. | H2 Compound No. | Luminance (cd/m$^2$) | Voltage (V) | Visual luminous efficiency (lm/W) | Luminance half time (h) |
|---|---|---|---|---|---|---|
| 1 | 1-30 | 3-2 | 560 | 8.0 | 8.8 | 3,000 |
| 2 | 1-30 | 3-3 | 560 | 8.9 | 7.9 | 3,000 |
| 3 | 1-30 | 3-4 | 564 | 8.9 | 8.0 | 3,000 |
| 4 | 1-30 | 3-5 | 543 | 8.8 | 7.7 | 3,000 |
| 5 | 1-30 | 3-6 | 558 | 8.0 | 8.8 | 2,500 |
| 6 | 1-30 | 3-8 | 564 | 8.9 | 8.0 | 3,000 |
| 7 | 1-30 | 3-10 | 558 | 8.4 | 8.4 | 3,000 |
| 8 | 1-30 | 3-13 | 557 | 8.6 | 8.2 | 3,000 |
| 9 | 1-30 | 3-17 | 535 | 8.4 | 8.0 | 2,000 |
| 10 | 1-30 | 3-22 | 560 | 8.6 | 8.2 | 3,000 |
| 11 | 1-30 | 3-38 | 560 | 8.9 | 7.9 | 3,000 |
| 12 | 1-99 | 3-52 | 557 | 8.9 | 7.9 | 2,000 |
| 13 | 1-99 | 3-2 | 520 | 8.0 | 8.2 | 2,400 |
| 14 | 1-99 | 3-3 | 520 | 8.9 | 7.4 | 2,400 |
| 15 | 1-99 | 3-4 | 523 | 8.9 | 7.4 | 2,400 |
| 16 | 1-99 | 3-5 | 504 | 8.8 | 7.2 | 2,400 |
| 17 | 1-99 | 3-6 | 518 | 8.0 | 8.1 | 2,000 |
| 18 | 1-99 | 3-8 | 523 | 8.9 | 7.4 | 2,400 |
| 19 | 1-99 | 3-10 | 518 | 8.4 | 7.8 | 2,400 |
| 20 | 1-99 | 3-13 | 518 | 8.6 | 7.6 | 2,400 |
| 21 | 1-99 | 3-17 | 497 | 8.4 | 7.5 | 1,600 |
| 22 | 1-99 | 3-22 | 520 | 8.6 | 7.6 | 2,400 |
| 23 | 1-99 | 3-38 | 520 | 8.9 | 7.4 | 2,400 |
| 24 | 1-99 | 3-52 | 517 | 8.9 | 7.3 | 1,600 |
| 25 | 1-91 | 3-3 | 560 | 9.8 | 7.2 | 2,300 |
| 26 | 1-91 | 3-3 | 550 | 9.7 | 7.1 | 2,300 |

TABLE 2

| Comparative Example | Host Compound No. | Luminance (cd/m$^2$) | Voltage (V) | Visual luminous efficiency (lm/W) | Luminance half time (h) |
|---|---|---|---|---|---|
| 1 | 1-30 | 380 | 8.5 | 5.6 | 600 |
| 2 | 1-91 | 378 | 10.0 | 4.8 | 480 |
| 3 | 1-99 | 376 | 9.0 | 5.2 | 600 |
| 4 | 3-2 | 400 | 9.0 | 5.6 | 600 |
| 5 | 3-3 | 400 | 9.9 | 5.1 | 600 |
| 6 | 3-4 | 403 | 9.9 | 5.1 | 600 |
| 7 | 3-5 | 388 | 9.8 | 5.0 | 600 |
| 8 | 3-6 | 399 | 9.0 | 5.6 | 500 |
| 9 | 3-8 | 403 | 9.9 | 5.1 | 600 |
| 10 | 3-10 | 398 | 9.4 | 5.3 | 600 |
| 11 | 3-13 | 398 | 9.6 | 5.2 | 600 |
| 12 | 3-17 | 382 | 9.4 | 5.1 | 400 |
| 13 | 3-22 | 400 | 9.6 | 5.2 | 600 |
| 14 | 3-38 | 400 | 9.9 | 5.1 | 600 |
| 15 | 3-52 | 398 | 9.9 | 5.1 | 400 |

It is understood from Tables 1 and 2 that each of Examples 1 to 26 is improved in luminance and lifetime characteristic, and hence shows satisfactory characteristics.

Example 27

Each thin film was laminated by a vacuum deposition method at a degree of vacuum of 2.0×10$^{-5}$ Pa on a glass substrate on which an anode formed of indium tin oxide (ITO) having a thickness of 70 nm had been formed. First, CuPC was formed into a hole-injecting layer having a thickness of 30 nm on the ITO. Next, NPB was formed into a hole-transporting layer having a thickness of 15 nm. Next, Compound 2-29 serving as a first host, Compound 3-2 serving as a second host, and FIrpic serving as a light-emitting layer guest were co-deposited from vapor deposition sources different from one another to form a light-emitting layer having a thickness of 30 nm. At this time, a vapor deposition rate ratio among the first host, the second host, and FIrpic was 47:47:6. Next, Alq$_3$ was formed into an electron-transporting layer having a thickness of 25 nm. Further, LiF was formed into an electron-injecting layer having a thickness of 1.0 nm on the electron-transporting layer. Finally, Al was formed into an electrode having a thickness of 70 nm on the electron-injecting layer. Thus, an organic EL device was produced.

Examples 28 to 38

Organic EL devices were each produced in the same manner as in Example 27 except that a compound shown in Table 1 was used as the second host of the light-emitting layer.

An external power source was connected to each of the resultant organic EL devices to apply a DC voltage thereto. As a result, an emission spectrum having a local maximum wavelength of 475 nm from each of the organic EL devices was observed, and hence it was found that light emission from FIrpic was obtained.

Comparative Example 16

An organic EL device was produced in the same manner as in Example 27 except that a compound shown in Table 3 was used alone as the light-emitting layer host. A host amount was set to the same amount as the total of the first host and second host in Example 25, and a guest amount was similarly set. A power source was connected to each of the resultant organic EL devices to apply a DC voltage thereto. As a result, an emission spectrum having a local maximum wavelength of 475 nm from each of the organic EL devices was observed, and hence it was found that light emission from FIrpic was obtained.

The characteristics of the produced organic EL devices are shown in Table 3.

TABLE 3

| Example | H1 Compound No. | H2 Compound No. | Luminance (cd/m$^2$) | Voltage (V) | Visual luminous efficiency (lm/W) | Luminance half time (h) |
|---|---|---|---|---|---|---|
| 27 | 2-29 | 3-2 | 560 | 8.3 | 8.5 | 3,000 |
| 28 | 2-29 | 3-3 | 560 | 9.2 | 7.7 | 3,000 |
| 29 | 2-29 | 3-4 | 564 | 9.2 | 7.7 | 3,000 |
| 30 | 2-29 | 3-5 | 543 | 9.1 | 7.5 | 3,000 |
| 31 | 2-29 | 3-6 | 558 | 8.3 | 8.5 | 2,500 |
| 32 | 2-29 | 3-8 | 564 | 9.2 | 7.7 | 3,000 |
| 33 | 2-29 | 3-10 | 558 | 8.7 | 8.1 | 3,000 |
| 34 | 2-29 | 3-13 | 557 | 8.9 | 7.9 | 3,000 |
| 35 | 2-29 | 3-17 | 535 | 8.7 | 7.8 | 2,000 |
| 36 | 2-29 | 3-22 | 560 | 8.9 | 7.9 | 3,000 |
| 37 | 2-29 | 3-38 | 560 | 9.2 | 7.7 | 3,000 |
| 38 | 2-29 | 3-52 | 557 | 9.2 | 7.6 | 2,000 |
| Comparative Example 16 | 2-29 | — | 380 | 11.8 | 4.0 | 500 |

It is understood from Table 3 that each of Examples 27 to 38 is improved in luminance and lifetime characteristic, and hence shows satisfactory characteristics.

Example 39

Each thin film was laminated by a vacuum deposition method at a degree of vacuum of $4.0 \times 10^{-4}$ Pa on a glass substrate on which an anode formed of ITO having a thickness of 150 nm had been formed. First, CuPc was formed into a hole-injecting layer having a thickness of 20 nm on the ITO. Next, NPB was formed into a hole-transporting layer having a thickness of 20 nm. Next, Compound 1-2 serving as a first host, Compound 3-2 serving as a second host, and tris(2-phenylpyridine)iridium (III) (Ir(PPy)$_3$) serving as a light-emitting layer guest were co-deposited from vapor deposition sources different from one another to form a light-emitting layer having a thickness of 30 nm. At this time, a vapor deposition rate ratio among the first host, the second host, and Ir(PPy)$_3$ was 47:47:6. Next, aluminum(III) bis(2-methyl-8-quinolinato)-4-phenylphenolate (BAlq) was formed into a hole-blocking layer having a thickness of 10 nm. Next, Alq$_3$ was formed into an electron-transporting layer having a thickness of 40 nm. Further, LiF was formed into an electron-injecting layer having a thickness of 0.5 nm on the electron-transporting layer. Finally, Al was formed into a cathode having a thickness of 100 nm on the electron-injecting layer. Thus, an organic EL device was produced.

An external power source was connected to the resultant organic EL device to apply a DC voltage thereto. As a result, an emission spectrum having a local maximum wavelength of 517 nm was observed, and hence it was found that light emission from Ir(PPy)$_3$ was obtained.

Examples 40 to 50

Organic EL devices were each produced in the same manner as in Example 39 except that a compound shown in Table 4 was used as the second host of the light-emitting layer.

Examples 51 to 62

Organic EL devices were each produced in the same manner as in Example 39 except that: Compound 1-3 was used as the first host of the light-emitting layer; and a compound shown in Table 1 was used as the second host thereof.

An external power source was connected to each of the resultant organic EL devices to apply a DC voltage thereto. As a result, an emission spectrum having a local maximum wavelength of 517 nm from each of the organic EL devices was observed, and hence it was found that light emission from Ir(PPy)$_3$ was obtained.

Examples 63 to 65

Organic EL devices were each produced in the same manner as in Example 39 except that; Compound 3-3 was used as the second host of the light-emitting layer; and a compound shown in Table 4 was used as the first host thereof.

An external power source was connected to each of the resultant organic EL devices to apply a DC voltage thereto. As a result, an emission spectrum having a local maximum wavelength of 517 nm from each of the organic EL devices was observed, and hence it was found that light emission from Ir(PPy)$_3$ was obtained.

Examples 66 to 68

Organic EL devices were each produced in the same manner as in Example 39 except that the first host and second host of the light-emitting layer were preliminarily mixed and vapor-deposited from one evaporation source.

An external power source was connected to each of the resultant organic EL devices to apply a DC voltage thereto. As a result, an emission spectrum having a local maximum wavelength of 517 nm from each of the organic EL devices was observed, and hence it was found that light emission from Ir(PPy)$_3$ was obtained.

Comparative Examples 17 to 33

Organic EL devices were each produced in the same manner as in Example 39 except that a compound shown in Table 5 was used alone as the light-emitting layer host. A host amount was set to the same amount as the total of the first host and second host in Example 39, and a guest amount was similarly set. A power source was connected to each of the resultant organic EL devices to apply a DC voltage thereto. As a result, an emission spectrum having a local maximum wavelength of 517 nm from each of the organic EL devices was observed, and hence it was found that light emission from Ir(PPy)$_3$ was obtained.

The characteristics of the produced organic EL devices are shown in Tables 4 and 5. In each of Tables 4 and 5, a luminance, a voltage, and luminous efficiency are values at a driving current of 20 mA/cm$^2$, and a luminance half time is a value at an initial luminance of 1,000 cd/m$^2$.

TABLE 4

| Example | H1 Compound No. | H2 Compound No. | Luminance (cd/m$^2$) | Voltage (V) | Visual luminous efficiency (lm/W) | Luminance half time (h) |
|---|---|---|---|---|---|---|
| 39 | 1-2 | 3-2 | 10,200 | 3.9 | 40.6 | 30,000 |
| 40 | 1-2 | 3-3 | 10,200 | 3.9 | 41.1 | 30,000 |
| 41 | 1-2 | 3-4 | 10,300 | 3.9 | 41.5 | 30,000 |
| 42 | 1-2 | 3-5 | 9,900 | 3.9 | 40.1 | 30,000 |
| 43 | 1-2 | 3-6 | 10,200 | 3.6 | 45.1 | 25,000 |
| 44 | 1-2 | 3-8 | 10,300 | 3.9 | 41.5 | 30,000 |
| 45 | 1-2 | 3-10 | 10,200 | 3.7 | 43.3 | 30,000 |
| 46 | 1-2 | 3-13 | 10,200 | 3.8 | 42.4 | 30,000 |
| 47 | 1-2 | 3-17 | 9,800 | 3.7 | 41.6 | 20,000 |
| 48 | 1-2 | 3-22 | 10,200 | 3.8 | 42.4 | 30,000 |
| 49 | 1-2 | 3-38 | 10,200 | 3.9 | 41.1 | 30,000 |
| 50 | 1-2 | 3-52 | 10,200 | 4.8 | 33.4 | 21,000 |
| 51 | 1-3 | 3-2 | 10,200 | 3.7 | 43.7 | 29,000 |
| 52 | 1-3 | 3-3 | 10,200 | 3.7 | 43.1 | 29,000 |
| 53 | 1-3 | 3-4 | 10,300 | 3.7 | 43.6 | 29,000 |
| 54 | 1-3 | 3-5 | 9,900 | 3.7 | 41.7 | 29,000 |
| 55 | 1-3 | 3-6 | 10,200 | 4.1 | 39.4 | 24,000 |
| 56 | 1-3 | 3-8 | 10,300 | 3.7 | 43.6 | 29,000 |
| 57 | 1-3 | 3-10 | 10,200 | 3.9 | 41.0 | 29,000 |
| 58 | 1-3 | 3-13 | 10,200 | 3.8 | 41.9 | 29,000 |
| 59 | 1-3 | 3-17 | 9,800 | 3.9 | 39.4 | 19,000 |
| 60 | 1-3 | 3-22 | 10,200 | 3.8 | 41.9 | 29,000 |
| 61 | 1-3 | 3-38 | 10,200 | 3.7 | 43.1 | 29,000 |
| 62 | 1-3 | 3-52 | 10,200 | 3.7 | 43.1 | 19,000 |
| 63 | 1-1 | 3-3 | 10,200 | 4.2 | 38.1 | 30,000 |
| 64 | 1-103 | 3-3 | 10,200 | 3.8 | 42.6 | 30,000 |
| 65 | 1-104 | 3-3 | 10,200 | 4.1 | 38.9 | 30,000 |
| 66 | 1-1 | 3-3 | 10,100 | 4.1 | 38.6 | 30,000 |
| 67 | 1-103 | 3-3 | 10,100 | 3.7 | 43.3 | 30,000 |
| 68 | 1-104 | 3-3 | 10,100 | 4.0 | 39.5 | 30,000 |

TABLE 5

| Comparative Example | Host Compound No. | Luminance (cd/m$^2$) | Voltage (V) | Visual luminous efficiency (lm/W) | Luminance half time (h) |
|---|---|---|---|---|---|
| 17 | 1-1 | 9,000 | 5.5 | 25.7 | 4,000 |
| 18 | 1-2 | 9,000 | 5.5 | 25.7 | 5,000 |
| 19 | 1-3 | 8,000 | 5.0 | 25.1 | 4,000 |
| 20 | 1-103 | 8,800 | 5.0 | 27.8 | 4,000 |
| 21 | 1-104 | 9,100 | 5.4 | 26.5 | 5,000 |
| 22 | 3-2 | 10,200 | 7.3 | 22.0 | 3,000 |
| 23 | 3-3 | 10,200 | 7.2 | 22.3 | 3,000 |
| 24 | 3-4 | 10,200 | 7.2 | 22.3 | 3,000 |
| 25 | 3-5 | 9,900 | 7.2 | 21.7 | 3,000 |
| 26 | 3-6 | 10,100 | 6.6 | 24.2 | 2,500 |
| 27 | 3-8 | 10,200 | 7.2 | 22.3 | 3,000 |
| 28 | 3-10 | 10,100 | 6.8 | 23.2 | 3,000 |
| 29 | 3-13 | 10,100 | 7.0 | 22.7 | 3,000 |
| 30 | 3-17 | 9,700 | 6.8 | 22.3 | 2,000 |
| 31 | 3-22 | 10,200 | 7.0 | 23.0 | 3,000 |
| 32 | 3-38 | 10,200 | 7.2 | 22.3 | 3,000 |
| 33 | 3-52 | 10,100 | 7.2 | 22.1 | 2,000 |

It is understood from Tables 4 and 5 that each of Examples 39 to 68 is improved in luminance and lifetime characteristic, and hence shows satisfactory characteristics.

Example 69

Each thin film was laminated by a vacuum deposition method at a degree of vacuum of 4.0×10$^{-4}$ Pa on a glass substrate on which an anode formed of ITO having a thickness of 150 nm had been formed. First, CuPC was formed into a hole-injecting layer having a thickness of 20 nm on the ITO. Next, NPB was formed into a hole-transporting layer having a thickness of 20 nm. Next, Compound 2-5 serving as a first host, Compound 3-2 serving as a second host, and Ir(PPy)$_3$ serving as a light-emitting layer guest were co-deposited from vapor deposition sources different from one another to form a light-emitting layer having a thickness of 30 nm. At this time, a vapor deposition rate ratio among the first host, the second host, and Ir(PPy)$_3$ was 47:47:6. Next, BAlq was formed into a hole-blocking layer having a thickness of 10 nm. Next, Alq$_3$ was formed into an electron-transporting layer having a thickness of 40 nm. Further, LiF was formed into an electron-injecting layer having a thickness of 0.5 nm on the electron-transporting layer. Finally, Al was formed into a cathode having a thickness of 100 nm on the electron-injecting layer. Thus, an organic EL device was produced.

An external power source was connected to the resultant organic EL device to apply a DC voltage thereto. As a result, an emission spectrum having a local maximum wavelength of 517 nm was observed, and hence it was found that light emission from Ir(PPy)$_3$ was obtained. The characteristics of the produced organic EL device are shown in Table 6.

Examples 70 to 80

Organic EL devices were each produced in the same manner as in Example 69 except that a compound shown in Table 6 was used as the second host of the light-emitting layer.

Examples 81 to 92

Organic EL devices were each produced in the same manner as in Example 69 except that: Compound 2-29 was used as the first host of the light-emitting layer; and a compound shown in Table 6 was used as the second host thereof.

first host and second host in Example 69. An external power source was connected to each of the resultant organic EL devices to apply a DC voltage thereto. As a result, an emission spectrum having a local maximum wavelength of 517 nm from each of the organic EL devices was observed, and hence it was found that light emission from $Ir(PPy)_3$ was obtained.

In Table 6, the luminance, external quantum efficiency, and luminance half lifetime of each of the produced organic EL devices are shown. The luminance and the external quantum efficiency are values at a driving current of 20 $mA/cm^2$, and the luminance half time is a value at an initial luminance of 1,000 $cd/m^2$.

TABLE 6

| Example | H1 Compound No. | H2 Compound No. | Luminance (cd/m²) | Voltage (V) | Visual luminous efficiency (lm/W) | Luminance half time (h) |
|---|---|---|---|---|---|---|
| 69 | 2-5 | 3-2 | 10,100 | 3.8 | 41.4 | 24,000 |
| 70 | 2-5 | 3-3 | 10,100 | 3.9 | 40.8 | 24,000 |
| 71 | 2-5 | 3-4 | 10,100 | 3.9 | 40.8 | 24,000 |
| 72 | 2-5 | 3-5 | 9,800 | 3.9 | 39.4 | 24,000 |
| 73 | 2-5 | 3-6 | 10,000 | 4.3 | 36.4 | 20,000 |
| 74 | 2-5 | 3-8 | 10,100 | 3.9 | 40.8 | 24,000 |
| 75 | 2-5 | 3-10 | 10,000 | 4.1 | 38.1 | 24,000 |
| 76 | 2-5 | 3-13 | 10,000 | 4.0 | 39.1 | 24,000 |
| 77 | 2-5 | 3-17 | 9,600 | 4.1 | 36.6 | 16,000 |
| 78 | 2-5 | 3-22 | 10,100 | 4.0 | 39.4 | 24,000 |
| 79 | 2-5 | 3-38 | 10,100 | 3.9 | 40.8 | 24,000 |
| 80 | 2-5 | 3-52 | 10,000 | 3.9 | 40.4 | 16,000 |
| 81 | 2-29 | 3-2 | 12,500 | 4.8 | 40.7 | 27,000 |
| 82 | 2-29 | 3-3 | 12,500 | 4.7 | 41.5 | 27,000 |
| 83 | 2-29 | 3-4 | 12,600 | 4.7 | 41.9 | 27,000 |
| 84 | 2-29 | 3-5 | 12,200 | 4.7 | 40.7 | 27,000 |
| 85 | 2-29 | 3-6 | 12,500 | 4.1 | 48.0 | 22,500 |
| 86 | 2-29 | 3-8 | 12,600 | 4.7 | 41.9 | 27,000 |
| 87 | 2-29 | 3-10 | 12,500 | 4.4 | 45.0 | 27,000 |
| 88 | 2-29 | 3-13 | 12,500 | 4.5 | 43.5 | 27,000 |
| 89 | 2-29 | 3-17 | 12,100 | 4.4 | 43.5 | 18,000 |
| 90 | 2-29 | 3-22 | 12,500 | 4.5 | 43.5 | 27,000 |
| 91 | 2-29 | 3-38 | 12,500 | 4.7 | 41.5 | 27,000 |
| 92 | 2-29 | 3-52 | 12,500 | 4.7 | 41.5 | 18,000 |
| 93 | 2-5 | 3-3 | 10,100 | 3.8 | 41.8 | 24,000 |
| Comparative Example 34 | 2-5 | — | 9,100 | 5.6 | 25.4 | 5,000 |
| 35 | 2-29 | — | 9,600 | 8.2 | 18.5 | 4,000 |

Example 93

An organic EL device was produced in the same manner as in Example 69 except that the first host and the second host were preliminarily mixed and vapor-deposited from one evaporation source to form a light-emitting layer.

An external power source was connected to each of the resultant organic EL devices to apply a DC voltage thereto. As a result, an emission spectrum having a local maximum wavelength of 517 nm from each of the organic EL devices was observed, and hence it was found that light emission from $Ir(PPy)_3$ was obtained.

Comparative Examples 34 and 35

Organic EL devices were each produced in the same manner as in Example 69 except that a compound shown in Table 6 was used alone as the light-emitting layer host. A host amount was set to the same amount as the total of the It is understood from Table 6 that each of Examples 69 to 93 is improved in luminance and lifetime characteristic, and hence shows satisfactory characteristics.

INDUSTRIAL APPLICABILITY

The organic EL device of the present invention has a high technological value in its application to, for example, flat panel displays (such as a cellular phone display device, anon-vehicle display device, an OA computer display device, and a television), light sources each taking advantage of its feature as a surface emitter (such as illumination, a light source for a copying machine, and backlight sources for a liquid crystal display and meters), display boards, and marker lamps.

REFERENCE SIGNS LIST

1 substrate
2 anode
3 hole-injecting layer 4 hole-transporting layer
5 light-emitting layer
6 electron-transporting layer
7 electron-injecting layer
8 cathode

The invention claimed is:
1. An organic electroluminescent device, comprising one or more light-emitting layers between an anode and a cathode opposite to each other, wherein:
  at least one of the light-emitting layers contains a host material and a light-emitting dopant; and
  the host material contains (i) a compound represented by the following general formula (1) or (2) and (ii) a compound represented by the following general formula (3):

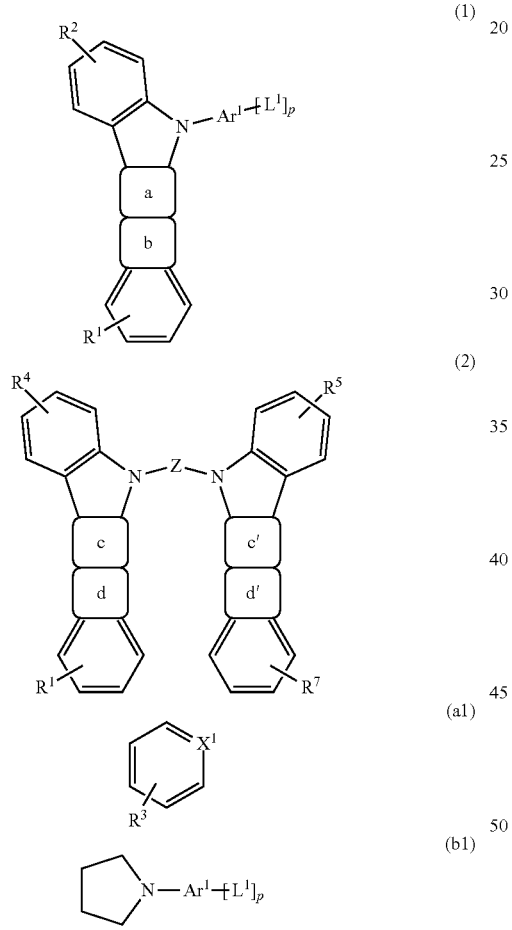

in the general formula (1) or (2):
  a ring a, a ring c; and a ring c' each independently represent an aromatic ring represented by the formula (a1) that is fused to two adjacent rings at arbitrary positions, and $X^1$ represents C—$R^8$;
  a ring b, a ring d, and a ring d' each independently represent a heterocycle represented by the formula (b1) that is fused to two adjacent rings at arbitrary positions;
  $Ar^1$'s each independently represent a (p+1)-valent unsubstituted aromatic hydrocarbon group having 6 carbon atoms, or a (p+1)-valent unsubstituted aromatic heterocyclic group having 3 to 12 carbon atoms;
  Z represents a divalent unsubstituted aromatic hydrocarbon group having 6 carbon atoms; or a divalent unsubstituted aromatic heterocyclic group having 3 carbon atoms, or a divalent substituted or unsubstituted linked aromatic group obtained by linking 2 aromatic rings of the groups;
  $L^1$'s each independently represent an unsubstituted aromatic hydrocarbon group having 6 carbon atoms, an unsubstituted aromatic heterocyclic group having 3 to 12 carbon atoms, or an unsubstituted linked aromatic group obtained by linking 2 aromatic rings of the groups;
  p's each independently represent a substitution number and each independently represent an integer of from 0 to 2;
  $R^1$ and $R^2$ each independently represent a hydrogen atom, or a diarylamino group having 12 carbon atoms and $R^3$ to $R^8$ each independently represent a hydrogen atom;

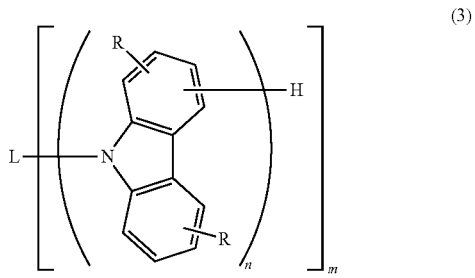

in the general formula (3):
  L represents an m-valent substituted or unsubstituted aromatic hydrocarbon group having 6 to 13 carbon atoms, an m-valent unsubstituted aromatic heterocyclic group having 12 carbon atoms, or an m-valent substituted or unsubstituted linked aromatic group obtained by linking 2 to 3 aromatic rings of the groups, provided that L does not represent a group containing a carbazole ring;
  R's each independently represent a hydrogen atom;
  m represents a substitution number and represents an integer of from 1 to 2; and
  n's each represent a number of repetitions and each independently represent an integer of from 1 to 4, provided that at least one n represents an integer of from 2 to 4, and at least one bond structure represented by the formula (c1) is present in the general formula (3):

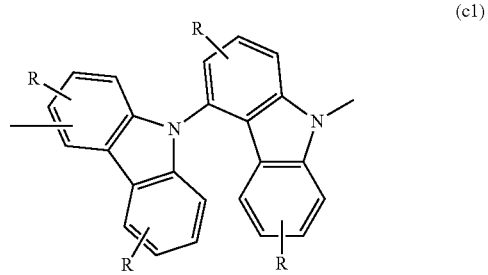

where R's each have the same meaning as that in the general formula (3).

2. An organic electroluminescent device according to claim 1, wherein all bond structures between n carbazole rings in the general formula (3) comprise bond structures represented by the formula (c1) or by the formula (c1) and the following formula (d1):

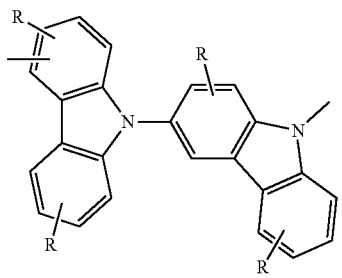

(d1)

where R's each have the same meaning as that in the general formula (3).

3. An organic electroluminescent device according to claim 1, wherein in the general formula (3), L represents an m-valent group produced by removing m hydrogen atoms from an aromatic compound represented by any one of the formulae (4) to (7):

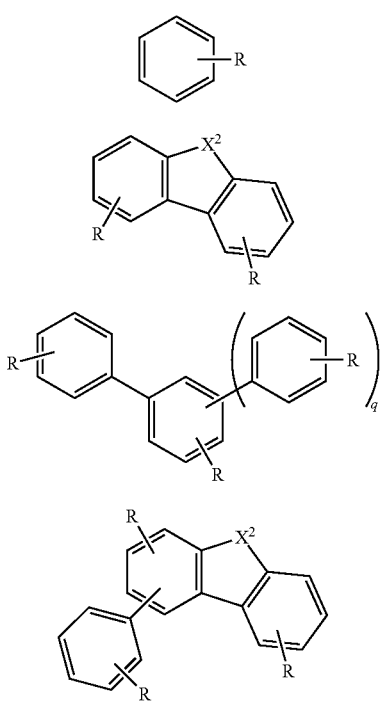

in the formulae (4) to (7), R's each independently represent a hydrogen atom, an alkyl group having 1 to 10 carbon atoms, or a cycloalkyl group having 3 to 11 carbon atoms, $X^2$ represents an oxygen atom or a sulfur atom, and q represents an integer of from 0 to 2.

4. An organic electroluminescent device according to claim 3, wherein in the general formula (3), L represents an m-valent group produced from an aromatic compound represented by any one of the formula (4), (5), or (6).

5. An organic electroluminescent device according to claim 1, wherein in the general formula (3), a product (n×m) of n and m comprises an integer of from 2 to 6.

6. An organic electroluminescent device according to claim 1, wherein the host material contains (i) the compound represented by the general formula (I) and (ii) the compound represented by the general formula (3).

7. An organic electroluminescent device according to claim 1, wherein:

the device comprises a light-emitting layer formed by preliminarily mixing the host material containing the compound represented by the general formula (1) or (2) and the compound represented by the general formula (3), and vapor-depositing the resultant from one evaporation source; and a mixing ratio between the compound represented by the general formula (1) or (2) and the compound represented by the general formula (3) in the light-emitting layer changes by an amount within 5% relative to a preliminary mixing ratio therebetween before the vapor deposition.

8. An organic electroluminescent device according to claim 1, wherein the light-emitting dopant comprises an organometallic complex containing at least one metal selected from the group consisting of ruthenium, rhodium, palladium, silver, rhenium, osmium, iridium, platinum, and gold.

9. An organic electroluminescent device according to claim 1, wherein the weight ratio between (i) the compound represented by general formula (1) or (2) and (ii) the compound represented by general formula (3) is within the range of from 10:90 to 90:10.

10. An organic electroluminescent device according to claim 1, wherein the weight ratio between (i) the compound represented by general formula (1) or (2) and (ii) the compound represented by general formula (3) is within the range of from 20:80 to 80:20.

* * * * *